(12) United States Patent
Brimble et al.

(10) Patent No.: US 7,863,304 B2
(45) Date of Patent: Jan. 4, 2011

(54) ANALOGS OF GLYCYL-PROLYL-GLUTAMATE

(75) Inventors: Margaret Anne Brimble, Auckland (NZ); Paul William Richard Harris, Waitakere (NZ); Frank Sieg, Auckland (NZ)

(73) Assignee: Neuren Pharmaceuticals Limited, Auckland (NZ)

( * ) Notice: Subject to any disclaimer, the term of this patent is extended or adjusted under 35 U.S.C. 154(b) by 327 days.

(21) Appl. No.: 11/986,518

(22) Filed: Nov. 20, 2007

(65) Prior Publication Data

US 2008/0145335 A1    Jun. 19, 2008

Related U.S. Application Data

(63) Continuation-in-part of application No. PCT/US2006/019909, filed on May 23, 2006, and a continuation-in-part of application No. 11/314,424, filed on Dec. 20, 2005, now Pat. No. 7,605,177, which is a continuation-in-part of application No. 10/155,864, filed on May 24, 2002, now Pat. No. 7,041,314, application No. 11/986,518, which is a continuation-in-part of application No. 11/398,032, filed on Apr. 4, 2006, which is a continuation-in-part of application No. 10/155,864, and a continuation-in-part of application No. 11/314,424, and a continuation-in-part of application No. 11/315,784, filed on Dec. 21, 2005.

(60) Provisional application No. 60/683,813, filed on May 23, 2005, provisional application No. 60/293,853, filed on May 24, 2001.

(51) Int. Cl.
*A61K 31/426* (2006.01)
*C07D 277/04* (2006.01)
(52) U.S. Cl. .......................... 514/365; 548/146; 548/200
(58) Field of Classification Search ................. 548/530, 548/537, 146, 200; 514/408, 423, 365
See application file for complete search history.

(56) References Cited

U.S. PATENT DOCUMENTS 6,682,753 B2 * 1/2004 Alexi ........................... 424/422
7,041,314 B2 * 5/2006 Abood et al. ................ 424/451
7,605,177 B2 * 10/2009 Gluckman et al. .......... 514/423

OTHER PUBLICATIONS

Gluckman et al (2002): STN International HCAPLUS database, (Columbus, Ohio), Accession No. 2002:157813.*
Zaczek et al (1993): STN International HCAPLUS database, (Columbus, Ohio), Accession No. 1993:617294.*

* cited by examiner

*Primary Examiner*—Golam M Shameem
(74) *Attorney, Agent, or Firm*—D. Benjamin Borson

(57) ABSTRACT

Embodiments of this invention include novel analogs of Glycyl-Prolyl-Glutamate (GPE) and compositions containing such analogs of GPE. Of these, certain analogs have modified proline residues. Other embodiments of this invention include uses of analogs of GPE to protect neural cells from degeneration and/or death in response to injury or disease. Disorders treatable with compounds and compositions of this invention include hypoxia/ischemia, toxic injury, and chronic neurodegenerative disorders including Parkinson's disease.

14 Claims, 7 Drawing Sheets

ANALOGS OF GLYCYL-PROLYL-GLUTAMATE

CLAIM OF PRIORITY

This application is a continuation-in-part under 35 U.S.C. 1.111(a) of PCT/US06/019909, filed May 23, 2006 which claims priority under 35 U.S.C. 119(e) to U.S. Provisional Application No. 60/683,813, filed May 23, 2005.

This application is also a continuation-in-part of U.S. application Ser. No. 11/314,424, filed Dec. 20, 2005, which is a continuation-in-part of U.S. application Ser. No. 10/155,864, filed May 24, 2002, now U.S. Pat. No. 7,041,314, which claims priority under 35 U.S.C. 119(e) to U.S. Provisional Application No. 60/293,853, filed May 24, 2001.

This application is also a continuation-in-part of U.S. application Ser. No. 11/398,032, filed Apr. 4, 2006, which is a continuation-in-part of U.S. application Ser. No. 10/155,864, filed May 24, 2002, which is a continuation-in-part of U.S. application Ser. No. 11/314,424, filed Dec. 20, 2005 and of U.S. application Ser. No. 11/315,784, filed Dec. 21, 2005, which claims priority under 35 U.S.C. 119(e) to U.S. Provisional Application No. 60/293,853, filed May 24, 2001.

Each of the above applications is expressly incorporated herein by reference as if separately so incorporated.

FIELD OF THE INVENTION

The present invention relates to novel analogs of Glycyl-Prolyl-Glutamate (GPE) and methods of their use. Additionally, this invention relates to the use of these compounds and pharmaceutical compositions thereof in the treatment of diseases and conditions characterised by neuronal degeneration and/or death.

BACKGROUND

The tripeptide Glycyl-L-Prolyl-L-Glutamate (Gly-Pro-Glu or GPE) is a naturally occurring peptide, which is proteolytically cleaved from insulin-like growth factor-1 (IGF-1). IGF-1 is a potent neurotrophic factor produced endogenously in damaged regions of the brain. It has been postulated that some of the neuroprotective actions of IGF-1 are mediated by GPE although the precise mechanism of action remains unclear. GPE has a different mode of action to IGF-1 as GPE does not bind to the IGF-1 receptor. Rather, GPE has been shown to bind with low affinity to the N-methyl-D-aspartate (NMDA) receptor and also elicit a biological response via other mechanisms. GPE facilitates the release of dopamine through interaction with the NMDA receptor but GPE stimulated acetylcholine release is via an unknown, non-NMDA pathway.

It has been demonstrated that GPE can act as a neuronal rescue agent following brain injury or disease, including hypoxic-ischemic brain injury, NMDA challenge, chemical toxins and in animal models of Parkinson's and Alzheimer's disease. Analogs of GPE are thus of interest in the development of novel pharmaceutical agents for the treatment of central nervous system (CNS) injuries and neurodegenerative disorders among others.

The inventors have previously disclosed certain GPE analogs modified at the glycine and/or glutamate residues in order to investigate structure-activity relationships and in an attempt to improve properties such as metabolic stability and oral bioavailability. Some of these are described in U.S. Pat. No. 7,041,314; PCT International Patent Application No: PCT/US02/16361 filed 24 May 2002; U.S. application Ser. No. 11/314,424 filed 20 Dec. 2005; U.S. application Ser. No. 11/315,784 filed 21 Dec. 2005; U.S. patent application Ser. No. 11/398,032 filed 4 Apr. 2006 and U.S. Provisional Patent Application No. 60/782,148 filed 14 Mar. 2006. Each of the aforementioned patents and patent applications is incorporated herein fully by reference. Additionally, certain analogs are described in Trotter et al. *Bioorg. Med. Chem.* 2005, 13, 501; Lai et al. *Bioorg. Med. Chem.* 2005, 13, 533; Brimble et al. *Bioorg. Med. Chem.* 2005, 13, 519).

However, there is an ongoing need for other GPE analogs and compositions for treatment of disorders of the nervous system, including disorders involving neurodegeneration and neural cell death, as well as agents for treating other types of disorders.

SUMMARY

In some aspects, this invention provides novel GPE analogs.

In some embodiments of the invention, the proline residue is modified.

Some embodiments of the invention provide molecules having the structural formula and substituents described below:

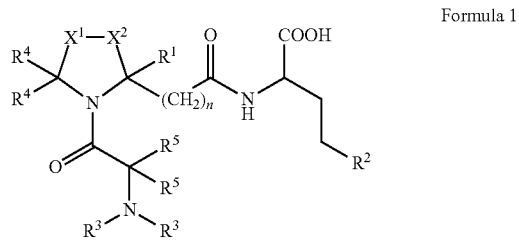

Formula 1

Certain embodiments of this invention include compounds of Formula 1 or a pharmaceutically acceptable salt or hydrate thereof, wherein:

the bond between $X^1$ and $X^2$ may be saturated or unsaturated;

$X^1$ is selected from the group consisting of $CH_2$, S, C(OH)H and in the case where the bond between $X^1$ and $X^2$ is unsaturated, CH;

$X^2$ is selected from the group consisting of $CH_2$, $CH_2CH_2$ and in the case where the bond between $X^1$ and $X^2$ is unsaturated, CH;

$R^1$ is selected from the group consisting of H, alkyl, alkenyl, aryl, arylalkyl, substituted alkyl, substituted alkenyl, substituted aryl or substituted arylalkyl;

$R^2$ is $CH_3$ or COOH;

$R^3$ is selected from the group consisting of H, alkyl or $NR^3R^3$ taken together is pyrrolidino or piperidino;

$R^4$ is selected from the group consisting of H, alkyl, alkenyl, aryl, arylalkyl, substituted alkyl, substituted alkenyl, substituted aryl or substituted arylalkyl;

$R^5$ is selected from the group consisting of H, alkyl, alkenyl, aryl, arylalkyl, substituted alkyl, substituted alkenyl, substituted aryl or substituted arylalkyl;

n is an integer from 0 to 2.

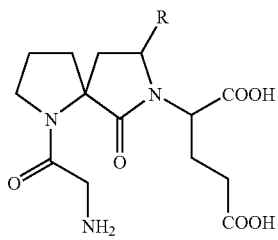

Formula 2

Other embodiments include compounds of Formula 2 or a pharmaceutically acceptable salt or hydrate thereof, wherein R is H or OH.

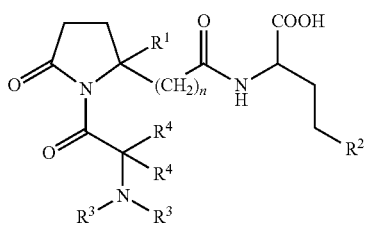

Formula 3

Additional embodiments include compounds of Formula 3 or a pharmaceutically acceptable salt or hydrate thereof, wherein or a pharmaceutically acceptable salt or hydrate thereof, wherein:

$R^1$ is selected from the group consisting of H, alkyl, alkenyl, aryl, arylalkyl, substituted alkyl, substituted alkenyl, substituted aryl or substituted arylalkyl;

$R^2$ is $CH_3$ or COOH;

$R^3$ is selected from the group consisting of H, alkyl or $NR^3R^3$ taken together is pyrrolidino or piperidino;

$R^4$ is selected from the group consisting of H, alkyl, alkenyl, aryl, arylalkyl, substituted alkyl, substituted alkenyl, substituted aryl or substituted arylalkyl;

n is an integer from 0 to 2.

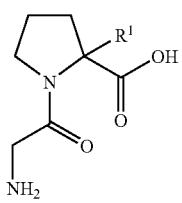

Formula 4

Further embodiments include a compound of Formula 4 or a pharmaceutically acceptable salt or hydrate thereof, wherein $R^1$ is selected from the group consisting of H, alkyl, alkenyl, aryl, arylalkyl, substituted alkyl, substituted alkenyl, substituted aryl or substituted arylalkyl.

Other aspects of the invention provide pharmaceutically acceptable salts of the compounds described in Formulas 1-4.

It should be understood that compounds of this invention include stereoisomers, enantiomers, conformers and the like of the structural formulae presented. Additionally, it should be understood that compounds of this invention may be present as racemic mixtures of different stereoisomers. All such stereoisomers are considered part of this invention.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In yet further aspects, this invention provides a method of treating an animal having a disease or injury capable of treatment by administration of a suitable compound, comprising administration to that animal of at least one compound of this invention, optionally in conjunction with at least one other conventional therapeutic agent for the disease being treated.

In still further aspects the animal to be treated is a human.

In still further aspects, this invention provides methods of preparing the compounds of Formulas 1-4 of this invention.

In yet other aspects, this invention provides methods of synthesising, formulating and preparing pharmaceutical preparations comprising compounds of Formulas 1-4 of this invention.

BRIEF DESCRIPTION OF THE FIGURES

This invention is described with respect to specific embodiments thereof. Other features, characteristics and embodiments of this invention can be appreciated with reference to the figures, in which.

DETAILED DESCRIPTION OF THE INVENTION

Definitions

Figure 1:
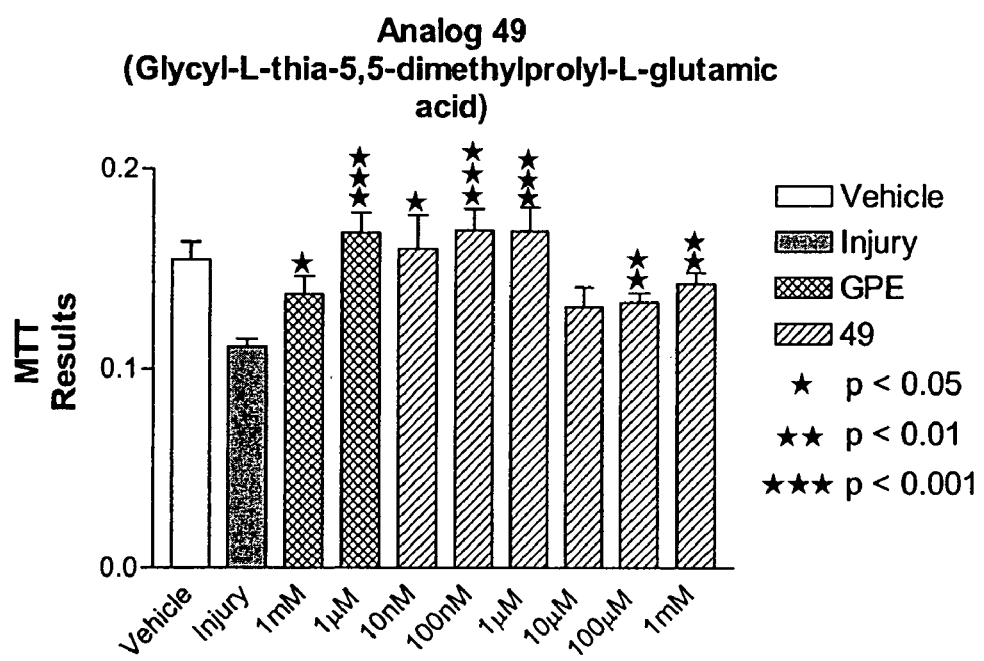
FIG. 1 is a graph showing effects of analog 49 (Glycyl-L-thia-5,5-dimethylprolyl-L-glutamic acid) on neuronal survival following administration of apoptosis-inducing toxin (100 nM okadaic acid) on cortical cell culture.

"Alkenyl" refers to an unsaturated branched, straight chain or cyclic hydrocarbon radical having at least one carbon-carbon double bond. The radical can be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are ($C_2$-$C_6$) alkenyl and in other embodiments allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are ($C_1$-$C_6$) alkyl.

"Alkynyl" refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is ($C_2$-$C_6$) alkynyl.

"Aryl" refers to an unsaturated cyclic hydrocarbon radical with a conjugated π electron system. Exemplary aryl groups include phenyl, naphthyl and the like. In some embodiments the aryl group is ($C_5$-$C_{20}$) aryl.

"Arylalkyl" refers to a straight chain alkyl, alkenyl or alkynyl group wherein one of the hydrogen atoms bonded to the terminal carbon is replaced with an aryl group. Exemplary arylalkyl groups include benzyl, naphthylmethyl, benzylidene and the like.

The term "Glycyl-Prolyl-Glutamate" or "Gly-Pro-Glu" or "GPE" refers to a tripeptide containing the named amino acids. It should be understood that the above named compounds also include the C-terminal acid form of the peptide, also called "Glycyl-Prolyl-Glutamic Acid."

A "growth factor" refers to an extracellular polypeptide-signalling molecule that stimulates a cell to grow or proliferate.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, terahydrofuran, ($C_1$-$C_{10}$) substituted amines, ($C_2$-$C_6$) thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable salt" refers to a salt that is pharmaceutically acceptable and has the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt can be a mono-acid mono-salt or a di-salt; and similarly where there are more than two acidic groups present, some or all of such groups can be salified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

"Substituted" refers to where one or more of the hydrogen atoms on an alkyl, heteroalkyl, alkenyl, alkynyl, aryl, heteroaryl or arylalkyl radical are independently replaced with another substituent. Examples of substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR')—NR'R', trihalomethyl and halogen where each R' is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for that disease; that is, an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compounds of the Invention

One aspect of the invention includes molecules having the structural formulae and substituents described below:

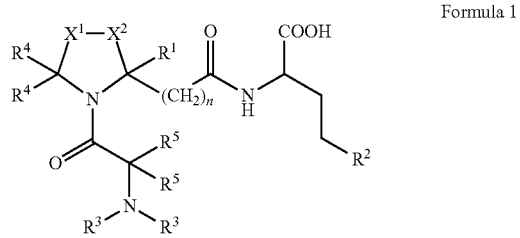

Formula 1

Some embodiments of the invention comprise a compound of Formula 1 or a pharmaceutically acceptable salt or hydrate thereof, wherein:
the bond between $X^1$ and $X^2$ may be saturated or unsaturated;
$X^1$ is selected from the group consisting of $CH_2$, S, C(OH)H and in the case where the bond between $X^1$ and $X^2$ is unsaturated, CH;
$X^2$ is selected from the group consisting of $CH_2$, $CH_2CH_2$ and in the case where the bond between $X^1$ and $X^2$ is unsaturated, CH;
$R^1$ is selected from the group consisting of H, alkyl, alkenyl, aryl, arylalkyl, substituted alkyl, substituted alkenyl, substituted aryl or substituted arylalkyl;
$R^2$ is $CH_3$ or COOH;
$R^3$ is selected from the group consisting of H, alkyl or $NR^3R^3$ taken together is pyrrolidino or piperidino;
$R^4$ is selected from the group consisting of H, alkyl, alkenyl, aryl, arylalkyl, substituted alkyl, substituted alkenyl, substituted aryl or substituted arylalkyl;
$R^5$ is selected from the group consisting of H, alkyl, alkenyl, aryl, arylalkyl, substituted alkyl, substituted alkenyl, substituted aryl or substituted arylalkyl;
n is an integer from 0 to 2.

In further embodiments of the invention the compounds are compounds of Formula 1 wherein $X^1$ is $C_1H_2$; $X^2$ is $CH_2$; $R^1$ is $CH_2$—$CH_3$; $R^2$ is COOH; $R^3$ is H; $R^4$ is H; $R^5$ is H; n is 0 (analog 2: Glycyl-L-2-ethylprolyl-L-glutamic acid ("G-2EthylPE")).

In still other embodiments of the invention the compounds are compounds of Formula 1 where $X^1$ is $CH_2$; $X^2$ is $CH_2$; $R^1$ is $CH_2$—$CH_2$—$CH_3$; $R^2$ is COOH; $R^3$ is H; $R^4$ is H; $R^5$ is H; n is 0 (analog 3: Glycyl-L-2-propylprolyl-L-glutamic acid ("G-2PropylPE")).

In yet further embodiments of the invention the compounds are compounds of Formula 1 where $X^1$ is $CH_2$; $X^2$ is $CH_2$; $R^1$ is $CH_2$—CH=$CH_2$; $R^2$ is COOH; $R^3$ is H; $R^4$ is H; $R^5$ is H; n is 0 (analog 4: Glycyl-L-2-allylprolyl-L-glutamic acid trifluoroacetate(G-2Allyl PE)).

In other embodiments of the invention the compounds are compounds of Formula 1 where $X^1$ is $CH_2$; $X^2$ is $CH_2$; $R^1$ is benzyl; $R^2$ is COOH; $R^3$ is H; $R^4$ is H; $R^5$ is H; n is 0 (5: Glycyl-L-2-benzylprolyl-L-glutamic acid trifluoroacetate ("G-2BenzylPE")).

In still other embodiments of the invention the compounds are compounds of Formula 1 where $X^1$ is S; $X^2$ is $CH_2$; $R^1$ is H; $R^2$ is COOH; $R^3$ is H; $R^4$ is H; $R^5$ is H; n is 0 (analog 48: Glycyl-L-4-thiaprolyl-L-glutamic acid trifluoroacetate).

In further embodiments of the invention the compounds are compounds of Formula 1 where $X^1$ is S; $X^2$ is $CH_2$; $R^1$ is H; $R^2$ is COOH; $R^3$ is H; $R^4$ is $CH_3$; $R^5$ is H; n is 0 (analog 49: Glycyl-L-thia-5,5-dimethylprolyl-L-glutamic acid ("G-thiadiMePE")).

In yet further embodiments of the invention the compounds are compounds of Formula 1 wherein $X^1$ is $CH_2$; $X^2$ is $CH_2$; $R^1$ is H; $R^2$ is COOH; $R^3$ is H; $R^4$ is $CH_3$; $R^5$ is H; n is 0 (analog 50: Glycyl-(D,L)-5,5-dimethylprolyl-L-glutamic acid).

In other embodiments of the invention the compounds are compounds of Formula 1 wherein $X^1$ is C(OH)H; $X^2$ is $CH_2$; $R^1$ is H; $R^2$ is COOH; $R^3$ is H; $R^4$ is H; $R^5$ is H; n is 0 (analog 60: Glycyl-trans-4-hydroxy-L-prolyl-L-glutamic acid ("GHypE")).

In still other embodiments of the invention the compounds are compounds of Formula 1 wherein $X^1$ is $CH_2$; $X^2$ is $CH_2$; $R^1$ is H; $R^2$ is COOH; $R^3$ is H; $R^4$ is H; $R^5$ is H; n is 1 (analog 62: Glycyl-L-homoprolyl-L-Glutamic Acid ("GHomoPE")).

In further embodiments of the invention the compounds are compounds of Formula 1 wherein the bond between $X^1$ and $X^2$ is unsaturated; $X^1$ is CH; $X^2$ is CH; $R^1$ is H; $R^2$ is COOH; $R^3$ is H; $R^4$ is H; $R^5$ is H; n is 0 (analog 63: Glycyl-L-3,4-dehydroprolyl-L-glutamic acid trifluoroacetate ("G-3,4-dehydroPE.TFA")).

In yet further embodiments of the invention the compounds are compounds of Formula 1 wherein: $X^1$ is $CH_2$; $X^2$ is $CH_2$; $R^1$ is H; $R^2$ is COOH; $R^3$ is H; $R^4$ is H; $R^5$ is $CH_3$; n is 0 (analog 64: Aminoisobutryl-L-prolyl-L-glutamic acid ("AibPE")).

In still further embodiments of the invention the compounds are compounds of Formula 1 wherein $X^1$ is $CH_2$; $X^2$ is $CH_2$; $R^1$ is H; $R^2$ is $CH_3$; $R^3$ is H; $R^4$ is H; $R^5$ is H; n is 0 (analog 65: Glycyl-L-prolyl-L-Norvaline ("GP Norvaline")).

In other embodiments of the invention the compounds are compounds of Formula 1 wherein $X^1$ is $CH_2$; $X^2$ is $CH_2CH_2$; $R^1$ is H; $R^2$ is COOH; $R^3$ is H; $R^4$ is H; $R^5$ is H; n is 0 (analog 66: Glycyl-D,L-pipecolinyl-L-glutamic Acid ("G(D,L)PipE")).

In still other embodiments of the invention the compounds are compounds of Formula 1 wherein $X^1$ is $CH_2$; $X^2$ is $CH_2$; $R^1$ is $CH_3$; $R^2$ is COOH; $NR^3R^3$ taken together is pyrrolidino; $R^4$ is H; $R^5$ is H; n is 0 (analog 67: Pyrrolidinoglycyl-L-2-Methyl-proline-L-Glutamic Acid ("PyrrolidinoG-2MePE")).

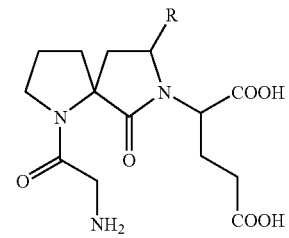

Formula 2

In certain embodiments; the invention comprises compounds of Formula 2 or a pharmaceutically acceptable salt or hydrate thereof, wherein R is H or OH. In further embodiments of the invention the compounds are compounds of Formula 2 where R is H (analog 35: (2S,5'R)-[1'-(2"-Aminoacetyl)-6'-oxo-1',7'-diazaspiro[4.4]non-7'-yl]-1,5-pentanedioic acid ("GP-5,5-spirolactamE")).

In yet further embodiments of the invention the compounds are compounds of Formula 2 where R is OH (analog 36: (2S,5'R,8'R)- and (2S,5'R',8'S)-[1'-(2"-Amino-acetyl)-8'-hydroxy-6'-oxo-1',7'-diazaspiro[4.4]non-7'-yl]-1,5-pentanedioic acid ("GP-5,5-hydroxyspirolactamE")).

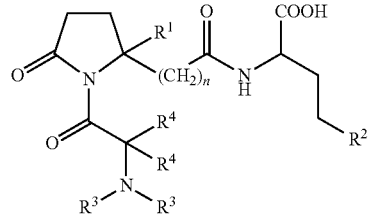

Formula 3

In certain embodiments, compounds of Formula 3 or a pharmaceutically acceptable salt or hydrate thereof, wherein $R^1$ is selected from the group consisting of H, alkyl, alkenyl, aryl, arylalkyl, substituted alkyl, substituted alkenyl, substituted aryl or substituted arylalkyl;

$R^1$ is $CH_3$ or COOH;
$R^3$ is selected from the group consisting of H, alkyl or $NR^3R^3$ taken together is pyrrolidino or piperidino;
$R^4$ is selected from the group consisting of H, alkyl, alkenyl, aryl, arylalkyl, substituted alkyl, substituted alkenyl, substituted aryl or substituted arylalkyl;
n is an integer from 0 to 2, In further embodiments of the invention the compounds are compounds of Formula 3 where $R^1$ is H; $R^2$ is COOH; $R^3$ is H; $R^4$ is H; n is 0 (analog 61: Glycyl-L-2-Pyroglutamyl-L-Glutamic Acid Hydrochloride ("GpyroE.HCl")).

Formula 4

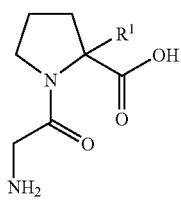

In certain embodiments, the invention comprises compounds of Formula 4 or a pharmaceutically acceptable salt or hydrate thereof, wherein $R^1$ is selected from the group consisting of H, alkyl, alkenyl, aryl, arylalkyl, substituted alkyl, substituted alkenyl, substituted aryl or substituted arylalkyl.

In further embodiments of the invention the compounds are compounds of Formula 4 wherein $R^1$ is $CH_3$ (analog 68: Glycyl-L-2-Methylproline("G-2MeP")).

In certain embodiments, the invention comprises a compound of Formula 4, or a pharmaceutically acceptable salt or hydrate thereof, wherein $R^1$ is methyl.

Other aspects of the invention provide pharmaceutically acceptable salts of the compounds described in Formulas 1-4.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In further aspects, this invention provides methods of treating an animal having a disease or injury capable of treatment by administration of a suitable compound of Formulas 1-4, comprising administration to that animal of at least one compound of this invention, optionally in conjunction with at least one other conventional therapeutic agent for the disease being treated.

In yet further aspects, the animal to be treated is a human.

In still further aspects, this invention provides methods of synthesizing, formulating and preparing pharmaceutical preparations comprising compounds of Formulas 1-4 of this invention.

Those with skill in the art will appreciate that the above structural formulae contain chiral centres, the number of which will depend on the different substituents. The chirality is only indicated for some centres. The chirality can be either R or S at each centre. The formulae drawings represent only one of the possible tautomeric, conformational isomeric or enantiomeric forms, it should be understood that the invention encompasses any tautomeric, conformational isomeric or enantiomeric forms which exhibit biological or pharmacological activity as described herein.

Pharmacology and Utility

Certain aspects of this invention include the use of compounds of the invention in treatment or prevention of cell damage, degeneration and/or death in mammals in response to injury or disease. Some embodiments comprise delivering a composition containing a compound of the invention to an animal suffering from neural degeneration, and in some cases, conditions involving apoptotic and necrotic cell death. In some embodiments, compositions are desirable to treat an injury or disease of the CNS affecting or liable to affect brain cells. Compositions are provided that can also include one or more other agents that promote neural regeneration, decrease cell degeneration or death, or are neuroprotective.

Such other agents can be selected from the group consisting of for example, growth factors and associated derivatives, e.g., insulin-like growth factor-I (IGF-I), insulin-like growth factor-II (IGF-II), the tripeptide GPE, transforming growth factor-β1, activin, growth hormone, nerve growth factor, growth hormone binding protein, and/or IGF-binding proteins.

Other aspects of the invention include compositions and methods of promoting fasiculation of axons. By promoting formation of nerve bundles, compounds of the invention can be useful in treating conditions in which nerve processes (axons and/or dendrites) have become severed, such as in sharp force injuries, local areas of necrosis or disease, or other localized injuries to nerve processes.

In yet other embodiments, compositions and methods to treat or prevent cell damage and death in response to injury and disease, including CNS injury and disease, comprise administration of a therapeutic amount of a compound of the invention alone or in combination with other agents, after the insult. These embodiments can be particularly desirable in situations of unexpected injury, such as in cardiac arrest, trauma such as head injuries caused by automobile accidents, head wounds and the like.

In still further embodiments, compounds of the invention can be used either alone or in combination with other agents to prevent adverse effects of planned brain injury. Such conditions include CABG or other planned surgeries such as brain surgery, vascular surgery or other interventions that can lead to decreased perfusion of the nervous system. By treating an animal, such as a human being, in advance and/or simultaneously and/or after the surgery, adverse neurological effects may be ameliorated.

As indicated above, the present invention is broadly based upon the applicant's finding that compounds of the invention can protect cells, particularly nerve cells, against damage, loss of neurites, and/or apoptotic or necrotic cell death.

It is herein demonstrated that compounds of the invention exhibit neuroprotection in cell culture models of neurodegenerative disease and can therefore be an effective addition or alternative to conventional therapies for neural degeneration.

Although the mechanism of the protective effects is not known, one possible mechanism involves protecting cells from apoptotic and necrotic cell death. However, regardless of the mechanism of action, compounds of the invention can be used as an effective therapy for a variety of neurological diseases, including hypoxia, ischemia and neurotoxin-induced nerve damage. Moreover, compounds of the invention can be used in the absence of any particular neurological deficit to promote neurite outgrowth and fasiculation of nerves. Thus, in situations in which cell death is not necessarily associated with the neurological disorder (e.g., axonal damage such as caused by spinal cord injury), administration of compounds of the invention may be an effective way of promoting neurite regeneration.

Therapeutic Applications

Compositions and methods of the invention find use in the treatment of animals, such as human patients, suffering from neural injury or disease. Still more generally, the compositions and methods of the invention find use in the treatment of mammals, such as human patients, suffering from nerve damage or potential apoptotic and/or necrotic cell death, due to injuries and diseases.

In studies of GPE and the other GPE analogs G-2-MethylPE, G-2AllylPE, diketopiperazine derivatives of GPE, macrocyclic analogs of GPE and L-Ala-PE, a general observation has been made. For compounds that are neuroprotective as assessed using an in vitro system such as those described herein and in other patents and patent applications of the Inventors, the existence of neuroprotection is independent of the type of insult applied. Thus, neurodegenerative effects of hypoxia/ischemia and toxic injury can be mitigated or prevented by GPE and GPE analogs previously disclosed. Additionally, parallel neuroprotective effects of the above previously disclosed GPE analogs are also found in in vivo systems. Thus, compounds that exhibit in vitro neuroprotection also can inhibit neurodegeneration associated with stroke, hypoxia/ischemia traumatic brain injury and animal models of Parkinson's disease and Alzheimer's disease. Moreover, in in vivo studies using previously disclosed GPE analogs, functional deficits and histologically observed neurodegeneration are also at least partially mitigated in a parallel fashion by GPE and previously disclosed GPE analogs. Such functional deficits include disorders of gait, motor coordination and memory. Some of these studies and correlations are described in U.S. Pat. No. 7,041,314, PCT International Patent Application No: PCT/US02/16361 filed 24 May 2002, U.S. application Ser. No. 11/314,424 filed 20 Dec. 2005, U.S. application Ser. No. 11/315,784 filed 21 Dec. 2005, U.S. patent application Ser. No. 11/398,032 filed 4 Apr. 2006 and U.S. Provisional Patent Application No. 60/782,148 filed 14 Mar. 2006. Each of the aforementioned patents and patent applications are incorporated herein fully by reference. Therefore, in vitro studies as described herein can be useful and effective tools for evaluating efficacy of GPE analogs for in vivo use, and results obtained using such in vitro systems are highly predictive of effects observed in vivo and in humans suffering from disorders associated with neurodegeneration.

Specific conditions and diseases characterised by neuronal degeneration, apoptosis and/or necrosis include but are not limited to Alzheimer's disease, Parkinson's disease, multiple sclerosis, amyotrophic lateral sclerosis, spinal muscular atrophy, peripheral neuropathy, Creutzfeldt-Jakob disease, AIDS dementia, progressive supranuclear palsy, myelinopathia centralis diffusa (vanishing white matter disease), chronic neurodegenerative disease, Huntington's disease, stroke, ischemic injury, hypoxic injury, reperfusion injury, head injury, penetrating brain injury, CNS trauma, epilepsy, cerebral ischemia, glaucoma, retinal disorders, optic neuropathy, optic neuritis, Down's syndrome, encephalomyelitis, meningitis, panencephalitis, neuroblastoma, schizophrenia and depression. Each of the above conditions exhibits pathophysiological findings and symptoms that are mimicked by neurotoxicity associated with glutamate toxicity for which GPE and GPE analogs can be of thereapeutic value.

Additionally, compounds of the invention can have application in the induction of nerve bundle formation following insult in the form of trauma, toxin exposure, asphyxia or hypoxia-ischemia. Additionally, compounds of the invention can have application in the treatment or prevention of apoptosis or other forms of neurodegeneration, necrosis or damage in response to injury or disease in the form of cancers, viral infections, autoimmune diseases, neurological diseases and injuries and cardiovascular diseases.

Treatment can be given before an injury, for example, before elective surgery. Examples of relevant elective procedures include neural surgery, in which retraction of lobes of the brain can lead to cerebral oedema, or heart operations, such as valve replacement, in which inevitable small emboli are said to lead to detectable impairment of brain function in some 75% of cases.

It is also known that after a primary insult, there can be both an "early" or immediate phase of neurodegeneration associated with injury or disease and a "late" or delayed phase of neurodegeneration. In some cases, late phase neurodegeneration can be effectively treated by administering a neuroprotective amount of GPE or a GPE analog of this invention from 0 hours to about 100 hours after a primary insult. Even after several hours after a primary insult, during a time after the early phase neurodegeneration, administration of a GPE analog of this invention can mitigate late phase neurodegeneration. Thus, one can prevent or inhibit late phase neurodegeneration by administering a GPE analog of this invention after the primary insult, later than may be required to prevent early phase neurodegeneration.

Determining Efficacy

The neureoprotective activity of compounds of the invention can be measured by in vivo using cell counts by methods known to those skilled in the art including the methods of Klempt et al (Klempt et al, 1992, *Molecular Brain Research:* 13: 93-101), microscopic examinations of morphology, cell counts of surviving and dead neurons stained with thionin/fuchsin and the like. Effects of compounds of the invention can also be measured in vitro using an assay for neurite outgrowth, mass spectroscopy, immunological, or chromatographic methods known in the art. These methods have been well characterized and validated in numerous experimental systems and therefore are predictive of neuroprotective effects in human cells and in animal systems including human beings.

CNS damage can for example be measured clinically by the degree of permanent neurological deficit cognitive function, and/or propensity to seizure disorders. Herein are disclosed histological techniques suitable for measuring effects in vivo. Some methods suitable for in vivo assessment can be found in U.S. Pat. No. 7,041,314, PCT International Patent Application No: PCT/US02/16361 filed 24 May 2002, U.S. application Ser. No. 11/314,424 filed 20 Dec. 2005, U.S. application Ser. No. 11/315,784 filed 21 Dec. 2005, U.S. patent application Ser. No. 11/398,032 filed 4 Apr. 2006 and U.S. Provisional Patent Application No. 60/782,148 filed 14 Mar. 2006. Each of the aforementioned patents and patent applications are incorporated herein fully by reference.

The therapeutic ratio of a compound is understood to be the ratio of (1) the mean dose that causes adverse side effect over (2) the mean dose that causes a desirable therapeutic effect. Thus, for compounds for which have therapeutic effects at relatively low doses and undesirable side effects at high doses, the therapeutic ratio is >1. Therapeutic ratio can be determined, for example, by comparing the dose that produces significant weight loss (or other observable side-effect) divided by the dose that produces anti-apoptotic and anti-necrotic activity in a suitable in vivo animal species such as the rat or mouse. Suitable models include a hypoxic-ischemic injury (Sirimanne et al, 1994 *Journal of Neuroscience Methods:* 55: 7-14) and experimental immune encephalomyelitis (Mendel et al., 1995 *Eur. J. Immunol.:* 25: 1951-1959).

Pharmaceutical Compositions and Administration

Compounds of the invention can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount can vary widely depending on the disease or injury, its severity, the age and relative health of the animal being treated, the potency of the compound(s), and other factors. As anti-apoptotic and anti-necrotic agents, therapeutically effective amounts of compounds of this invention can range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Compounds of the invention can be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic and anti-necrotic agents, compounds of this invention will be administered orally. The amount of a compound of this invention in the composition can vary widely depending on the type of composition, size of a unit dosage, kind of excipients, and other factors well known to those of ordinary skill in the art. In general, the final composition can comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animal's CNS, a compound can be injected directly into a site of neural damage. Such routes of administration can be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS can be increased by administration of a pro-drug form of a compound, which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, inhibiting neurodegeneration and/or restoring nerve function in an animal can comprise administering a therapeutic amount of a compound of the invention in combination with another neuroprotective agent, selected from, for example, GPE, analogs of GPE described in U.S. Pat. No. 7,041,314, PCT International Patent Application No: PCT/US02/16361 filed 24 May 2002, U.S. application Ser. No. 11/314,424 filed 20 Dec. 2005, U.S. application Ser. No. 11/315,784 filed 21 Dec. 2005, U.S. patent application Ser. No. 11/398,032 filed 4 Apr. 2006 or U.S. Provisional Patent Application No. 60/782,148 filed 14 Mar. 2006, a neural regeneration peptide (NRP) as disclosed in U.S. patent application Ser. No. 10/976,699 filed Oct. 29, 2004, PCT International Patent Application No: PCT/US02/026782 filed 22 Aug. 2002 or PCT/US2004/036203, a macrocyclic analog of GPE as described in PCT International Patent Application No: PCT/US2004/008108 filed 16 Mar. 2004, a bicyclic analog of GPE as described in PCT International Patent Application No: PCT/US2004/028308 filed 31 Aug. 2004, growth factors and associated derivatives (insulin-like growth factor-I (IGF-I), insulin-like growth factor-II (IGF-II), transforming growth factor-$\beta 1$, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analog [ORG 2766] and dizolcipine (MK-801), selegiline; glutamate antagonists such as, NPS1506, GV 1505260, MK-801, GV150526; AMPA antagonists such as 2,3-dihydroxy-6-nitro-7-sulfamoylbenzo (f)quinoxaline (NBQX), LY303070 and LY300164; anti-inflammatory agents directed against the addressin MAdCAM-1 and/or its integrin $\alpha 4$ receptors ($\alpha 4\beta 1$ and $\alpha 4\beta 7$), such as anti-MAdCAM-1mAb MECA-367 (ATCC accession no. HB-9478).

The compound can be administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.*: 15: 267), or poly-D-(–)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544,545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment the compound is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

A compound is typically formulated in such vehicles at a pH of from or about 4.5 to 8. It will be understood that use of certain of the foregoing excipients, carriers, or stabilizers will result in the formation of salts of the compound. The final preparation can be a stable liquid or lyophilized solid.

Formulations of the compound in pharmaceutical compositions can also include adjuvants. Typical adjuvants which can be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When the dosage form is a capsule, in addition to the above materials, it can also contain a liquid carrier such as a fatty oil. Other materials of various types can be used as coatings or as modifiers of the physical form of the dosage unit. A syrup or elixir can contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

For injection, intraventricular administration, and other invasive routes of administration, the compounds used must be sterile. Sterility can be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds of this Invention

Starting materials and reagents used in preparing these compounds are either available from commercial suppliers such as Aldrich Chemical Company (Milwaukee, Wis.), Bachem (Torrance, Calif.), Sigma (St. Louis, Mo.), Strem (Newburyport, Mass.) or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and compounds of this invention can be isolated and purified using conventional techniques, including filtration, distillation, crystallization, chromatography, and the like. They can be characterized using conventional methods, including physical constants and spectral data.

All patent and literature references cited throughout the specification are expressly incorporated by reference in their entirety.

EXAMPLES

Example 1

Synthesis of Novel Analogs of GPE

Synthesis of analog 2 (Glycyl-L-2-ethylprolyl-L-glutamic acid), analog 3 (Glycyl-L-2-propylprolyl-L-glutamic acid), analog 4 (Glycyl-L-2-allylprolyl-L-glutamic acid trifluoroacetate), analog 5 (Glycyl-L-2-benzylprolyl-L-glutamic acid trifluoroacetate), analog 35 ((2S,5'R)-[1'-(2"-Amino-acetyl)-6'-oxo-1',7'-diazaspiro[4.4]non-7'-yl]-1,5-pentanedioic acid), analog 36 ((2S,5'R,8'R)- and (2S,5'R,8'S)-[1'-(2"-Amino-acetyl)-8'-hydroxy-6'-oxo-1',7'-diazaspiro[4.4]non- 7'-yl]-1,5-pentanedioic acid), analog 48 (Glycyl-L-4-thiaprolyl-L-glutamic acid trifluoroacetate), analog 49 (Glycyl-L-thia-5,5-dimethylprolyl-L-glutamic acid) and analog 50 (Glycyl-(D,L)-5,5-dimethylprolyl-L-glutamic acid) are described herein.

In order to investigate the importance of the proline residue in GPE, analogs modified at either Pro or at the Pro-Glu bond were synthesized. In particular conformationally restricted analogs were prepared in order to gain insight into the receptor bound conformation. The general synthetic strategy employed involved the preparation of several modified proline residues that were then coupled to a glycine derivative and a glutamic acid di-ester (Scheme 1).

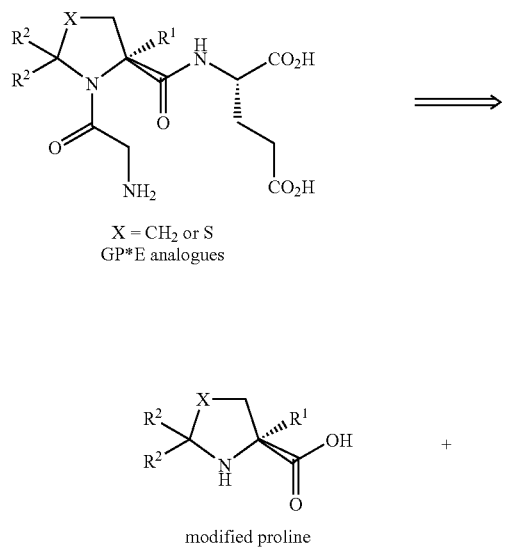

The presence of (S)-2-methylproline (2-MePro) is known to stabilize turns (Bisang, C et al. *J. Am. Chem. Soc.* 1995, 117, 7904; Welsh et al. A. *FEBS Lett.* 1992, 297, 216) and may also prevent peptidases recognizing the Pro-Glu amide bond resulting in resistance to proteolytic degradation (Thaisrivongs et al. *Med. Chem.* 1987, 30, 536). Hence, the synthesis of glycyl-L-2-methylprolyl-L-glutamic acid (G-2MePE) 1 was undertaken. In order to further explore the influence of modifications at this position, four other 2-alkylproline analogs 2-5 were also synthesized (Scheme 2).

The 2-alkylproline derivatives were synthesized using Wang and Germanas's modification of Seebach's method of self-reproducing chirality (Seebach et al. *J. Am. Chem. Soc.* 1983, 105, 5390; Beck et al *J. Org. Synth.* 1992, 72, 62). Condensation of L-proline 6 with choral (trichloroacetaldehyde) gave oxazolidinone 7 (Amedjkouh et al. *Tetrahedron: Asymmetry* 2002, 13, 2229) which was used for the synthesis of the five 2-alkylproline modified tripeptides 1-5. Treatment of 7 with LDA to effect enolate formation followed by alkylation with iodomethane, iodoethane, allyl bromide or benzyl bromide respectively, afforded alkylated oxazolidinones 8-11. Esterification with thionyl chloride (for 8,9) or acetyl chloride (for 10,11) in methanol gave the methyl ester hydrochlorides 12-15 which were coupled with N-benzyloxycarbonyl-glycine 16 (for 12-14) or N-tert-butyloxycarbonyl-glycine 17 (for 14 and 15) to give the dipeptides 18-22.

The optimal conditions for the amide bond formation were investigated using the coupling between 12 and 16; bis(2-oxo-3-oxazolidinyl)phosphinic chloride (BoPCl) was found to be superior (92% yield compared to 66% with DCC) and was used for all subsequent coupling reactions. Hydrolysis of the methyl esters 18,19,20 (NaOH in dioxane) to the carboxylic acids 23,24,25 followed by coupling (BoPCl) with dibenzyl glutamate 28 afforded benzyl protected tripeptides 30,31, 32. Finally global deprotection of the benzyl groups gave tripeptides 1 and 2 whilst concomitant hydrogenolysis of the allyl group in 25 gave tripeptide 3.

For the synthesis of the tripeptides 4 and 5 incorporating a 2-allylproline and a 2-benzylproline unit respectively, Boc and t-butyl protecting groups were used. In these cases coupling of acids 26 and 27 with di-tert-butyl glutamate 29 gave tripeptides 33 and 34 affording tripeptides 4 and 5 as trifluoroacetate salts after deprotection with TFA.

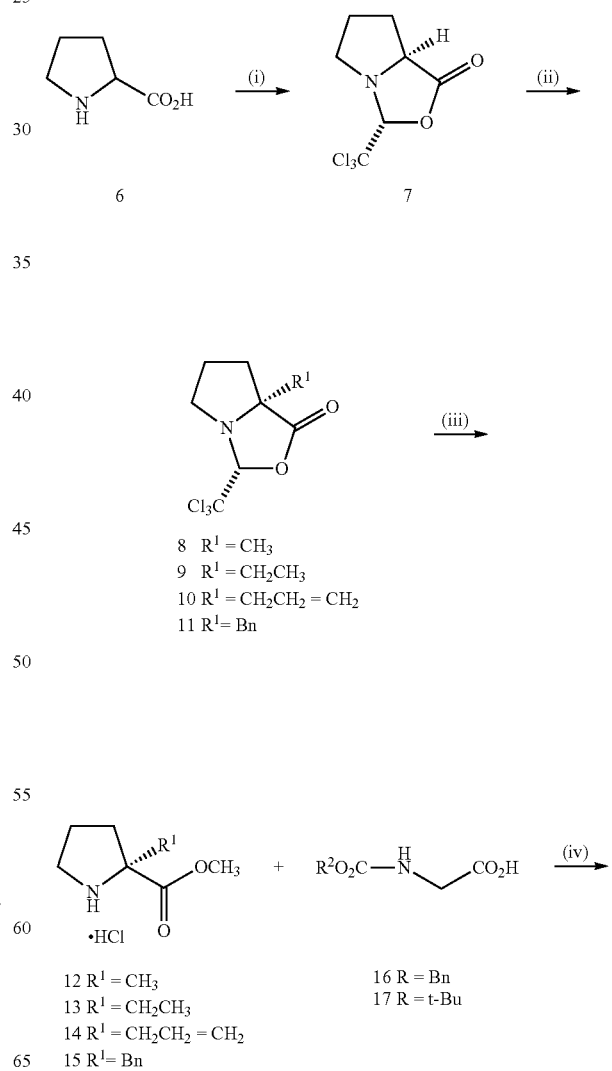

-continued

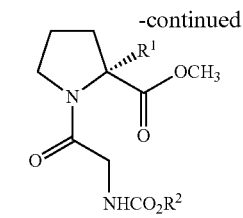

18 R¹ = CH₃, R² = Bn
19 R¹ = CH₂CH₃, R² = Bn
20 R¹ = CH₂CH₂=CH₂, R² = Bn
21 R¹ = CH₂CH₂=CH₂, R² = t-Bu
22 R¹ = Bn, R² = t-Bu

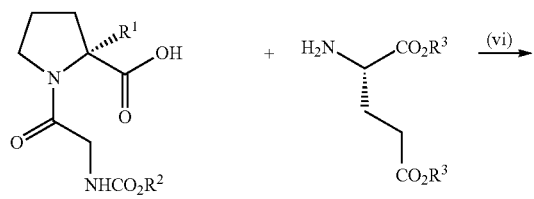

23 R¹ = CH₃, R² = Bn
24 R¹ = CH₂CH₃, R² = Bn
25 R¹ = CH₂CH₂=CH₂, R² = Bn
26 R¹ = CH₂CH₂=CH₂, R² = t-Bu
27 R¹ = Bn, R² = t-Bu

28 R³ = Bn
29 R³ = t-Bu

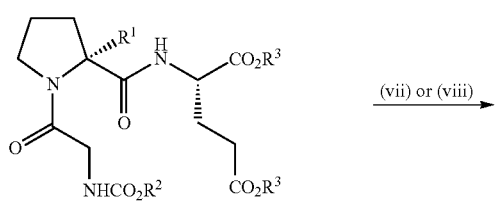

30 R¹ = CH₃, R² = Bn, R³ = Bn
31 R¹ = CH₂CH₃, R² = Bn, R³ = Bn
32 R¹ = CH₂CH₂=CH₂, R² = Bn, R³ = Bn
33 R¹ = CH₂CH₂=CH₂, R² = t-Bu, R³ = t-Bu
34 R¹ = Bn, R² = t-Bu, R³ = t-Bu

-continued

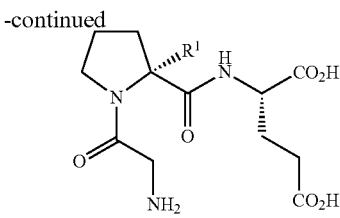

1 R¹ = CH₃
2 R¹ = CH₂CH₃
3 R¹ = CH₂CH₂CH₃
4 R¹ = CH₂CH₂=CH₂
5 R¹ = Bn

Reagents, conditions and yields: (i) chloral, CHCl₃, reflux, 6h (77%); (ii) LDA, THF, -78° C., MeI, EtI, CH₃CH₂=CH₂Br or PhCH₂Br, -78 → -30° C., 4h, 8, 63%, 9, 46%, 10, 60%, 11, 2.5h, 32%; (iii) SOCl₂, CH₃OH, reflux, 3h, 12, 100%, 13, 71%, AcCl, CH₃OH, reflux, 24h, 14, 63%, 15, 48%; (iv) for 18, 19, 20: Et₃N,BoPCl, 16, CH₂Cl₂, rt, 18, 20.5h, 92%, 19, 19.5h, 46%, 20, 20h, 30%; for 21, 22: Et₃N, BoPCl, 17, CH₂Cl₂, rt, 19.5h, 21, 45%, 22, 18.5h, 22%; (v) dioxane, 1 M aq. NaOH, rt, 15-20h, 23, 90%, 24, 95%, 25, 92%, 26, 83%, 27, 95%; (vi) for 30, 31, 32: Et₃N, BoPCl, 28, CH₂Cl₂, rt, 17h, 30, 89%, 31, 17.5h, 70%, 32, 19.5h, 76%; for 33, 34: Et₃N, BoPCl, 29, CH₂Cl₂, rt, 17.5h, 33, 77%, 34, 17h, 68%; (vii) H₂, 10% Pd/C, CH₃OH/H₂O (90:10), rt, 23h, 1, 86%, 2, 20h, 99%, 3, 19h, 100%; (viii) CF₃CO₂H, CH₂Cl₂, rt, 6.5h, 4, 96%, 5, 3.5h, 100%.

In contrast to most peptide bonds that adopt exclusively the trans conformation, the amide bond between Xaa-Pro can exist as a mixture of cis and trans isomers (Dugave et al. *Chem. Rev.* 2003, 103, 2475). The nature of the conformation about this bond can affect the biological activity of a peptide and there is evidence that some proteases only recognize the trans peptide bond (Vanhoof et al. *FASEB J* 1995, 9, 736; Lin et al. *Biochemistry* 1983, 22, 4480). The existence of specific peptidyl-prolyl cis-trans isomerases would seem to corroborate this evidence (Fanghanel *Angew. Chem. Int. Ed.* 2003, 42, 490). GPE is present as a 20:80 cis-trans mixture of isomers in $D_2O$ solution as established by NMR analysis. When an alkyl group is substituted at the 2-position of proline the trans conformation is preferred. Compounds 1-4 adopt the all trans conformation and the trans population also increased in compound 5 with only 10% adopting the cis conformation. The prevalence of the trans isomer in 2-methylproline compounds has been attributed to the bulky methyl group destabilizing the cis conformation (Delaney et al. *J. Am. Chem. Soc.* 1982, 104, 6635).

Another method of conformationally constraining a peptide is to synthesize a peptidomimetic containing a spirolactam ring system. It has been suggested that a spirolactam ring system may lock a compound into predominantly one conformation and different ring systems have been shown to mimic both b- and g-turns (Hinds et al *J. Med. Chem.* 1991, 43, 1777; Fernandez et al. *J. Org. Chem.* 2002, 67, 7587; Kang *J. Phys. Chem.* 2002, 106, 2074). A spirocyclic g-lactam bridge can be formed between the 2-position of the proline residue and the nitrogen of the glutamate residue in GPE thus, presenting an opportunity to investigate the effect of such conformational restriction in GPE analogs.

The synthesis of GP-[5.5]spirolactamE 35 and the corresponding GP-[5.5]hydroxyspirolactamE 36 is summarized in Scheme 3.

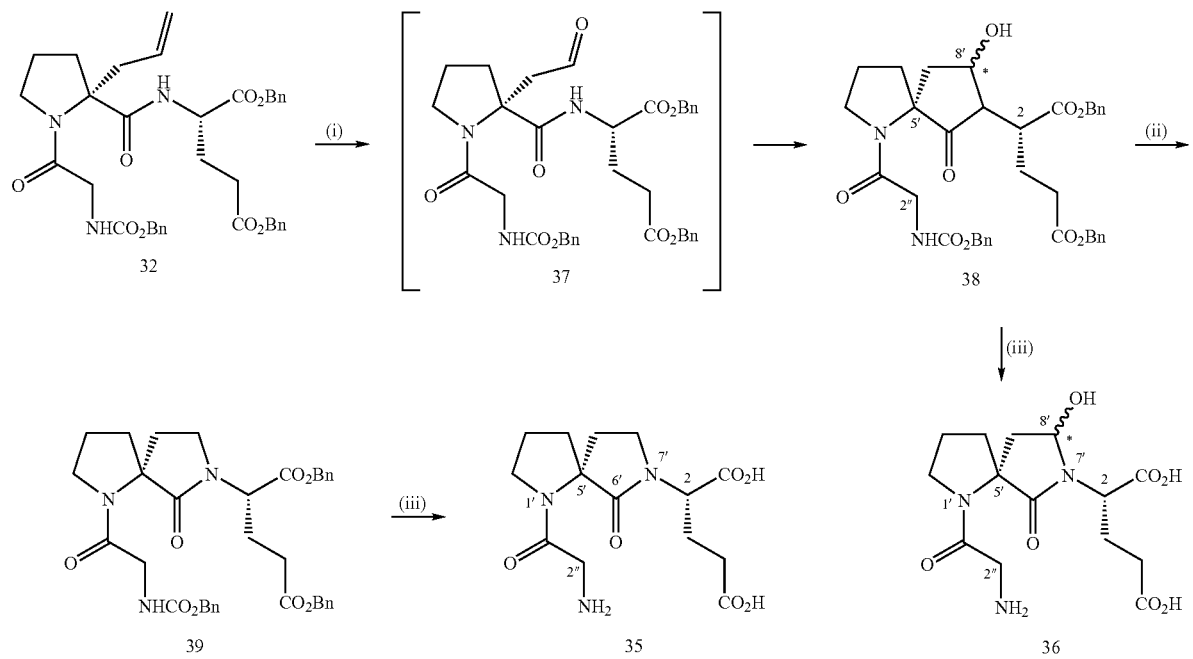

Reagents, conditions and yields: (i) O₃, MeOH/CH₂Cl₂ (1:1), 15 min then PPh₃, 24h, then silica gel, 63%; (ii) CF₃CO₂H/Et₃SiH/CH₂Cl₂ (1:1:1), rt, 45 min, 96%; (iii) 10% Pd/C, CH₃OH/H₂O (88:12), 18h, 35, 78%, 36, 99%.

Ozonolysis of alkene 32 followed by treatment with triphenylphosphine proceeded via the intermediacy of aldehyde 37 to give alcohols 38 as a 1:1 mixture of diastereoisomers. Direct hydrogenation of 38 gave the hydroxyspirolactam 36 whereas initial reduction of the hydroxyl group (trifluoroacetic acid-triethylsilane-dichloromethane) to 39 before the hydrogenolysis step afforded spirolactam 35. Both spirolactams adopted exclusively the trans conformation about the proline ring.

The pyrrolidine ring of proline is capable of adopting two distinct conformations. These down- and up-puckered conformations are defined as occurring when $C^g$ and the carbonyl group of proline lie on the same and opposite sides respectively, of the plane defined by $C^d$, N and $C^a$. The presence of a sulfur atom in the proline ring can affect the bond angles and bond lengths, in some cases altering the proline ring conformation. Kang found that replacement of the proline residue in AcProNHMe with 4-thiaproline 40 [(R)-thiozolidine-4-carboxylic acid (Thz)] resulted in a more puckered conformation (Kang 2002). Further conformational changes in the proline ring can be promoted by the addition of methyl groups at the 5 position of proline or Thz. The next set of analogs incorporated such pseudo-proline moieties where the g-$CH_2$ of Pro was replaced with sulfur and/or with dimethyl substitution at $C^d$.

The pseudo-prolines: 4-thiaproline 40 [(R)-thiozolidine-4-carboxylic acid (Thz)] and 2,2-dimethylthiazolidine-4-carboxylic acid 41 were easily accessed by the reaction of cysteine 42 with formaldehyde (Pellegrini et al. *Chem. Pharm. Bull.* 1999, 47, 950) or 2,2-dimethoxypropane (Lewis et al. *J. Med. Chem.* 1978, 21, 1071; Kemp et al. *J. Org. Chem.* 1989, 54, 3640), respectively (Scheme 4).

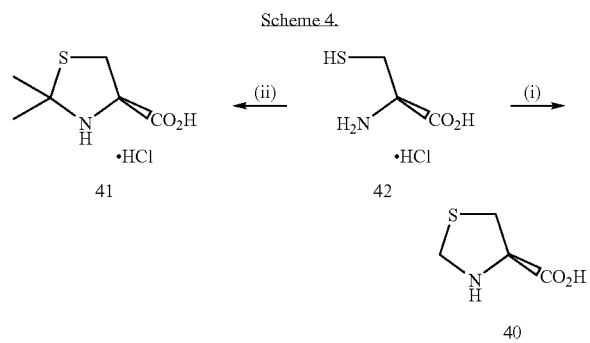

Reagents, conditions and yields: (i) 37% aq. HCHO, H₂O, rt, 22h, then pyridine, 56%; (ii) dimethoxypropane, acetone, reflux, 2h, 58%.

Boc-protected methyl D,L-5,5-dimethylprolinate 43 was prepared from nitrile 44 (Scheme 5). Nitrile 44 was prepared as described in the literature (Ono et al. *J. Org. Chem.*, 1985, 50 3692) however, subsequent hydrolysis of the nitrile moiety and hydrogenation of the intermediate N-oxide as described (Magaard et al. *Tetrahedron Lett.* 1993, 34, 381) was concomitant with acid catalysed methyl migration yielding a mixture of 45 and 46. (6:4 ratio, ¹H NMR). Extensive modification of the hydrolysis reaction could not overcome the formation of N-methyl compound 45. It is interesting that this unwanted reaction has not been reported during the synthesis of 5,5-dimethylproline that has been described by several research groups (An et al. *J. Am. Chem. Soc.* 1999, 121, 11588).

Protection of both the acid and amine functionalities as a methyl ester and a tert-butyloxy carbamate (Boc) respectively, allowed facile separation and characterisation of the protected 5,5-dimethylproline 43 (22% yield over 4 steps) and the N-methyl by-product 47 (42% yield, over 4 steps). The desired protected 5,5-dimethylproline 43 existed as a mixture of epimers (55:45) exclusively as the cis conformer.

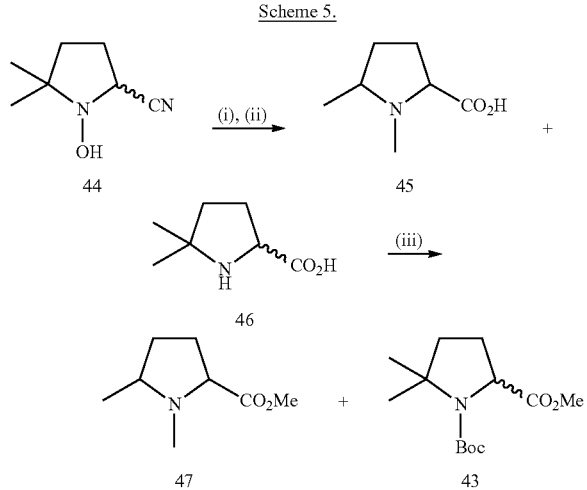

Scheme 5.

Reagents, conditions and yields: (i) 32% aqueous HCl, 50° C., 5h; (ii) $H_2$ (44 psi), 10% Pd/C, MeOH/$H_2O$ (1:1), 20h; (iii) $SOCl_2$, MeOH, 0° C. to rt, overnight then $Boc_2O$, N-methylmorpholine, $CH_2Cl_2$, reflux, 48h [43 (22%) 47 (42%)] over 4 steps.

The tripeptides 48-50 were synthesized in a similar fashion to the 2-alkylproline analogs (Scheme 6). Coupling of the 4-thia-proline building block 40 to Boc-glycine 17 was carried out using a mixed anhydride activation procedure whereas the more hindered 5,5-dimethyl-4-thia-proline 41 required use of the more reactive acid fluoride 51 to afford 53. In the case of the 5,5-dimethylproline 43 the Boc group was removed with trifluoroacetic acid before BoPCl coupling with Boc-glycine 17 to afford 54. Hydrolysis of the methyl ester then afforded acid 55 in preparation for the second peptide coupling.

Coupling of the pseudo dipeptides 52, 53 and 55 with either dibenzyl glutamate 28 or di-tert-butyl glutamate 29 using either a mixed anhydride protocol or BoPCl gave the desired peptides 56, 57 and 58. The nature of the final deprotection step depended on the protecting groups employed in the synthesis thus, for 57 removal of the benzyloxycarbonyl and benzyl groups by hydrogenolysis provided tripeptide 49. The Boc and tert-butyl ester groups in 56 were removed using trifluoroacetic acid to give tripeptide 48 as the trifluoroacetate salt whereas for the deprotection of 58, treatment with trifluoroacetic acid followed by hydrogenolysis afforded tripeptide 50.

The presence of a sulphur atom at C-4 in the pyrrolidine ring of proline, by itself did not appear to significantly alter the conformation of the peptide about the Gly-Pro bond. In the GPE analog 48 the cis:trans ratio was established to be 20:80, unchanged from the native peptide. The presence of the two methyl groups at C-5 had a more dramatic influence on the conformation with the cis:trans ratio dramatically shifted to favour the cis conformer. The population of the cis conformer in 5,5-dimethylated peptide 50 increased to 72% compared with the 20% seen with GPE. An even greater effect was observed with analog 49 which exhibited a 85:15 cis:trans ratio indicating that the presence of a sulphur atom at C-4 in combination with two methyl groups at C-5 in the proline ring plays a key role in determining the ratio of cis:trans isomers about the Gly-Pro bond. The high population of the cis conformer in related 5,5-dimethylprolines has been attributed to the effects of steric hindrance due to the methyl groups when the compound adopts the trans conformation.

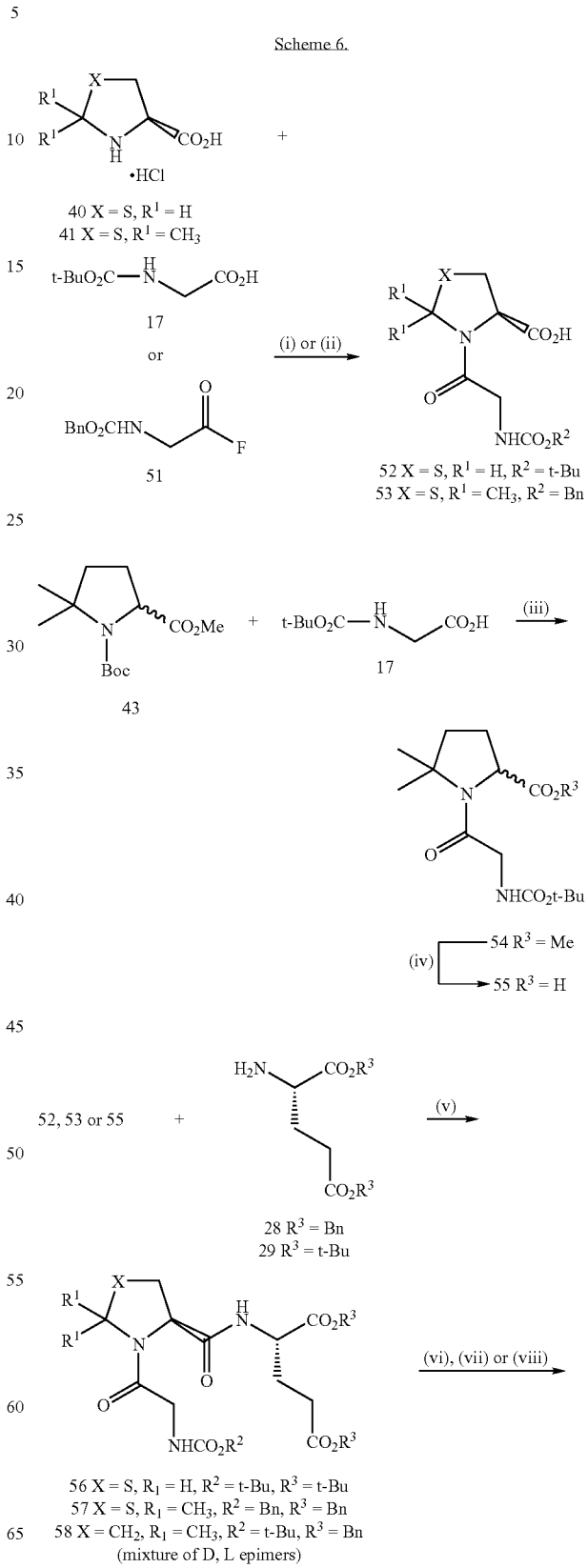

Scheme 6.

-continued

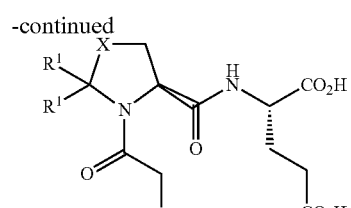

48 X = S, R₁ = H cis:trans 20:80
49 X = S, R₁ = CH₃ cis:trans 85:15
50 X = CH₂, R₁ = CH₃ cis:trans 72:28
(mixture of D, L epimers)

Reagents, conditions and yields: (i) 17, i-BuOCOCl, Et₃N, THF, 0° C. to rt, then 40, Et₃N, H₂O, rt, 2h, 52, 81%; (ii) 51, 41, i-Pr₂EtN, DMF, rt, 18h then MeOH, Me₃SiCl, rt, 15h, 53, 65%; (iii) 43, CF₃CO₂H, CH₂Cl₂, rt, 2h then 17, BoPCl, i-Pr₂EtN, CH₂Cl₂, rt, 15h, 54, 52%; (iv) dioxane, 1 M aq. NaOH, rt, 21h, 55, 94%; (v) for 56: EtOCOCl, Et₃N, CH₂Cl₂, 0° C., 35 min then 29, Et₃N, CH₂Cl₂, 0° C. to rt, 15h, 56, 54%; for 57, 58: BoPCl, i-Pr₂EtN, CH₂Cl₂, 28, rt, 7h, 57, 68%, 58, 24h, 67%; (vi) CF₃CO₂H, Et₃SiH, CH₂Cl₂, rt, 4h, 48, 61%; (vii) H₂(42 psi), 10% Pd/C, CH₃OH/H₂O (80:20), 24h, 49, 48%; (viii) CF₃CO₂H, CH₂Cl₂, rt, 75 min then H₂, 10% Pd/C, CH₃OH/H₂O (80:20), 15h, 50, 93%.

1.1. General Details

All reactions were conducted in flame-dried or oven-dried glassware under a dry nitrogen atmosphere unless otherwise noted. All reagents were used as supplied. Tetrahydrofuran was dried over sodium/benzophenone and distilled prior to use. Flash chromatography was performed using Merck Kieselgel 60 (230-400 mesh) with the indicated solvents. Thin layer chromatography (TLC) was carried out on precoated silica plates (Merck Kieselgel 60F$_{254}$) and compounds were visualized by UV fluorescence and heating of plates dipped in anisaldehyde in ethanolic sulphuric acid or alkaline potassium permanganate solution. Melting points in degrees Celsius (° C.) were measured on an Electrothermal® melting point apparatus and are uncorrected. Infrared spectra were recorded with a Perkin Elmer 1600 series Fourier-transform infrared spectrometer as thin films between sodium chloride plates. Absorption maxima are expressed in wavenumbers (cm$^{-1}$) with the following abbreviations: s=strong, m=medium, w=weak and br=broad Nuclear Magnetic Resonance (NMR) spectra were recorded on a Bruker AVANCE DRX400 ($^1$H, 400 MHz; $^{13}$C, 100 MHz), a Bruker AVANCE 300 ($^1$H, 300 MHz; $^{13}$C, 75 MHz) or a Bruker AC200 ($^1$H, 200 MHz; $^{13}$C, 50 MHz) spectrometer at 298 K. For $^1$H NMR data, chemical shifts are described in parts per million (ppm) relative to tetramethylsilane (δ 0.00), DOH (δ 4.75), CHD₂OD ((δ 3.30) or CHD₂S(O)CD₃ (δ 2.50) and are reported consecutively as position (δ$_H$), relative integral, multiplicity (s=singlet, d=doublet, t=triplet, q=quartet, p=pentet, q=quintet, s=sextet, dd=doublet of doublets, m=multiplet, and where br=broad), coupling constant (J/Hz) and assignment. For $^{13}$C NMR data, chemical shifts (ppm) are referenced internally to CDCl₃ (δ 77.0), CD₃OD (δ 49.1) and (CD₃)₂S(O) (δ 39.4) or externally to 3-(trimethylsilyl)-1-propanesulfonic acid sodium salt (DSS) and are reported consecutively as position (δ$_C$), degree of hybridisation and assignment. The asterisk* denotes resonances assigned to the minor conformer. High resolution mass spectra were recorded using a VG70-SE spectrometer operating at nominal accelerating voltage of 70 eV. Chemical ionisation (CI) mass spectra were obtained with ammonia as the reagent gas. Optical rotations were measured at 20° C. on a Perkin Elmer 341 polarimeter using 10 cm path length cells and are given in units of 10$^{-1}$ degcm$^2$ g$^{-1}$. Samples were prepared in the solvent indicated at the concentration specified (measured in g/100 cm$^3$).

1.1.1. (2R,5S)-2-Trichloromethyl-1-aza-3-oxabicyclo[3.3.0]octan-4-one 7

A suspension of L-proline (10.0 g, 86.8 mmol) and chloral hydrate (21.6 g, 130 mmol) were heated under reflux in chloroform (100 cm$^3$) for 6 h with a reverse Dean-Stark trap. The solution was washed with water (2×30 cm$^3$) and the water washings were extracted with chloroform (50 cm$^3$). The combined organic layers were dried (MgSO₄), filtered and the solvent removed in vacuo to afford a light brown solid (19.8 g). The crude product was recrystallised from ethanol (80 cm$^3$) at 40° C. to form oxazolidinone 7 (16.1 g, 77%) as a white solid: mp 107-109° C. (lit. Amedjkouh et al. *Tetrahedron. Asymmetry* 2002, 13, 2229) ethanol, 107.6° C.); [α]$_D$ +34.2 (c 2 in C₆H₆), (lit. Wang *Synlett* 1999, 1, 33) [α]$_D$ +33 (c 2.0 in C₆H₆): $^{TM}_H$ (200 MHz; CDCl₃) 1.67-2.29 (4H, m, Proβ-H₂ and Proγ-H₂), 3.08-3.20 (1H, m, Proβ-H$_A$H$_B$), 3.37-3.49 (1H, m, Proβ-H$_A$H$_B$), 4.09-4.15 (1H, m, Proα-H) and 5.17 (1H, s, NCH); $^{TM}_C$ (50 MHz; CDCl₃) 25.3 (CH₂, Proγ-C), 29.9 (CH₂, Proγ-C), 57.9 (CH₂, Proδ-C), 62.4 (CH, Proα-C), 100.6 [quat., C(Cl₃)], 103.6 (CH, NCH) and 175.5 (quat., CO); m/z (EI+) 244 (MH⁺ 244).

1.1.2. (2R,5S)-5-Methyl-2-trichloromethyl-1-aza-3-oxabicyclo[3.3.0]octan-4-one 8 n-Butyllithium (1.31 M, 4.68 cm$^3$, 6.14 mmol) was added dropwise to a stirred solution of diisopropylamine (0.86 cm$^3$, 6.14 mmol) in dry tetrahydrofuran (10 cm$^3$) at −78° C. under an atmosphere of nitrogen. The solution was stirred for 5 min, warmed to 0° C. and stirred for 15 min. The solution was added dropwise to a solution of oxazolidinone 7 (1.00 g, 4.09 mmol) in dry tetrahydrofuran (20 cm$^3$) at −78° C. over 20 min (reaction mixture turned dark), stirred for a further 30 min then iodomethane (0.76 cm$^3$, 12.3 mmol) added dropwise over 5 min. The solution was warmed to −50° C. over 2 h. Water (15 cm$^3$) was added, the solution warmed to room temperature and extracted with chloroform (3×40 cm$^3$). The combined organic extracts were dried (MgSO₄), filtered and evaporated to dryness in vacuo to give a dark brown semisolid. Purification of the residue by flash column chromatography (15% ethyl acetate-hexane) afforded oxazolidinone 8 (0.67 g, 63%) as a pale yellow solid: mp 55-57° C. (lit. Wang 57-60° C.): δ$_H$ (300 MHz; CDCl₃) 1.53 (3H, s, CH₃), 1.72-2.02 (3H, m, Proβ-H and Proγ-H₂), 2.18-2.26 (1H, m, Proβ-H), 3.15-3.22 (1H, m, Proδ-H), 3.35-3.44 (1H, m, Proδ-H) and 4.99 (1H, s, NCH).

1.1.3. (2R,5S)-5-Ethyl-2-trichloromethyl-1-aza-3-oxabicyclo[3.3.0]octan-4-one 9

The reaction was carried out following a similar procedure to that described for the preparation of oxazolidinone 8 using n-butyllithium (1.31 M, 28.3 cm$^3$, 37.1 mmol), diisopropylamine (5.2 cm$^3$, 37.1 mmol), oxazolidinone 7 (6.0 g, 24.7 mmol) and iodoethane (5.9 cm$^3$, 73.8 mmol) to afford oxazolidinone 9 (3.05 g, 46%) as a light red oil that solidified on standing to a pale brown solid: mp 76-77° C.: [α]$_D$ +18.5 (c 0.25 in CHCl₃): δ$_H$ (300 MHz; CDCl₃) 1.04 (3 H, t, J 7.5, CH₃), 1.60-1.80 (1H, m, CH$_A$H$_B$CH₃), 1.72-1.99 (4H, m, CH$_A$H$_B$CH₃, Proβ-H$_A$H$_B$ and Proγ-H₂), 2.20-2.30 (1H, m, Proβ-H$_A$H$_B$), 3.22-3.29 (2H, m, Proδ-H₂) and 5.00 (1 H, s, NCH); δ$_C$ (75 MHz; CDCl₃) 8.4 (CH₃, CH₃), 25.5 (CH₂, CH$_2$CH$_3$), 30.9 (CH$_2$, Proγ-C), 35.6 (CH$_2$, Proβ-C), 58.6 (CH$_2$, Proδ-C), 72.5 (quat., Proα-C), 100.9 [quat., C(Cl$_3$)], 102.5 (CH, NCH) and 176.9 (quat., CO); m/z (EI+) 272.0014 (MH$^+$.C$_9$H$_{13}$$^{35}$ClN$_3$O$_2$ requires 272.0012).

1.1.4. (2R,5R)-5-Allyl-2-trichloromethyl-1-aza-3-oxabicyclo[3.3.0]octan-4-one 10

(Wang et al. *Synlett* 1999, 1, 33) The reaction was carried out following a similar procedure to that described for the preparation of oxazolidinone 8 using n-butyllithium (1.31 M, 9.93 cm$^3$, 13.0 mmol), diisopropylamine (1.82 cm$^3$, 13.0 mmol), oxazolidinone 7 (2.10 g, 8.7 mmol) and allyl bromide (2.25 cm$^3$, 26.0 mmol) to afford oxazolidinone 10 (1.48 g, 60%) as a light orange oil for which the NMR data were in agreement with the literature.

1.1.5. (2R,5R)-5-Benzyl-2-trichloromethyl-1-aza-3-oxabicyclo[3.3.0]octan-4-one 11

(Wang et al. *Synlett* 1999, 1, 33). The reaction was carried out following a similar procedure to that described for the preparation of oxazolidinone 8 using n-butyllithium (1.31 M, 5.53 cm$^3$, 7.2 mmol), diisopropylamine (1.01 cm$^3$, 7.24 mmol), oxazolidinone 7 (1.18 g, 4.8 mmol) and benzyl bromide (1.72 cm$^3$, 14.5 mmol) to afford oxazolidinone 11 (0.52 g, 32%) as a colourless crystalline solid: mp 75-77° C. (lit. Wang 72-77): δ$_H$ (400 MHz; CDCl$_3$) 1.32-1.55 (2H, m, Proγ-H$_2$), 1.93-2.13 (2H, m, Proβ-H$_2$), 2.58-2.65 (1H, m, Proδ-H$_2$), 2.92 (1H, d, J 13.6, PhCH$_A$H$_B$), 2.98-3.03 (1H, m, Proδ-H$_2$), 3.32 (1H, d, J 13.6, PhCH$_A$H$_B$), 4.99 (1H, s, NCH) and 7.21-7.35 (5H, m, PhH); δ$_C$ (100 MHz; CDCl$_3$) 24.8 (CH$_2$, Proγ-C), 34.6 (CH$_2$, Proβ-C), 41.6 (CH$_2$, Proδ-C), 58.4 (CH$_2$, PhCH$_2$), 72.3 (quat., Proα-C), 100.6 (quat., CCl$_3$), 102.8 (CH, NCH), 127.0 (CH, Ph), 128.2 (CH, Ph), 130.9 (CH, Ph), 135.5 (quat., Ph) and 176.6 (quat., C=O); m/z (EI+) 333.0081 [(M+H)$^+$.C$_{14}$H$_{14}$$^{35}$Cl$_3$NO$_2$ requires 333.0090], 335.0069 [(M+H)$^+$.C$_{14}$H$_{14}$$^{35}$Cl$_2$$^{37}$ClNO$_2$ requires 335.0061], 337.0014 [(M+H)$^+$.C$_{14}$H$_{14}$$^{35}$Cl$^{37}$Cl$_2$NO$_2$ requires 337.0031] and 339.0009 [(M+H)$^+$.C$_{14}$H$_{14}$$^{37}$Cl$_3$NO$_2$ requires 339.0002].

1.1.6. Methyl L-2-methylprolinate hydrochloride 12

Thionyl chloride (4.30 mL, 58.9 mmol) was added dropwise cautiously to a stirred solution of 8 (7.57 g, 29.4 mmol) at 0° C. under a nitrogen atmosphere. The cooling bath was removed and mixture stirred at room temperature for 20 mins then heated to reflux for 3 h. The volatiles were removed in vacuo, the residue suspended in toluene (20 mL) and concentrated at 50° C. to remove traces of thionyl chloride. Trituration with dry ether yielded a brown solid. The yellow/orange ether was decanted and the solid was shaken with dry ether, decanted and the procedure repeated until the ether was colourless. Removal of traces of ether in vacuo at 50° C. afforded 12 (ca. 5.0 g, 100%) as a free flowing, hygroscopic brown solid that was used without any further purification: mp 107-109° C. (lit. (Lewis et al. *J. Chem. Soc. Perkin Trans.* 1 1998, 3777) 106-108° C.).

1.1.7. Methyl L-2-ethylprolinate hydrochloride 13

An ice-cooled solution of oxazolidinone 9 (2.86 g, 10.0 mmol) in dry methanol (35 cm$^3$) under an atmosphere of nitrogen was treated dropwise with a solution of thionyl chloride (2.3 cm$^3$, 31.5 mmol). The solution was heated under reflux for 3 h., cooled and the solvent removed under reduced pressure. The resultant brown oil was purified by flash column chromatography (10% methanol/dichloromethane) to afford hydrochloride 13 (1.45 g, 71%) as a light brown semi-solid: [α]$_D$ −61.1(c 0.3 in CHCl$_3$): δ$_H$ (300 MHz; CDCl$_3$) 1.07 (3H, t, J 7.3, CH$_3$), 1.95-2.33 (5H, m, CH$_2$CH$_3$, Proγ-H$_2$ and Proβ-H$_A$H$_B$), 2.43-2.47 (1 H, Proβ-H$_A$H$_B$), 3.63 (3 H, s, OCH$_3$) and 6.98-7.35 (2H, br s, NH$_2$); δ$_C$ (75 MHz; CDCl$_3$) 9.9 (CH$_3$, CH$_3$), 22.8 (CH$_2$, CH$_2$CH$_3$), 28.9 (CH$_2$, Proγ-C), 35.1 (CH$_2$, Proβ-C), 45.7 (CH$_2$, Proδ-C), 53.8 (CH$_3$, OCH$_3$), 73.9 (quat., Proα-C) and 171.0 (quat., CO). m/z (EI+) 158.1181 (MH$^+$.C$_8$H$_{16}$NO$_2$ requires 158.1181).

1.1.8. Methyl L-2-allylprolinate hydrochloride 14

(Wang et al. *Synlett* 1999, 1, 33, Hoffmann et al. *Angew. Chem. Int. Ed. Engl.* 2001, 40, 3361). An ice-cooled solution of oxazolidinone 10 (0.64 g, 2.24 mmol) in dry methanol (15 cm$^3$) was treated dropwise with a solution of acetyl chloride (0.36 cm$^3$, 5.0 mmol) in methanol (5 cm$^3$). The solution was heated under reflux for 24 h, cooled and the solvent removed under reduced pressure. The resultant brown oil was dissolved in toluene (40 cm$^3$) and concentrated to dryness to remove residual thionyl chloride and methanol, then purified by flash column chromatography (5-10% CH$_3$OH—CH$_2$Cl$_2$; gradient elution) to afford hydrochloride 14 (0.29 g, 63%) as a solid for which the NMR data were in agreement with that reported in the literature. δ$_H$ (300 MHz, CDCl$_3$) 1.72-2.25 (3H, m, Proβ-H$_A$H$_B$ and Proγ-H$_2$), 2.32-2.52 (1H, m, Proβ-H$_A$H$_B$), 2.72-3.10 (2H, m, Proδ-H$_2$), 3.31-3.78 (2H, m, CH$_2$CH=CH$_2$), 3.84 (3H, s, CO$_2$CH$_3$), 5.20-5.33 (2H, m, CH=CH$_2$), 5.75-5.98 (1H, m, CH=CH$_2$) and 8.06 (1H, br s, N—H); m/z (CI+) 170.1183 [(M+H)$^+$.C$_9$H$_{16}$NO$_2$ requires 170.1181].

1.1.9. Methyl L-2-benzylprolinate hydrochloride 15

(Yasuo et al. *Chem. Pharm. Bull.* 1979, 27, 1931) An ice-cooled solution of oxazolidinone 11 (1.03 g, 3.07 mmol) in dry methanol (10 cm$^3$) was treated dropwise with a solution of acetyl chloride (0.71 cm$^3$, 10.0 mmol) in methanol (10 cm$^3$). The solution was heated under reflux for 24 h, cooled and the solvents removed under reduced pressure. The resultant brown oil was dissolved in toluene (80 cm$^3$), concentrated to dryness to remove residual thionyl chloride and methanol, then purified by flash column chromatography (5% CH$_3$OH—CH$_2$Cl$_2$) to afford hydrochloride 15 (0.38 g, 48%) as a beige solid: δ$_H$ (400 MHz; D$_2$O) 1.92-2.01 (1H, m, Proγ-H$_A$H$_B$), 2.11-2.23 (2H, m, Proβ-H$_A$H$_B$ and Proγ-H$_A$H$_B$), 2.52-2.60 (1H, m, Proβ-H$_A$H$_B$), 3.19 (1H, d, J 14.3, PhCH$_A$H$_B$), 3.24-3.31 (1H, m, Pro$^δ$-H$_A$H$_B$), 3.37-3.43 (1H, m, Proδ-H$_A$H$_B$), 3.53 (1H, d, J 14.3, PhCH$_A$H$_B$), 3.83 (3H, s, CO$_2$CH$_3$) and 7.26-7.47 (5H, m, PhH); δ$_C$ (100 MHz; D$_2$O) 24.4 (CH$_2$, Proγ-C), 36.8 (CH$_2$, Proβ-C), 43.8 (CH$_2$, PhCH$_2$), 47.6 (CH$_2$, Proδ-C), 56.0 (CH$_3$, OCH$_3$), 75.9 (quat., Proα-C), 130.4 (CH, Ph), 131.5 (CH, Ph), 131.7 (CH, Ph), 137.1 (quat., Ph) and 175.8 (quat., C=O); m/z (CI+) 220.1340 [(M+H)$^+$.C$_{13}$H$_{18}$NO$_2$ requires 220.1338].

1.1.10. Methyl N-benzyloxycarbonyl-glycyl-L-2-methylprolinate 18

Dry triethylamine (0.27 cm$^3$, 1.96 mmol) was added dropwise to a solution of hydrochloride 12 (0.11 g, 0.61 mmol) and N-benzyloxycarbonylglycine 16 (0.17 g, 0.79 mmol) in dry dichloromethane (35 cm$^3$) under an atmosphere of nitrogen at room temperature and the reaction mixture stirred for 10 min. Bis(2-oxo-3-oxazolidinyl)phosphinic chloride (0.196 g, 0.77 mmol) was added and the resultant colourless solution was stirred for 20.5 h. The solution was washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (δ0-80% ethyl acetate-hexane; gradient elution) yielded ester 18 (0.18 g, 92%) as a colourless oil: [α]$_D$ –33.0 (c 1.0 in MeOH); ν$_{max}$ (film)/cm$^{-1}$ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; δ$_H$ (300 MHz, CDCl$_3$) 1.49 (3H, s, CH$_3$), 1.77-2.11 (4H, m, Proβ-H$_2$ and Proγ-H$_2$), 3.43-3.48 (2H, m, Proδ-H$_2$), 3.61 (3H, s, OCH$_3$), 3.85-3.89 (2H, m, Glyα-H$_2$), 5.04 (2H, s, PhCH$_2$), 5.76 (1H, br s, N—H) and 7.21-7.28 (5H, s, ArH); δ$_C$ (75 MHz, CDCl$_3$), 21.1 (CH$_3$, Proα-CH$_3$), 23.5 (CH$_2$, Proγ-C), 38.0 (CH$_2$, Proβ-C), 43.3 (CH$_2$, Glyα-C), 46.6 (CH$_2$, Proδ-C), 52.1 (CH$_3$, OCH$_3$), 66.0 (quat., Proα-C), 66.3 (CH$_2$, PhCH$_2$), 127.5 (CH, Ph), 127.6 (CH, Ph), 128.1 (CH, Ph), 136.2 (quat., Ph), 155.9 (quat., NCO$_2$), 166.0 (quat., Gly-CON) and 173.6 (quat., CO$_2$CH$_3$); m/z (EI+) 334.1535 (M$^+$.C$_{17}$H$_{22}$N$_2$O$_5$ requires 334.1529).

1.1.11. Methyl N-benzyloxycarbonyl-glycyl-L-2-ethylprolinate 19

Dry triethylamine (2.88 cm$^3$, 20.7 mmol) was added dropwise to a solution of hydrochloride 13 (1.14 g, 5.9 mmol) and N-benzyloxycarbonylglycine 16 (2.47 g, 11.8 mmol) in dry dichloromethane (100 cm$^3$) under an atmosphere of nitrogen at 0° C., and the reaction mixture stirred for 10 min. Bis(2-oxo-3-oxazolidinyl)phosphinic chloride (3.00 g, 11.8 mmol) was added and the solution was stirred for 2 h, warmed to room temperature and further stirred for 17.5 h. Dichloromethane (50 cm$^3$) was added and the solution washed successively with 0.5 M aqueous hydrochloric acid (2×50 cm$^3$) and saturated aqueous sodium hydrogen carbonate (2×50 cm$^3$), dried (MgSO$_4$), filtered and evaporated in vacuo to give a light orange gum. Purification of the resultant residue by flash column chromatography (40% ethyl acetate/hexane) yielded ester 19 (0.95 g, 46%) as a clear oil: [α]$_D$ –9.2 (c 0.13 in CHCl$_3$); δ$_H$ (300 MHz; CDCl$_3$) 0.81 (3 H, t, J 7.5, CH$_3$), 1.85-2.09 (5 H, m, CH$_2$CH$_3$, Proγ-H$_2$ and Proβ-H$_A$H$_B$), 2.38 (1 H, sextet, J 7.5, Proβ-H$_A$H$_B$), 3.43-3.47 (1 H, m, Proδ-H$_A$H$_B$), 3.61-3.67 (1 H, m, Proδ-H$_A$H$_B$), 3.70 (3H, s, OCH$_3$), 4.10-4.13 (2 H, m, Glyα-H$_2$) 5.11 (2 H, s, OCH$_2$Ph), 5.71 (1 H, br s, Gly-NH) and 7.27-7.35 (5 H, m, Ph); δ$_C$ (75 MHz; CDCl$_3$) 8.3 (CH$_3$, CH$_3$), 24.1 (CH$_2$, CH$_2$CH$_3$), 26.5 (CH$_2$, Proγ-C), 35.3 (CH$_2$, Proβ-C), 44.1 (CH$_2$, Glyα-C), 48.2 (CH$_2$, Proδ-C), 52.9 (CH$_3$, OCH$_3$), 67.0 (CH$_2$, OCH$_2$Ph), 70.2 (quat., Proα-C), 128.2 (CH, Ph), 128.3 (CH, Ph), 128.7 (CH, Ph), 136.8 (quat., Ph), 156.5 (quat., NCO), 166.8 (quat., Gly-CON) and 174.5 (quat., CO$_2$CH$_3$); m/z (EI+) 348.1688 (MH$^+$.C$_{18}$H$_{24}$N$_2$O$_5$ requires 348.1685).

1.1.12. Methyl N-benzyloxycarbonyl-glycyl-L-2-allylprolinate 20

Dry triethylamine (1.07 cm$^3$, 7.70 mmol) was added dropwise to a solution of hydrochloride 14 (0.50 g, 2.41 mmol) and N-benzyloxycarbonyl-glycine 16 (0.65 g, 3.13 mmol) in dry dichloromethane (80 cm$^3$) under an atmosphere of nitrogen at room temperature, and the reaction mixture stirred for 10 min. Bis(2-oxo-3-oxazolidinyl)phosphinic chloride (0.772 g, 3.03 mmol) was added and the solution stirred for 20 h, then washed successively with 10% aqueous hydrochloric acid (80 cm$^3$) and saturated aqueous sodium hydrogen carbonate (80 cm$^3$), dried (MgSO$_4$), filtered and evaporated to dryness in vacuo. Purification of the resultant residue by flash column chromatography (60% ethyl acetate-hexane, 7 drops of Et$_3$N for every 200 cm$^3$) yielded ester 20 (0.26 g, 30%) as a yellow oil: [α]$_D$ +46.0 (c 0.50 in CH$_2$Cl$_2$); ν$_{max}$ (film)/cm$^{-1}$ 3405, 3066, 3032, 2953, 2877, 1723, 1655, 1586, 1507, 1434, 1373, 1333, 1309, 1248, 1169, 1121, 1083, 1047, 1027, 1002, 919, 866, 827, 776, 737 and 699; (300 MHz; CDCl$_3$) 1.92-2.17 (4H, m, Proβ-H$_2$ and Proγ-H$_2$), 2.60-2.67 (1H, m, CH$_A$H$_B$CH=CH$_2$), 3.09-3.16 (1H, m, CH$_A$H$_B$CH=CH$_2$), 3.35-3.42 (1H, m, Proδ-H$_A$H$_B$), 3.56-3.63 (1H, m, Proδ-H$_A$H$_B$), 3.70 (3H, s, OCH$_3$), 3.96 (2H, d, J 4.4, Glyα-H$_2$), 5.07-5.12 (4H, m, PhCH$_2$ and CH=CH$_2$), 5.58-5.70 (1H, m, CH=CH$_2$) and 7.27-7.35 (5H, s, PhH); δ$_C$ (75 MHz; CDCl$_3$) 23.6 (CH$_2$, Proγ-C), 34.9 (CH$_2$, Proβ-C), 37.6 (CH$_2$, CH$_2$CH=CH$_2$), 43.6 (CH$_2$, Glyα-C), 47.5 (CH$_2$, Proδ-C), 52.5 (CH$_3$, OCH$_3$), 66.7 (CH$_2$, PhCH$_2$), 68.8 (quat., Proα-C), 119.4 (CH$_2$, CH=CH$_2$), 127.9 (CH, Ph), 128.0 (CH, Ph), 128.4 (CH, Ph), 132.8 (CH, CH=CH$_2$), 136.4 (quat., Ph), 156.1 (quat., NCO$_2$), 166.4 (quat., Gly-CON) and 173.7 (quat., CO$_2$CH$_3$); m/z (EI+) 360.1682 (M$^+$.C$_{19}$H$_{24}$N$_2$O$_5$ requires 360.1685).

1.1.13. Methyl N-tert-butyloxycarbonyl-glycyl-L-2-allylprolinate 21

Dry triethylamine (0.28 cm$^3$, 2.02 mmol) was added dropwise to a solution of hydrochloride 14 (0.13 g, 0.63 mmol) and N-tert-butyloxycarbonylglycine 17 (0.14 g, 0.82 mmol) in dry dichloromethane (35 cm$^3$) under an atmosphere of nitrogen at room temperature, and the reaction mixture stirred for 10 min. Bis(2-oxo-3-oxazolidinyl)phosphinic chloride (0.20 g, 0.80 mmol) was added and the solution stirred for 19.5 h, then washed successively with 10% aqueous hydrochloric acid (35 cm$^3$) and saturated aqueous sodium hydrogen carbonate (35 cm$^3$), dried (MgSO$_4$), filtered and evaporated to dryness in vacuo. Purification of the resultant residue by flash column chromatography (40% ethyl acetate-hexane) yielded ester 21 (0.09 g, 45%) as a light yellow oil: [α]$_D$ +33.8 (c 0.83 in CH$_2$Cl$_2$); ν$_{max}$ (film)/cm$^{-1}$ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; δ$_H$ (300 MHz; CDCl$_3$) 1.42 [9H, s, C(CH$_3$)$_3$], 1.93-2.08 (4H, m, Proβ-H$_2$ and Proγ-H$_2$), 2.59-2.67 (1H, m, CH$_A$H$_B$CH=CH$_2$), 3.09-3.16 (1H, m, CH$_A$H$_B$CH=CH$_2$), 3.35-3.44 (1H, m, Proδ-H$_A$H$_B$), 3.56-3.62 (1H, m, Proδ-H$_A$H$_B$), 3.70 (3H, s, OCH$_3$), 3.89 (2H, d, J 4.2, Glyα-H$_2$), 5.06-5.11 (2H, m, CH=CH$_2$), 5.42 (1H, br s, Gly-NH) and 5.58-5.72 (1H, m, CH=CH$_2$); (δ$_C$ (75 MHz; CDCl$_3$) 23.7 (CH$_2$, Proγ-C), 28.3 [CH$_3$, C(CH$_3$)$_3$], 35.0 (CH$_2$, Proβ-C), 37.6 (CH$_2$, CH$_2$CH=CH$_2$), 43.3 (CH$_2$, Glyα-C), 47.5 (CH$_2$, Proδ-C), 52.5 (CH$_3$, OCH$_3$), 68.8 (quat., Proα-C), 79.5 [quat., C(CH$_3$)$_3$], 119.4 (CH$_2$, CH=CH$_2$), 132.9 (CH, CH=CH$_2$), 155.7 (quat., NCO$_2$), 166.9 (quat., Gly-CON) and 173.8 (quat., CO$_2$CH$_3$); m/z (EI+) 326.1845 (M$^+$.C$_{16}$H$_{26}$N$_2$O$_5$ requires 326.1842).

1.1.14. Methyl N-tert-Butyloxycarbonyl-glycyl-L-2-benzylprolinate 22

Dry triethylamine (0.59 cm$^3$, 4.22 mmol) was added dropwise to a solution of hydrochloride 15 (0.34 g, 1.32 mmol) and N-tert-butyloxycarbonylglycine 17 (0.30 g, 1.71 mmol) in dry dichloromethane (70 cm$^3$) under an atmosphere of nitrogen at room temperature, and the reaction mixture stirred for 10 min. Bis(2-oxo-3-oxazolidinyl)phosphinic chloride (0.42 g, 1.66 mmol) was added and the solution stirred for 18.5 h, then washed successively with 10% aqueous hydrochloric acid (70 cm$^3$) and saturated aqueous sodium hydrogen carbonate (70 cm$^3$), dried (MgSO$_4$), filtered and evaporated to dryness in vacuo. Purification of the resultant residue by flash column chromatography (50% ethyl acetate-hexane) yielded ester 22 (0.11 g, 22%) as a pale yellow oil: $[\alpha]_D$ +105.3 (c 0.99 in CH$_2$Cl$_2$); $v_{max}$ (film)/cm$^{-1}$ 3419, 3061, 3028, 2977, 2873, 1799, 1739, 1715, 1655, 1582, 1497, 1454, 1432, 1392, 1366, 1330, 1250, 1167, 1121, 1093, 1049, 1026, 948, 915, 865, 819, 765, 736, 706 and 653; $\delta_H$ (300 MHz; CDCl$_3$) 1.08-1.12 (1H, m, Proγ-H$_A$H$_B$), 1.47 [9H, s, C(CH$_3$)$_3$], 1.67-1.72 (1H, m, Proγ-H$_A$H$_B$), 2.01-2.17 (2H, m, Proβ-H$_2$), 2.86-2.92 (1H, m, Proδ-H$_A$H$_B$), 3.08 (1H, d, J 13.8, PhCH$_A$H$_B$), 3.36-3.42 (1H, m, Proδ-H$_A$H$_B$), 3.75 (3H, s, OCH$_3$), 3.83 (1H, m, PhCH$_A$H$_B$), 3.90 (2H, d, J 3.6, Glyα-CH$_2$), 5.54 (1H, br s, N—H) and 7.06-7.30 (5H, m, PhH); $\delta_C$ (100 MHz; CDCl$_3$) 23.4 (CH$_2$, Proγ-C), 28.4 [CH$_3$, C(CH$_3$)$_3$], 34.7 (CH$_2$, Proβ-C), 37.8 (CH$_2$, PhCH$_2$), 43.6 (CH$_2$, Glyα-C), 47.4 (CH$_2$, Proδ-C), 52.6 (CH$_3$, OCH$_3$), 69.6 (quat., Proα-C), 79.6 [quat., C(CH$_3$)$_3$], 126.8 (CH, Ph), 128.3 (CH, Ph), 130.5 (CH, Ph), 136.7 (quat., Ph), 155.8 (quat., NCO$_2$), 167.2 (quat., Gly-CON) and 174.0 (quat., CO$_2$CH$_3$); m/z (EI+) 376.2001 (M$^+$.C$_{20}$H$_{28}$N$_2$O$_5$ requires 376.1998).

1.1.15.
N-Benzyloxycarbonyl-glycyl-L-2-methylproline 23

To a solution of mthyl ester 18 (0.56 g, ca. 1.67 mmol) in 1,4-dioxane (33 cm$^3$) was added dropwise 1 M aqueous sodium hydroxide (10 cm$^3$, 10 mmol) and the mixture was stirred for 19 h at room temperature. Dichloromethane (100 cm$^3$) was then added and the organic layer extracted with saturated aqueous sodium hydrogen carbonate (2×100 cm$^3$). The combined aqueous layers were carefully acidified with dilute hydrochloric acid, extracted with dichloromethane (2×100 cm$^3$), and the combined organic layers dried (MgSO$_4$), filtered, and concentrated to dryness in vacuo. Purification of the ensuing residue (0.47 g) by flash column chromatography (50% ethyl acetate-hexane to 30% methanol-dichloromethane; gradient elution) gave acid 23 (0.68 g, 90%) as a white foam: $[\alpha]_D$ −62.3 (c 0.20 in CH$_2$Cl$_2$); $v_{max}$ (film)/cm$^{-1}$ 3583, 3324 br, 2980, 2942, 1722, 1649, 1529, 1454, 1432, 1373, 1337, 1251, 1219, 1179, 1053, 1027, 965, 912, 735 and 698; $\delta_H$ (300 MHz; CDCl$_3$) 1.59 (3H, s, Proα-CH$_3$), 1.89 (1H, 6 lines, J 18.8, 6.2 and 6.2, Proβ-H$_A$H$_B$), 2.01 (2H, dtt, J 18.7, 6.2 and 6.2, Proγ-H$_2$), 2.25-2.40 (1H, m, Proβ-H$_A$H$_B$), 3.54 (2H, t, J 6.6, Proδ-H$_2$), 3.89 (1H, dd, J 17.1 and 3.9, Glyα-H$_A$H$_B$), 4.04 (1H, dd, J 17.2 and 5.3, Glyα-H$_A$H$_B$), 5.11 (2H, s, OCH$_2$Ph), 5.84 (1H, br t, J 4.2, N—H), 7.22-7.43 (5H, m, Ph) and 7.89 (1H, br s, —COOH); $\delta_C$ (75 MHz; CDCl$_3$) 21.3 (CH$_3$, Proα-CH$_3$), 23.8 (CH$_2$, Proγ-C), 38.2 (CH$_2$, Proβ-C), 43.6 (CH$_2$, Glyα-C), 47.2 (CH$_2$, Proδ-C), 66.7 (quat, Proα-C), 66.8 (CH$_2$, OCH$_2$Ph), 127.9 (CH, Ph), 127.9 (CH, Ph), 128.4, (CH, Ph), 136.4 (quat., Ph), 156.4 (quat., NCO$_2$), 167.5 (quat., Gly-CON) and 176.7 (quat., CO); m/z (EI+) 320.1368 (M$^+$.C$_{16}$H$_{20}$N$_2$O$_5$ requires 320.1372).

1.1.16.
N-Benzyloxycarbonyl-glycyl-L-2-ethylproline 24

To a solution of methyl ester 19 (0.39 g, 1.11 mmol) in dioxane (15 cm$^3$) was added dropwise 1 M NaOH (7.5 cm$^3$, 7.50 mmol) and the mixture was stirred for 20 h at room temperature. The solution was acidified with 1 M HCl and evaporated in vacuo. The resulting aqueous layer was extracted with dichloromethane (2×30 cm$^3$), dried (MgSO$_4$), filtered and evaporated in vacuo to form a clear gum, which solidified on standing to acid 24 (0.35 g, 95%) as a colourless solid, which was used without further purification: $[\alpha]_D$ −9.9 (c 0.11 in MeOH); $\delta_H$ (300 MHz; CDCl$_3$) 0.83 (3H, t, J 7.4, CH$_3$), 1.93-2.22 (5H, m, CH$_2$CH$_3$, Proγ-H$_2$ and Pro-βH$_A$H$_B$), 2.35-2.40 (1H, m, Pro-βH$_A$H$_B$), 3.43-3.46 (1H, m, Proδ-H$_A$H$_B$), 3.57-3.62 (1H, m, Proδ-H$_A$H$_B$), 4.01 (2H, dd, J 4.3 and 17.3, Glyα-H$_2$), 5.11 (2H, s, OCH$_2$Ph), 5.82 (1H, br s, Gly-NH), 7.26-7.36 (5H, m, Ph) and 7.70 (1H, br s, CO$_2$H); $\delta_C$ (75 MHz; CDCl$_3$) 8.5 (CH$_3$, CH$_3$), 23.9 (CH$_2$, CH$_2$CH$_3$), 26.7 (CH$_2$, Proγ-C), 34.8 (CH$_2$, Proβ-C), 44.1 (CH$_2$, Glyα-C), 48.7 (CH$_2$, Proδ-C), 67.3 (CH$_2$, OCH$_2$Ph), 71.9 (quat., Proα-C), 127.3 (CH, Ph), 127.9 (CH, Ph), 128.3 (CH, Ph), 128.4 (CH, Ph), 128.9 (CH, Ph), 136.7 (quat., Ph), 156.7 (quat., NCO$_2$), 168.9 (quat., Gly-CON) and 175.8 (quat., CO$_2$H); m/z(EI$^+$) 334.1523 (M$^+$, C$_{17}$H$_{22}$N$_2$O$_5$ requires 334.1529).

1.1.17.
N-Benzyloxycarbonyl-glycyl-L-2-allylproline 25

To a solution of ester 20 (0.12 g, 0.34 mmol) in dioxane (7 cm$^3$) was added dropwise 1 M aqueous NaOH (2.06 cm$^3$, 2.06 mmol) and the mixture stirred for 20 h at room temperature. Dichloromethane (25 cm$^3$) was then added and the organic layer extracted with saturated aqueous sodium bicarbonate (3×25 cm$^3$). Careful acidification of the combined aqueous layers with dilute hydrochloric acid, extraction with dichloromethane (3×25 cm$^3$), drying of the combined organic layers (MgSO$_4$), filtration and concentration to dryness gave the acid 25 (0.11g, 92%) as a yellow oil: $[\alpha]_D$ −3.16 (c 0.95 in CH$_2$Cl$_2$); $v_{max}$ (film)/cm$^{-1}$ 3408, 2957, 2923, 2850, 2622, 1715, 1650, 1531, 1453, 1375, 1333, 1259, 1214, 1173, 1121, 1083, 1056, 1028, 1002, 916, 823, 737 and 698; $\delta_H$ (300 MHz; CDCl$_3$) 1.93-2.07 (3H, m, Proβ-H$_A$H$_B$ and Proγ-H$_2$), 2.22-2.26 (1H, m, Proβ-H$_A$H$_B$), 2.62-2.69 (1H, m, CH$_A$H$_B$CH=CH$_2$), 3.04-3.11 (1H, m, CH$_A$H$_B$CH=CH$_2$), 3.31-3.62 (2H, m, Proδ-H$_2$), 3.91-4.05 (2H, m, Glyα-H$_2$), 5.08-5.13 (3H, m, PhCH$_2$ and CH=CH$_A$H$_B$), 5.55-5.72 (1H, m, CH=CH$_A$H$_B$), 5.89 (1H, m, CH=CH$_2$), 7.29-7.45 (5H, m, PhH) and 8.12 (1H, br s, N—H); $\delta_C$ (75 MHz; CDCl$_3$) 23.5 (CH$_2$, Proγ-C), 34.6 (CH$_2$, Proβ-C), 37.5 (CH$_2$, CH$_2$CH=CH$_2$), 43.7 (CH$_2$, Glyα-C), 48.1 (CH$_2$, Proδ-C), 66.9 (CH$_2$, PhCH$_2$), 69.9 (quat., Proα-C), 119.8 (CH$_2$, CH=CH$_2$), 127.97 (CH, Ph), 128.04 (CH, Ph), 128.4 (CH, Ph), 132.3 (CH, CH=CH$_2$), 136.4 (quat., Ph), 156.4 (quat., NCO$_2$), 168.2 (quat., Gly-CON) and 176.1 (quat., CO$_2$H); m/z (EI+) 346.1526 (M$^+$.C$_{18}$H$_{22}$N$_2$O$_5$ requires 346.1529).

1.1.18.
N-tert-Butyloxycarbonyl-glycyl-L-2-allylproline 26

To a solution of ester 21 (0.039 g, 0.12 mmol) in dioxane (2.4 cm$^3$) was added dropwise 1 M aqueous NaOH (0.72 cm$^3$, 0.72 mmol) and the mixture was stirred for 16 h at room temperature. Dichloromethane (10 cm$^3$) was then added and the organic layer extracted with saturated aqueous sodium bicarbonate (3×10 cm$^3$). Careful acidification of the combined aqueous layers with dilute hydrochloric acid, extraction with dichloromethane (3×10 cm$^3$), drying of the combined organic layers (MgSO$_4$), filtration and concentration to dryness gave acid 26 (0.031 g, 83%) as a yellow oil: $[\alpha]_D$ −15.8 (c 0.89 in CH$_2$Cl$_2$); $v_{max}$ (film)/cm$^{-1}$ 3414, 3076, 2978, 2931, 2620, 1713, 1654, 1510, 1454, 1434, 1392, 1367, 1268, 1250, 1213, 1169, 1121, 1056, 1028, 920, 869, 779, 736 and 701; $\delta_H$ (300 MHz; CDCl$_3$) 1.43 [9H, s, C(CH$_3$)$_3$], 1.95-2.15 (3H, m, Proβ-H$_A$H$_B$ and Proγ-CH$_2$), 2.21-2.35 (1H, m, Proβ-H$_A$H$_B$), 2.63-2.70 (1H, m, CH$_A$H$_B$CH=CH$_2$), 3.04-3.11 (1H, m, CH$_A$H$_B$CH=CH$_2$), 3.35-3.47 (1H, m, Proδ-H$_A$H$_B$), 3.53-3.62 (1H, m, Proδ-H$_A$H$_B$), 3.92 (2H, m, Glyα-H$_2$), 5.08-5.13 (2H, m, CH=CH$_2$), 5.52 (1H, br s, Gly-NH), 5.56-5.71 (1H, m, CH=CH$_2$) and 8.31 (1 H, br s, OH); δ$_C$ (75 MHz; CDCl$_3$) 23.5 (CH$_2$, Proγ-C), 28.3 [CH$_3$, C(CH$_3$)$_3$], 34.6 (CH$_2$, Proβ-C), 37.5 (CH$_2$, CH$_2$CH=CH$_2$), 43.4 (CH$_2$, Glyα-C), 48.1 (CH$_2$, Proδ-C), 69.8 (quat., Proα-C), 79.8 [quat., C(CH$_3$)$_3$], 119.8 (CH$_2$, CH=CH$_2$), 132.3 (CH, CH=CH$_2$), 155.8 (quat., NCO$_2$), 168.5 (quat., Gly-CON) and 175.9 (quat., CO$_2$H); m/z (EI+) 312.1692 (M$^+$.C$_{15}$H$_{24}$N$_2$O$_5$ requires 312.1685).

1.1.19.
N-tert-Butyloxycarbonyl-glycyl-L-2-benzylproline
27

To a solution of ester 22 (0.098 g, 0.26 mmol) in dioxane (5.2 cm$^3$) was added dropwise 1 M aqueous NaOH (1.56 cm$^3$, 1.56 mmol) and the mixture was stirred for 15 h at room temperature. Dichloromethane (20 cm$^3$) was then added and the organic layer extracted with saturated aqueous sodium bicarbonate (3×20 cm$^3$). Careful acidification of the combined aqueous layers with dilute hydrochloric acid, extraction with dichloromethane (3×20 cm$^3$), drying of the combined organic layers (MgSO$_4$), filtration and concentration to dryness gave the acid 27 (0.09 g, 95%) as a colourless glass-like solid: mp 74-77° C.; [α]$_D$ +69.8 (c 0.99 in CH$_2$Cl$_2$); v$_{max}$ (CH$_2$Cl$_2$)/cm$^{-1}$ 3415, 3060, 3028, 2978, 2879, 2621, 1711, 1655, 1497, 1454, 1392, 1367, 1252, 1167, 1120, 1092, 1081, 1049, 1029, 988, 942, 915, 887, 872, 814, 764, 736, 705 and 653; δ$_H$ (400 MHz; CDCl$_3$) 1.14-1.21 (1H, m, Proγ-H$_A$H$_B$), 1.50 [9H, s, C(CH$_3$)$_3$], 1.72-1.78 (1H, m, Proγ-H$_A$H$_B$), 2.11-2.29 (2H, m, Proβ-H$_2$), 2.94-3.00 (1H, m, Proδ-H$_A$H$_B$), 3.13 (1H, d, J 13.9, PhCH$_A$H$_B$), 3.42-3.48 (1H, m, Proδ-H$_A$H$_B$), 3.83 (1H, d, J 13.9, PhCH$_A$H$_B$), 4.13 (2H, m, Glyα-H$_2$), 5.69 (1H, br s, Gly-NH), 7.10-7.33 (5H, m, PhH) and 8.37 (1H, br s, OH); δ$_C$ (100 MHz; CDCl$_3$) 23.3 (CH$_2$, Proγ-C), 28.3 [CH$_3$, C(CH$_3$)$_3$], 34.5 (CH$_2$, Proβ-C), 37.8 (CH$_2$, PhCH$_2$), 43.7 (CH$_2$, Glyα-C), 47.8 (CH$_2$, Proδ-C), 70.3 (quat., Proα-C), 79.8 [quat., C(CH$_3$)$_3$], 126.9 (CH, Ph), 128.4 (CH, Ph), 130.5 (CH, Ph), 136.3 (quat., Ph), 156.0 (quat., NCO$_2$), 168.6 (quat., Gly-CON) and 176.9 (quat., CO$_2$H); m/z (EI+) 362.1834 (M$^+$.C$_{19}$H$_{26}$N$_2$O$_5$ requires 362.1842).

1.1.20. Dibenzyl N-benzyloxycarbonyl-glycyl-L-2-methylprolyl-L-glutamate 30

Triethylamine (0.50 cm$^3$, 3.59 mmol) was added dropwise to a solution of dipeptide 23 (0.36 g, 1.12 mmol) and L-glutamic acid dibenzyl ester p-toluenesulphonate 28 (0.73 g, 1.46 mmol) in dichloromethane (60 cm$^3$) under nitrogen at room temperature, and the reaction mixture stirred for 10 min. Bis(2-oxo-3-oxazolidinyl)phosphinic chloride (0.37 g, 1.41 mmol) was added and the colourless solution stirred for 17 h. The dichloromethane solution was washed successively with 10% aqueous hydrochloric acid (50 cm$^3$) and saturated aqueous sodium hydrogen carbonate (50 cm$^3$), dried (MgSO$_4$), filtered, and evaporated to dryness in vacuo. Purification of the resultant residue by repeated flash column chromatography (30-70% ethyl acetate-hexane; gradient elution) yielded protected tripeptide 30 (0.63 g, 89%) as a colourless oil. Tripeptide 30 was shown to adopt exclusively the trans conformer by NMR: R$_f$ 0.55 (EtOAc); [α]$_D$ −41.9 (c 0.29 in CH$_2$Cl$_2$); v$_{max}$ (film)/cm$^{-1}$, 3583, 3353 br, 2950, 1734, 1660, 1521, 1499, 1454, 1429, 1257, 1214, 1188, 1166, 1051, 911, 737 and 697; δ$_H$ (400 MHz; CDCl$_3$; Me$_4$Si) 1.64 (3H, s, Proα-CH$_3$), 1.72 (1H, dt, J 12.8, 7.6 and 7.6, Proβ-H$_A$H$_B$), 1.92 (2H, 5 lines, J 6.7, Proγ-H$_2$), 2.04 (1H, 6 lines, J 7.3 Gluβ-H$_A$H$_B$), 2.17-2.27 (1H, m, Gluβ-H$_A$H$_B$), 2.35-2.51 (3H, m, Proβ-H$_A$H$_B$ and Gluγ-H$_2$), 3.37-3.57 (2H, m, Proδ-H$_2$), 3.90 (1H, dd, J 17.0 and 3.6, Glyα-H$_A$H$_B$), 4.00 (1H, dd, J 17.1 and 5.1, Glyα-H$_A$H$_B$), 4.56 (1H, td, J 7.7 and 4.9, Gluα-H), 5.05-5.20 (6H, m, 3×OCH$_2$Ph), 5.66-5.72 (1H, br m, Gly-NH), 7.26-7.37 (15H, m, 3×Ph) and 7.44 (1H, d, J 7.2, Glu-NH); δ$_C$ (100 MHz; CDCl$_3$) 21.9 (CH$_3$, Proα-CH$_3$), 23.4 (CH$_2$, Proγ-C), 26.6 (CH$_2$, Gluβ-C), 30.1 (CH$_2$, Gluγ-C), 38.3 (CH$_2$, Proβ-C), 43.9 (CH$_2$, Glyα-C), 47.6 (CH$_2$, Proδ-C), 52.2 (CH, Gluα-C), 66.4 (CH$_2$, OCH$_2$Ph), 66.8 (CH$_2$, OCH$_2$Ph), 67.1 (CH$_2$, OCH$_2$Ph), 68.2 (quat., Proα-C), 127.9 (CH, Ph), 128.0 (CH, Ph), 128.1, (CH, Ph), 128.2, (CH, Ph), 128.2, (CH, Ph), 128.3, (CH, Ph), 128.4, (CH, Ph), 128.5, (CH, Ph), 128.5, (CH, Ph), 135.2 (quat., Ph), 135.7 (quat., Ph), 136.4 (quat., Ph), 156.1 (quat., NCO$_2$), 167.3 (quat., Gly-CO), 171.4 (quat., CO), 172.9 (quat., CO) and 173.4 (quat., CO); m/z (FAB+) 630.2809 (MH$^+$.C$_{35}$R$_{40}$N$_3$O$_8$ requires 630.2815).

1.1.21. Dibenzyl N-benzyloxycarbonyl-glycyl-L-2-ethylprolyl-L-glutamate 31

Dry triethylamine (0.44 cm$^3$, 3.16 mmol) was added to a solution of acid 24 (0.30 g, 0.91 mmol) and L-glutamic acid dibenzyl ester p-toluene sulphonate 28 (0.57 g, 1.13 mmol) in dry dichloromethane (50 cm$^3$) under an atmosphere of nitrogen at 0° C., and the reaction mixture stirred for 10 min. Bis(2-oxo-3-oxazolidinyl)phosphinic chloride (0.29 g, 1.14 mmol) was added and the solution stirred for 2 h, warmed to room temperature and further stirred for 17.5 h. The solution was washed successively with 0.5 M aqueous hydrochloric acid (10 cm$^3$) and saturated aqueous sodium hydrogen carbonate (10 cm$^3$), dried (MgSO$_4$), filtered and evaporated in vacuo to form a light orange gum. Purification of the resultant residue by flash column chromatography (30% ethyl acetate/hexane) yielded protected tripeptide 31 (0.41 g, 70%) as a clear oil: [α]$_D$ −52.7 (c 0.16 in MeOH); δ$_H$ (300 MHz; CDCl$_3$) 0.78 (3 H, t, J 7.4, CH$_3$), 1.25-2.24 (7 H, m, CH$_2$CH$_3$, Gluβ-H$_2$, Proγ-H$_2$ and Proβ-H$_A$H$_B$), 2.34-2.40 (2H, m, Gluγ-H$_2$), 2.50-2.60 (1 H, m, Proβ-H$_A$H$_B$), 3.34 (1 H, q, J 9.4, Proδ-H$_A$H$_B$), 3.49-3.53 (1 H, m, Proδ-H$_A$H$_B$), 3.96 (2 H, ddd, J 4.9 and 17.3, Glyα-H$_2$), 4.51-4.54 (1 H, td, J 5.4 and 7.8, Gluα-H), 5.06-5.19 (6 H, m, 3×OCH$_2$Ph), 5.70 (1H, br s, Gly-NH), 7.26-7.36 (15H, 3×Ph) and 8.09 (1H, d, J 7.3, Glu-NH); cc (75 MHz; CDCl$_3$) 8.8 (CH$_3$, CH$_3$), 23.6 (CH$_2$, CH$_2$CH$_3$), 27.2 (CH$_2$, Proγ-C), 27.7 (CH$_2$, Gluβ-C), 30.6 (CH$_2$, Gluγ-C), 34.3 (CH$_2$, Proβ-C), 44.5 (CH$_2$, Glyα-C), 49.0 (CH$_2$, Proδ-C), 52.6 (CH, Gluα-C), 66.9 (CH$_2$, OCH$_2$Ph), 67.3 (CH$_2$, OCH$_2$Ph), 67.5 (CH$_2$, OCH$_2$Ph), 73.9 (quat., Proα-C), 128.4 (CH, Ph), 128.5 (CH, Ph), 128.6 (CH, Ph), 128.7 (CH, Ph), 128.8 (CH, Ph), 128.9 (CH, Ph), 135.7 (quat., Ph), 136.1 (quat., Ph), 136.8 (quat., Ph), 156.6 (quat., NCO$_2$), 168.7 (quat., Gly-CON), 171.8 (quat., Pro-CON), 172.9 (quat., Gluα-CO) and 173.6 (quat., Gluγ-CO); m/z (FAB+) 644.2981 (MH$^+$.C$_{36}$H$_{42}$N$_3$O$_8$ requires 644.2972).

1.1.22. Dibenzyl N-benzyloxycarbonyl-glycyl-L-2-allylprolyl-L-glutamate 32

Dry triethylamine (0.07 cm$^3$, 0.49 mmol) was added dropwise to a solution of acid 25 (0.05 g, 0.15 mmol) and L-glutamic acid dibenzyl ester p-toluenesulphonate 28 (0.10 g, 0.20 mmol) in dry dichloromethane (8.2 cm$^3$) under an atmosphere of nitrogen at room temperature, and the reaction mixture stirred for 10 min. Bis(2-oxo-3-oxazolidinyl)phosphinic chloride (0.05 g, 0.19 mmol) was added and the solution was stirred for 19.5 h. The solution was washed successively with 10% aqueous hydrochloric acid (7 cm$^3$) and saturated aqueous sodium hydrogen carbonate (7 cm$^3$), dried (MgSO$_4$), filtered and evaporated to dryness in vacuo. Purification of the resultant residue by flash column chromatography (δ0-80% ethyl acetate-hexane; gradient elution) yielded protected tripeptide 32 (0.08 g, 76%) as a colourless oil: $[\alpha]_D$ −27.8 (c 0.79 in CH$_2$Cl$_2$); $\nu_{max}$ (film)/cm$^{-1}$ 3943, 3583, 3413, 3055, 3032, 2982, 2956, 2880, 2685, 2411, 2305, 1955, 1732, 1668, 1586, 1499, 1454, 1423, 1388, 1329, 1265, 1214, 1169, 1170, 1081, 1058, 1028, 994, 924, 897, 824, 737 and 701; $\delta_H$ (400 MHz; CDCl$_3$) 1.85 (3H, m, Proβ-H$_A$H$_B$ and Proγ-H$_2$), 1.99-2.08 (1H, m, Gluβ-H$_A$H$_B$), 2.17-2.25 (1H, m, Gluβ-H$_A$H$_B$), 2.32-2.49 (3H, m, Proβ-H$_A$H$_B$ and Gluγ-H$_2$), 2.71-2.76 (1H, m, CH$_A$H$_B$CH=CH$_2$), 3.05-3.10 (1H, m, CH$_A$H$_B$CH=CH$_2$), 3.33 (1H, m, Proδ-H$_A$H$_B$), 3.51 (1H, m, Proδ-H$_A$H$_B$), 3.96 (2H, d, J 3.9, Glyα-H$_2$), 4.55 (1H, dd, J 7.6 and 5.1, Gluα-H), 5.07-5.19 (8H, m, 3×PhCH$_2$ and CH=CH$_2$), 5.53-5.63 (1H, m, CH=CH$_2$), 5.71 (1H, br s, Gly-NH), 7.32-7.36 (15H, m, 3×Ph) and 7.90 (1H, d, J 7.2, Glu-NH); $\delta_C$ (100 MHz; CDCl$_3$) 23.1 (CH$_2$, Proγ-C), 26.7 (CH$_2$, Gluβ-C), 30.2 (CH$_2$, Gluγ-C), 34.2 (CH$_2$, Proβ-C), 37.9 (CH$_2$, CH$_2$CH=CH$_2$), 44.1 (CH$_2$, Glyα-C), 48.5 (CH$_2$, Proδ-C), 52.2 (CH, Gluα-C), 66.4 (CH$_2$, PhCH$_2$), 66.9 (CH$_2$, PhCH$_2$), 67.2 (CH$_2$, PhCH$_2$), 71.9 (quat., Proα-C), 119.9 (CH$_2$, CH=CH$_2$), 127.9 (CH, Ph), 128.05 (CH, Ph), 128.1 (CH, Ph), 128.2 (CH, Ph), 128.3 (CH, Ph), 128.4 (CH, Ph), 128.45 (CH, Ph), 128.5 (CH, Ph), 132.1 (CH, CH=CH$_2$), 135.3 (quat., Ph), 135.7 (quat., Ph), 136.4 (quat., Ph), 156.2 (quat., NCO$_2$), 168.1 (quat., Gly-CO), 171.3 (quat., Gluα-CO), 172.7 (quat., Gluγ-CO) and 173.0 (quat., Pro-CON); m/z (FAB+) 656.2970 (MH$^+$.C$_{37}$H$_{42}$N$_3$O$_8$ requires 656.2992).

1.1.23. Di-tert-butyl N-tert-butyloxycarbonyl-glycyl-L-2-allylprolyl-L-glutamate 33

Dry triethylamine (0.044 cm$^3$, 0.32 mmol) was added dropwise to a solution of acid 26 (0.031 g, 0.10 mmol) and L-glutamic acid di-tert-butyl ester hydrochloride 29 (0.038 g, 0.129 mmol) in dry dichloromethane (5.30 cm$^3$) under an atmosphere of nitrogen at room temperature, and the reaction mixture stirred for 10 min. Bis(2-oxo-3-oxazolidinyl)phosphinic chloride (0.032 g, 0.13 mmol) was added and the solution stirred for 17.5h. The solution was washed successively with 10% aqueous hydrochloric acid (5 cm$^3$) and saturated aqueous sodium hydrogen carbonate (5 cm$^3$), dried (MgSO$_4$), filtered and evaporated to dryness in vacuo. Purification of the resultant residue by flash column chromatography (50% ethyl acetate-hexane) yielded protected tripeptide 33 (0.43 g, 77%) as a light yellow oil: $[\alpha]_D$ −29.9 (c 0.90 in CH$_2$Cl$_2$); $\nu_{max}$ (film)/cm$^{-1}$ 3583, 3417, 3076, 2978, 2931, 1728, 1664, 1522, 1453, 1426, 1392, 1367, 1329, 1251, 1158, 1056, 1028, 949, 919, 846 and 735; $\delta_H$ (300 MHz; CDCl$_3$) 1.26 [9H, s, C(CH$_3$)$_3$], 1.42 [9H, s, C(CH$_3$)$_3$], 1.43 [9H, s, C(CH$_3$)$_3$], 1.85-1.94 (4H, m, Proβ-H$_A$H$_B$, Gluβ-H$_A$H$_B$ and Proγ-H$_2$), 2.02-2.12 (1H, m, Gluβ-H$_A$H$_B$), 2.16-2.33 (2H, m, Gluγ-H$_2$), 2.48-2.53 (1H, m, Proβ-H$_A$H$_B$), 2.69-2.77 (1H, m, 0.5 CH$_A$H$_B$CH=CH$_2$), 3.08-3.15 (1H, m, CH$_A$H$_B$CH=CH$_2$), 3.29-3.38 (1H, m, Proδ-H$_A$H$_B$), 3.53-3.56 (1H, m, Proδ-H$_A$H$_B$), 3.91 (2H, d, J 4.0, Glyα-H$_2$), 4.33 (1H, dd, J 7.5 and 5.2, Gluα-H), 5.08-5.14 (2H, m, CH=CH$_2$), 5.47 (1H, br s, Gly-NH), 5.52-5.66 (1H, m, CH=CH$_2$) and 7.77 (1H, d, J 7.4, Glu-NH); $\delta_C$ (75 MHz; CDCl$_3$) 23.1 (CH$_2$, Proγ-C), 27.4 (CH$_2$, Gluβ-C), 27.9 [CH$_3$, C(CH$_3$)$_3$], 28.0 [CH$_3$, C(CH$_3$)$_3$], 28.3 [CH$_3$, C(CH$_3$)$_3$], 31.5 (CH$_2$, Gluγ-C), 34.2 (CH$_2$, Proβ-C), 38.0 (CH$_2$, CH$_2$CH=CH$_2$), 43.7 (CH$_2$, Glyα-C), 48.4 (CH$_2$, Proδ-C), 52.7 (CH, Gluα-C), 71.8 (quat., Proα-C), 79.5 [quat., C(CH$_3$)$_3$], 80.6 [quat., C(CH$_3$)$_3$], 81.9 [quat., C(CH$_3$)$_3$], 119.8 (CH$_2$, CH=CH$_2$), 132.3 (CH, CH=CH$_2$), 155.7 (quat., NCO$_2$), 168.4 (quat., Gly-CO), 170.8 (quat., Gluα-CO), 172.3 (quat., Gluγ-CO) and 172.8 (quat., Pro-CON); m/z (EI+) 553.3359 (M$^+$.C$_{28}$H$_{47}$N$_3$O$_8$ requires 553.3363).

1.1.24. Di-tert-butyl N-tert-butyloxycarbonyl-glycyl-L-2-benzylprolyl-L-glutamate 34

Dry triethylamine (0.11 cm$^3$, 0.77 mmol) was added dropwise to a solution of acid 27 (0.09 g, 0.24 mmol) L-glutamic acid di-tert-butyl ester hydrochloride 29 (0.09 g, 0.31 mmol) in dry dichloromethane (13 cm$^3$) under an atmosphere of nitrogen at room temperature, and the reaction mixture stirred for 10 min. Bis(2-oxo-3-oxazolidinyl)phosphinic chloride (0.08 g, 0.30 mmol) was added and the solution stirred for 17 h, then washed successively with 10% aqueous hydrochloric acid (12 cm$^3$) and saturated aqueous sodium hydrogen carbonate (12 cm$^3$), dried (MgSO$_4$), filtered and evaporated to dryness in vacuo. Purification of the resultant residue by flash column chromatography (40% ethyl acetate-hexane) yielded protected tripeptide 34 (0.10 g, 68%) as a colourless oil: $[\alpha]_D$ +15.7 (c 1.15 in CH$_2$Cl$_2$); $\nu_{max}$ (film)/cm$^-$ 3418, 3357, 3060, 3028, 2978, 2933, 2875, 1727, 1663, 1582, 1519, 1497, 1454, 1426, 1392, 1367, 1330, 1251, 1158, 1093, 1051, 1029, 949, 914, 846, 736, 705 and 651; $\delta_H$ (400 MHz; CDCl$_3$) 1.28-1.39 (1H, m, Proγ-H$_A$H$_B$), 1.43 [27H, s, C(CH$_3$)$_3$], 1.47 [27H, s, C(CH$_3$)$_3$], 1.48 [27H, s, C(CH$_3$)$_3$], 1.69-1.74 (1H, m, Proγ-H$_A$H$_B$), 1.89-1.99 (2H, m, Proβ-H$_2$), 2.08-2.17 (1H, m, Gluβ-H$_A$H$_B$), 2.23-2.41 (3H, m, Gluβ-H$_A$H$_B$ and Gluγ-H$_2$), 2.89-2.95 (1H, m, Proδ-H$_A$H$_B$), 3.13 (1H, d, J 13.4, PhCH$_A$H$_B$), 3.40-3.46 (1H, m, Proδ-H$_A$H$_B$), 3.85 (1H, d, J 13.4, PhCH$_A$H$_B$), 3.92 (2H, d, J 3.8, Glyα-H$_2$), 4.33 (1H, td, J 7.5 and 5.2, Gluα-H), 5.58 (1H, br s, Gly-NH), 7.07-7.28 (5H, m, PhH) and 7.71 (1H, d, J 7.2, Glu-NH); $\delta_H$ (100 MHz; CDCl$_3$) 23.0 (CH$_2$, Proγ-C), 27.4 (CH$_2$, Gluβ-C), 28.0 [CH$_3$, C(CH$_3$)$_3$], 28.1 [CH$_3$, C(CH$_3$)$_3$], 28.3 [CH$_3$, C(CH$_3$)$_3$], 31.5 (CH$_2$, Gluγ-C), 34.2 (CH$_2$, Proβ-C), 38.0 (CH$_2$, PhCH$_2$), 44.1 (CH$_2$, Glyα-C), 48.2 (CH$_2$, Proδ-C), 52.9 (CH, Gluα-C), 72.4 (quat., Proα-C), 79.6 [quat., C(CH$_3$)$_3$], 80.7 [quat., C(CH$_3$)$_3$], 82.1 [quat., C(CH$_3$)$_3$], 126.8 (CH, Ph), 128.3 (CH, Ph), 130.4 (CH, Ph), 136.3 (quat., Ph), 155.8 (quat., NCO$_2$), 168.6 (quat., Gly-CO), 171.0 (quat., Gluα-CO), 172.5 (quat., Gluγ-CO) and 173.1 (quat., Pro-CON); m/z (FAB+) 604.3592 (MH$^+$.C$_{32}$H$_{50}$N$_3$O$_8$ requires 604.3598).

1.1.25. Glycyl-L-2-methylprolyl-L-glutamic acid 1

A mixture of the protected tripeptide 30 (0.63 g, 1.00 mmol) and 10% palladium on activated carbon (0.32 g, 0.30 mmol) in 90:10 methanol-water (22 cm$^3$) was stirred under an atmosphere of hydrogen at room temperature, protected from light, for 23 h. The reaction mixture was filtered through a Celite™ pad and the pad washed with 75:25 methanol-water (200 cm$^3$). The filtrate was concentrated to dryness under reduced pressure and the residue triturated with anhydrous diethyl ether to afford tripeptide 1 (0.27 g, 86%) as an hygroscopic colourless solid. Tripeptide 1 was shown to adopt the trans conformation by NMR analysis: mp 144°; $[\alpha]_D$ −52.4 (c 0.19 in H$_2$O); H (400 MHz; D$_2$O) 1.62 (3H, s, Proα-CH$_3$), 1.97-2.25 (6H, m, Proβ-H$_2$, Proγ-H$_2$ and Gluβ-H$_2$), 2.45 (2H, t, J 7.3, Gluγ-H$_2$), 3.62-3.70 (2H, m, Proδ-H$_2$), 3.96 (1H, d, J 16.5, Glyα-H$_A$H$_B$), 4.02 (1H, d, J 16.4, Glyα-H$_A$H$_B$) and 4.28

(1H, dd, J 8.4 and 4.7, Gluα-H); δ$_C$ (100 MHz; D$_2$O) 19.9 (CH$_3$, Proα-CH$_3$), 23.0 (CH$_2$, Proγ-C), 26.9 (CH$_2$, Gluβ-C), 30.9 (CH$_2$, Gluγ-C), 38.8 (CH$_2$, Proβ-C), 40.7 (CH$_2$, Glyα-C), 47.5 (CH$_2$, Proδ-C), 54.4 (CH, Gluα-C), 67.8 (quat., Proα-C), 164.6 (quat., Gly-CO), 175.3 (quat., Pro-CON), 177.2 (quat., Gluα-CO), and 178.5 (quat., Gluγ-CO); m/z (FAB+) 316.1508 (MH$^+$.C$_{13}$H$_{22}$N$_3$O$_6$ requires 316.1509).

1.1.26. Glycyl-L-2-ethylprolyl-L-glutamic acid 2

A mixture of protected tripeptide 31 (0.51 g, 0.80 mmol) and 10% palladium on activated carbon (0.09 g, 0.08 mmol) in 90:10 methanol-water (50 cm$^3$) was stirred under an atmosphere of hydrogen at room temperature for 20 h. The solution was filtered through a Celite™ pad, the pad washed with methanol (2×30 cm$^3$) and the filtrate evaporated to dryness to give a clear gum. The gum was placed under vacuum for 30 min then triturated with anhydrous diethyl ether to tripeptide 2 (0.26 g, 99%) as an hygroscopic colourless solid. Tripeptide 2 was shown to be exclusively the trans conformer by $^1$H and $^{13}$C NMR analysis: mp 82-85° C.; [α]$_D$ −43.8 (c 0.1 in MeOH); δ$_H$ (400 MHz; D$_2$O) 0.86 (3 H, t, J 7.4, CH$_3$), 1.94-2.40 (8 H, m, CH$_2$CH$_3$, Gluβ-H$_2$, Proβ-H$_2$ and Pro-γH$_2$), 2.52-2.56 (2H, m, Gluγ-H$_2$), 3.55-3.61 (1 H, td, J 6.9 and 9.7, Proδ-H$_A$H$_B$), 3.75-3.80 (1 H, m, Proδ-H$_A$H$_B$), 4.08 (2H, q, J 16.6, Glyα-H$_2$) and 4.44 (1 H, q, J 4.9, Gluα-H); δ$_C$ (100 MHz; CDCl$_3$) 6.9 (CH$_3$, CH$_3$), 22.8 (CH$_2$, CH$_2$CH$_3$), 25.3 (CH$_2$, Proγ-C), 25.5 (CH$_2$, Gluβ-C), 30.11 (CH$_2$, Gluγ-C), 35.0 (CH$_2$, Proβ-C), 40.7 (CH$_2$, Glyα-C), 48.6 (CH$_2$, Proδ-C), 52.6 (CH, Gluα-C), 71.7 (quat., Proα-C), 164.9 (quat., Gly-CON), 175.2 (quat., Pro-CON) 176.0 (quat., Gluα-CO) and 177.3 (quat., Gluγ-CO); m/z (FAB+) 330.1667 (MH$^+$.C$_{14}$H$_{24}$N$_3$O$_6$ requires 330.1665).

1.1.27. Glycyl-L-2-propylprolyl-L-glutamic acid 3

A mixture of protected tripeptide 32 (64 mg, 0.097 mmol) and 10% palladium on activated carbon (20 mg, 0.19 mmol) in 90:10 methanol-water (9.8 cm$^3$) was stirred under an atmosphere of hydrogen at room temperature, protected from light, for 19 h. The reaction mixture was filtered through a Celite™ pad and the pad washed with 75:25 methanol-water (50 cm$^3$). The filtrate was concentrated to dryness under reduced pressure to afford tripeptide 3 (33 mg, 100%) as a colourless solid. Tripeptide 3 was shown to be exclusively the trans conformer by NMR analysis: mp 278-280° C. (dec.); [α]$_D$ −16.7 (c 0.18 in H$_2$O); i(300 MHz; D$_2$O) 0.98 (3H, t, CH$_2$CH$_3$), 1.09 (1H, m, CH$_A$H$_B$CH$_3$), 1.44 (1H, m, CH$_A$H$_B$CH$_3$), 1.82-2.31 (8H, m, Proβ-H$_2$, Proγ-H$_2$, Gluβ-H$_2$ and CH$_2$CH$_2$CH$_3$), 2.40 (1H, m, Gluγ-H$_2$), 3.55-3.63 (1H, m, Proδ-H$_A$H$_B$), 3.80 (1H, m, Proδ-H$_A$H$_B$), 4.03 (1H, d, J 16.6, Glyα-H$_A$H$_B$), 4.15 (1H, d, J 16.6, Glyα-H$_A$H$_B$) and 4.27 (1H, dd, J 8.2 and 4.8, Gluα-H); δ$_C$ (100 MHz; D$_2$O) 16.0 (CH$_3$, CH$_2$CH$_3$), 19.0 (CH$_2$, CH$_2$CH$_3$), 25.4 (CH$_2$, Proγ-C), 30.9 (CH$_2$, Gluβ-C), 36.3 (CH$_2$, Gluγ-C), 37.4 (CH$_2$, CH$_2$CH$_2$CH$_3$), 38.3 (CH$_2$, Proβ-C), 43.3 (CH$_2$, Glyα-C), 51.2 (CH$_2$, Proδ-C), 58.1 (CH, Gluα-C), 74.1 (quat., Proα-C), 167.7 (quat., NCO), 177.8 (quat., Pro-CON), 180.9 (quat., Gluα-CO) and 184.7 (quat., Gluγ-CO); m/z (FAB+) 344.1827 (MH$^+$.C$_{15}$H$_{26}$N$_3$O$_6$ requires 344.1822).

1.1.28. Glycyl-L-2-allylprolyl-L-glutamic acid trifluoroacetate 4

To a solution of the protected tripeptide 33 (41 mg, 0.073 mmol) in dichloromethane (4.5 cm$^3$) at room temperature was added trifluoroacetic acid (0.75 cm$^3$, 9.74 mmol) dropwise and the reaction mixture was stirred for 6.5 h. The solution was evaporated under reduced pressure to form tripeptide 4 (32 mg, 96%) as a pale yellow solid. Tripeptide 4 was shown to exist exclusively as the trans-conformer by NMR analysis: mp 105-108° C.; [α]$_D$ −7.64 (c 0.39 in H2O); δ$_H$ (400 MHz; D$_2$O) 1.90-2.02 (1H, m, Proγ-H$_A$H$_B$), 2.03-2.14 (2H, m, Proγ-H$_A$H$_B$ and Gluβ-H$_A$H$_B$), 2.19-2.32 (3H, m, Proβ-H$_2$ and Gluβ-H$_A$H$_B$), 2.54 (2H, ddd, J 8.1, 7.3, 2.0, Gluγ-H$_2$), 2.74 (1H, dd, J 13.7 and 7.3, CH$_A$H$_B$CH=CH$_2$), 3.12 (1H, dd, J 13.7 and 7.3, 0.5 CH$_A$H$_B$CH=CH$_2$), 3.48-3.55 (1H, m, Proδ-H$_A$H$_B$), 3.72-3.77 (1H, m, Proδ-H$_A$H$_B$), 3.98 (1H, d, J 16.7, Glyα-H$_A$H$_B$), 4.10 (1H, d, J 16.7, Glyα-H$_A$H$_B$), 4.46 (1H, dd, J 4.9 and 9.5, Gluα-H) 5.20-5.26 (2H, m, CH=CH$_2$) and 5.73-5.82 (1H, m, CH=CH$_2$); δ$_C$ (100 MHz; D$_2$O) 25.4 (CH$_2$, Proγ-C), 28.1 (CH$_2$, Gluβ-C), 32.7 (CH$_2$, Gluγ-C), 38.1 (CH$_2$, Proβ-C), 39.1 (CH$_2$, CH$_2$CH=CH$_2$), 43.3 (CH$_2$, Glyα-C), 51.0 (CH$_2$, Proδ-C), 55.1 (CH, Gluα-C), 73.2 (quat., Proα-C), 120.3 (quat., CF$_3$), 122.6 (CH$_2$, CH=CH$_2$), 134.4 (CH, CH=CH$_2$), 165.4 (quat., CF$_3$CO$_2$), 167.5 (quat., Gly-CO), 177.5 (quat., Pro-CON), 178.0 (quat., Glyα-CO) and 179.8 (quat., Gluγ-CO); m/z (EI+) 342.1653 (M$^+$-CF$_3$CO$_2$.C$_{15}$H$_{24}$N$_3$O$_6$ requires 342.1665).

1.1.29. Glycyl-L-2-benzylprolyl-L-glutamic acid trifluoroacetate 5

To a solution of the protected tripeptide 34 (98 mg, 0.16 mmol) in dichloromethane (4 cm$^3$) at room temperature was added trifluoroacetic acid (0.75 cm$^3$) dropwise and the reaction mixture was stirred for 3.5h. The solution was evaporated under reduced pressure to give tripeptide 5 (82 mg, 100%) as an hygroscopic colourless solid. Tripeptide 5 was shown to be a 90:10 trans:cis mixture of conformers by $^1$H NMR analysis (the ratio was estimated from the relative intensities of the double doublets and multiplet at δ 4.51 and 4.33, assigned to the Gluα-H protons of the major and minor conformers, respectively): mp 73-82° C.; [α]$_D$ +41.0 (c 1.61 in MeOH); 9H (300 MHz; D$_2$O) 1.27-1.39 (1H, m, Proγ-H$_A$H$_B$), 1.68-1.83 (1H, m, Proγ-H$_A$H$_B$), 2.07-2.42 (4H, m, Proβ-H$_2$ and Gluβ-H$_2$), 2.57 (2H, t, J 7.1, Gluγ-H$_2$), 2.82-2.92 (1H, m, Proδ-H$_A$H$_B$), 3.24 (1H, d, J 13.3, PhCH$_A$H$_B$), 3.50-3.59 (1H, m, Proδ-H$_A$H$_B$), 3.70 (1H, d, J 13.3, PhCH$_A$H$_B$), 3.91 (1H, d, J 16.7, Glyα-H$_A$H$_B$), 4.09 (1H, d, J 16.7, Glyα-H$_A$H$_B$), 4.33* (0.1H, m, Gluα-H), 4.51 (0.9H, dd, J 4.8 and 9.6, Gluα-H) and 7.21-7.44 (5H, m, PhH); δ$_C$ (100 MHz; D$_2$O) 25.0 (CH$_2$, Proγ-C), 27.9 (CH$_2$, Gluβ-C), 32.5 (CH$_2$, Gluγ-C), 37.7 (CH$_2$, Proβ-C), 39.2 (CH$_2$, PhCH$_2$), 43.5 (CH$_2$, Glyα-C), 50.6 (CH$_2$, Proδ-C), 54.9 (CH, Gluα-C), 56.0* (CH, Gluα-C), 73.8 (quat., Proα-C), 117.0 (quat., CF$_3$), 129.6 (CH, Ph), 131.1 (CH, Ph), 132.9 (CH, Ph), 138.3 (quat., Ph), 165.4 (quat., CF$_3$CO$_2$), 167.7 (quat., Gly-CO), 177.2 (quat., Pro-CON), 178.0 (quat., Gluα-CO) and 179.7 (quat., Gluγ-CO); m/z (FAB+) 392.1817 (M$^+$-CF$_3$CO.C$_{19}$H$_{26}$N$_3$O$_6$ requires 392.1822).

1.1.30. Dibenzyl (2S,5'R,8'R)- and (2S,5'R,8')-[1'-(2"-Benzyloxycarbonylamino-acetyl)-8'-hydroxy-6-oxo-1',7'-diazaspiro[4.4]non-7'-yl]-1,5-pentanedioate 38

Alkene 32 (96 mg, 0.15 mmol) was dissolved in dry dichloromethane-methanol (6 cm$^3$, 1:1) and the solution cooled to −78° C. A slow stream of ozone was bubbled through the solution for 15 min, followed by O$_2$ to remove excess ozone. Triphenylphosphine (57.5 mg, 0.22 mmol) was added and the resulting mixture vigorously stirred for 24 h, then a small amount of silica was added to the reaction mixture (containing aldehyde 37) and the solvent removed under reduced pressure. The resulting residue was purified by flash column chromatography (100% ethyl acetate) to afford hydroxyspirolactam 38 (61 mg, 63%) as a pale yellow oil. Hydroxyspirolactam 38 was shown to be a 7:3 mixture of diastereomers by $^1$H NMR analysis. The ratio was estimated from the relative intensities of the multiplet at δ 4.76-4.79 and the doublet of doublets at δ 5.00, assigned to the 2-H protons of the minor and major isomers, respectively) with the isomers being inseparable: $[α]_D$ −44.4 (c 0.90 in MeOH); $ν_{max}$ (film)/cm$^{-1}$ 3410, 3064, 3034, 2953, 2881, 2083, 1718, 1649, 1498, 1454, 1332, 1267, 1215, 1170, 1121, 1082, 1048, 1028, 1003, 984, 909, 776, 736 and 698; $δ_H$ (400 MHz; CDCl$_3$) 1.74-1.77* (0.3H, m, 9'-$H_AH_B$), 1.93-2.04 (1.3H, m, 9'-$H_AH_B$ and 3'-$H_A$*$H_B$), 2.11-2.39 [4.4H, m, 4'-$H_AH_B$, 3'-$H_AH_B$, 3-$H_AH_B$ and 3-$H_AH_B$ (major)], 2.42-2.66 (3.3H, m, 3-$H_AH_B$*, 4-$H_2$ and 4'-$H_AH_B$), 2.76 (0.7H, dd, J 12.9 and 6.1, 9'-$H_AH_B$), 3.46-3.58 (2H, m, 2'-$H_2$), 3.80-3.85* (0.3H, obsc., 2"-$H_AH_B$), 3.87 (0.7H, dd, J 17.5 and 3.3, 2"-$H_AH_B$), 4.02 (0.7H, dd, J 17.5 and 5.1, 2"-$H_AH_B$), 3.99-4.05* (0.3H, obsc., 2"-$H_AH_B$), 4.69 (1H, s, OH), 4.76-4.79* (0.3H, m, 2-H), 5.00 (0.7H, dd, J 10.8 and 4.8, 2-H), 5.09-5.21 (6H, m, 3×O$CH_2$Ph), 5.25* (0.3H, dd, J 12.3 and 7.1, 8'-H), 5.42 (0.7H, dd, J 6.0 and 2.4, 8'-H), 5.48* (0.3H, m, NH), 5.58-5.59 (0.7H, m, NH) and 7.27-7.39 (15H, m, 3×Ph); $δ_C$ (100 MHz; CDCl$_3$) 24.1* ($CH_2$, 3-C), 24.2 ($CH_2$, 3-C), 24.5 ($CH_2$, 3'-C), 25.3* ($CH_2$, 3'-C), 30.2 ($CH_2$, 4'-C), 30.7* ($CH_2$, 4'-C), 37.9 ($CH_2$, 4-C), 39.4 ($CH_2$, 9-C), 39.7* ($CH_2$, 9-C), 43.0* ($CH_2$, 2"-C), 43.7 ($CH_2$, 2"-C), 47.0 ($CH_2$, 2-C), 47.7* ($CH_2$, 2-C), 54.3 (CH, 2'-C), 54.7* (CH, 2'-C), 65.6* (quat., 5'-C), 66.2* ($CH_2$, O$CH_2$Ph), 66.4 ($CH_2$, O$CH_2$Ph), 66.8 ($CH_2$, O$CH_2$Ph), 67.0* ($CH_2$, O$CH_2$Ph), 67.2* ($CH_2$, O$CH_2$Ph), 67.3 ($CH_2$, O$CH_2$Ph), 68.1 (quat., 5'-C), 77.7 (CH, 8-C), 80.6* (CH, 8-C), 128.05 (CH, Ph), 128.09 (CH, Ph), 128.2 (CH, Ph), 128.4 (CH, Ph), 128.5 (CH, Ph), 128.6 (CH, Ph), 128.7 (CH, Ph), 134.5 (quat., Ph), 135.3* (quat., Ph), 135.8 (quat., Ph), 136.0* (quat., Ph), 136.4 (quat., Ph), 156.1 (quat., N$CO_2$), 166.0 (quat., 1"-C), 167.1* (quat., 1"-C), 170.1* (quat., 1'-C), 172.5 (quat., 1'-C), 172.7* (quat., 5'-C), 173.6 (quat., 5'-C), 173.8* (quat., 6-C) and 175.1 (quat., 6-C); m/z (FAB+) 658.2749 (MH$^+$.$C_{36}H_{40}N_3O_9$ requires 658.2765).

1.1.31. Dibenzyl (2S,5'R)-[1'-(2"-Benzyloxycarbonylamino-acetyl)-6'-oxo-1',7'-diazaspiro[4.4]non-7'-yl]-1,5-pentanedioate 39

A solution of hydroxyspirolactam 38 (33 mg, 0.05 mmol) in trifluoroacetic acid-triethylsilane-dichloromethane (1.0 cm$^3$, 1:1:1), at room temperature, was stirred for 45 min then concentrated in vacuo to give an opaque white oil which was purified by flash column chromatography (100% ethyl acetate) to afford spirolactam 39 (31 mg, 96%) as a colourless oil: $[α]_D$ −18.0 (c 0.67 in $CH_2Cl_2$); $ν_{max}$ (film)/cm$^{-1}$ 3583, 3412, 3032, 2952, 1734, 1654, 1497, 1454, 1432, 1289, 1259, 1215, 1171, 1048, 982, 738 and 698; O (300 MHz; CDCl$_3$) 1.76-2.19 (6H, m, 9'-$H_AH_B$, 4'-$H_2$, 3'-$H_AH_B$ and 3-$H_2$), 2.31-2.63 (4H, m, 9'-$H_AH_B$, 3'-$H_AH_B$ and 4-$H_2$), 3.31 (1H, dd, J 16.8 and 8.1, 8'-$H_AH_B$), 3.40-3.47 (1H, m, 8'-$H_AH_B$), 3.51-3.55 (2H, m, 2'-$H_2$), 3.86 (1H, dd, J 17.1 and 3.3, 2"-$H_AH_B$), 4.05 (1H, dd, J 17.1 and 5.4, 2"-$H_AH_B$), 4.90 (1H, dd, J 11.3 and 4.5, 2-H), 5.07-5.18 (6H, m, 3×O$CH_2$Ph), 5.63 (1H, br s, N—H) and 7.27-7.34 (15H, m, 3×Ph); $δ_C$ (75 MHz; CDCl$_3$) 23.4 ($CH_2$, 3'-C), 24.0 ($CH_2$, 3-C), 29.8 ($CH_2$, 9'-C), 30.4 ($CH_2$, 4-C), 36.2 ($CH_2$, 4'-C), 39.8 ($CH_2$, 8'-C), 43.7 ($CH_2$, 2"-C), 47.1 ($CH_2$, 2'-C), 53.8 (CH, 2-C), 66.3 ($CH_2$, O$CH_2$Ph), 66.9 ($CH_2$, O$CH_2$Ph), 67.2 ($CH_2$, O$CH_2$Ph), 68.2 (quat., 5-C), 128.0 (CH, Ph), 128.05 (CH, Ph), 128.1 (CH, Ph), 128.3 (CH, Ph), 128.49 (CH, Ph), 128.5 (CH, Ph), 128.7 (CH, Ph), 135.2 (quat., Ph), 136.0 (quat., Ph), 136.5 (quat., Ph), 156.2 (quat., N$CO_2$), 166.1 (quat., 1"-C), 170.1 (quat., 1-C), 172.7 (quat., 5-C) and 174.4 (quat., 6'-C); m/z (FAB+) 642.2802 (MH$^+$.$C_{36}H_{40}N_3O_8$ requires 642.2815).

1.1.31. (2S,5'R)-[1'-(2"-Amino-acetyl)-6'-oxo-1',7'-diazaspiro[4,4]non-7'-yl]-1,5-pentanedioic acid 35

A mixture of protected spirolactam 39 (30 mg, 0.047 mmol) and 10% palladium on activated carbon (9.6 mg, 0.09 mmol) in 88:12 methanol-water (6.6 cm$^3$) was stirred under an atmosphere of hydrogen at room temperature, protected from light, for 18 h. The reaction mixture was filtered through a Celite™ pad with 75:25 methanol-water (30 cm$^3$), and the filtrate concentrated to dryness under reduced pressure to give a yellow solid that was purified by reverse-phase C18 flash column chromatography (H$_2$O) to afford spirolactam 35 (12 mg, 78%) as a colourless solid: mp 238-239° C. (dec.); $[α]_D$ −23.5 [c 1.15 in MeOH—H$_2$O (1:1)]; $δ_H$ (400 MHz; D$_2$O) 1.97-2.61 (10H, m, 9'-$H_2$,4'-$H_2$,3'-$H_2$, 3-H2 and 4-$H_2$), 3.44-3.78 (4H, br m, 8'-$H_2$ and 2'-$H_2$) 3.81-4.12 (2H, br m, 2"-$H_2$) and 4.41 (1H, m, 2-H); $δ_C$ (1100 MHz; D$_2$O) 25.8 ($CH_2$, 3'-C), 27.8 ($CH_2$, 3-C), 31.4 ($CH_2$, 9'-C), 37.3 (2×$CH_2$, 4'-C and 4-C), 43.1 (2×$CH_2$, 8'-C and 2"-C), 50.1 ($CH_2$, 2'-C), 60.2 (CH, 2-C), 72.5 (quat., 5'-C), 173.6 (quat., 1"-C), 178.9 (quat., 6'-C) 179.1 (quat., 1-C) and 184.9 (quat., 5-C); m/z (FAB+) 328.1521 (MH$^+$. $C_{14}H_{21}N_3O_6$ requires 328.1509).

1.1.32. (2S,5'R,8'R)- and (2S,5'R,8'S)-[1'-(2"-Amino-acetyl)-8'-hydroxy-6'-oxo-1',7'-diazaspiro[4.4]non-7'-yl]-1,5-pentanedioic acid 36

A mixture of protected hydroxyspirolactam 38 (27 mg, 0.041 mmol) and 10% palladium on activated carbon (8.4 mg, 0.079 mmol) in 88:12 methanol-water (5.8 cm$^3$) was stirred under an atmosphere of hydrogen at room temperature, protected from light, for 18 h. The reaction mixture was filtered through a Celite™ pad with 75:25 methanol-water (30 cm$^3$) and the filtrate concentrated to dryness under reduced pressure to afford spirolactam 36 (14 mg, 99%) as a colourless solid. Spirolactam 36 was shown to be a 7:3 mixture of two diastereomers by $^1$H NMR analysis (the ratio was estimated from the relative intensities of the doublet of doublets at δ 4.47 and 4.53, assigned to 2-H of the minor and major isomers, respectively): mp 216-218° C. (dec.); $[α]_D$ +0.86 [c 0.35 in MeOH—H$_2$O (1:1)]; $δ_H$ (400 MHz; D$_2$O) 2.10-2.46 (9H, m, 9'-$H_AH_B$, 4'-$H_2$, 3'-$H_2$, 3-$H_2$ and 4-$H_2$), 2.65* (0.3H, dd, J 13.8 and 7.0, 9'-$H_AH_B$), 2.75 (0.7H, dd, J 13.6 and 6.2, 9'-$H_AH_B$), 3.55-3.61 (1H, m, 2'-$H_AH_B$), 3.69-3.73 (1H, m, 2'-$H_AH_B$), 3.94-4.09 (2H, d, J 16.5, 2"-$H_2$), 4.47* (0.3H, dd, J 9.9 and 5.8, 2-H), 4.53 (0.7H, dd, J 10.4 and 5.0, 2-H), 5.49* (0.3H, dd, J 6.8 and 5.1, 8'-H) and 5.59 (0.7H, d, J 6.1, 8'-H); $δ_C$ (100 MHz; D$_2$O) 26.0* ($CH_2$, 3'-C), 26.1 ($CH_2$, 3'-C), 27.4 ($CH_2$, 3-C), 29.6* ($CH_2$, 3-C), 39.3* ($CH_2$, 4-C), 40.1 ($CH_2$, 4-C), 40.7 (2×$CH_2$, 4'-C and 9'-C), 42.2* ($CH_2$, 9'-C), 43.1 ($CH_2$, 2"-C), 49.8 ($CH_2$, 2'-C), 49.9* ($CH_2$, 2'-C), 60.2* (CH, 2-C), 60.7 (CH, 2-C), 70.1* (quat., 5'-C), 70.9 (quat., 5'-C), 80.6 (CH, 8'-C), 83.2* (CH, 8'-C), 166.9 (quat., 1"-C), 167.1* (quat., 1"-C), 178.2* (quat., 6'-C), 179.7 (2×quat., 1-C and 6'-C), 180.4 (quat., 1-C), 182.5 (quat., 5-C) and 182.8* (quat., 5-C); m/z (FAB+) 344.1467 (MH$^+$.$C_{14}H_{22}N_3O_7$ requires 344.1458).

1.1.33. Methyl N-tert-Butyloxycarbonyl-(D,L)-5,5-dimethylprolinate 43

(Magaard et al. *Tetrahedron Lett* 1993, 34, 381) Nitrile 44 (Magaard et al. *Tetrahedron Lett* 1993, 34, 381; Bonnet et al. *J. Chem. Soc.* 1959, 34, 381) (2 g, 14.3 mmol) was dissolved in 32% hydrochloric acid (6 cm$^3$) and heated to 50° C. for 5 h. Evaporation of the solvent afforded a residue that was dissolved in methanol:water (1:1, 30 cm$^3$) and hydrogenated over 10% palladium on activated carbon (0.3 g) under 44 p.s.i of hydrogen for 20 h. The catalyst was removed by filtration through Celite™ and the solvent removed in vacuo to yield a 6:4 mixture of N-methyl-5-methylproline* 45, and the desired 5,5-dimethylproline 46: $\delta_H$ (300 MHz; D$_2$O) 1.34-1.40 (8.6H, m, 4×CH$_3$), 1.67-1.74 (1.3H, m) 1.91 (1.6H, t, J 12.2), 2.07-2.32 (3.5H, m), 2.40-2.54 (2H, m), 2.90* (3.6H, s, N—CH$_3$), 3.45-3.53 (1.3H, m), 4.23* (1.3H, dd, J 9.7 and 7.5, Proα-H) and 4.47 (1H, d, J 8.4, Proα-H); $\delta_C$ (75 MHz; D$_2$O) 14.6* (CH$_3$), 24.5 (CH$_3$), 24.7 (CH$_3$), 25.9* (CH$_2$), 27.2 (CH$_2$), 29.9* (CH$_2$), 37.0 (CH$_2$), 39.1* (CH$_3$, N—CH$_3$), 58.9* (CH, Proδ-C), 67.1 (quat., Proδ-C), 67.6* (CH, Proα-C), 69.2 (CH, Proα-C), 171.5* (quat., Proα-CO) and 172.4 (quat., Proα-CO). The mixture was subsequently dissolved in dry methanol (60 cm$^3$), cooled to 0° C. and thionyl chloride (4.2 cm$^3$, 57.2 mmol) was added dropwise over 5 min. The reaction was allowed to warm to room temperature and stirred overnight. The solvent was removed, the residue was dissolved in saturated sodium hydrogen carbonate solution and the products extracted with chloroform to yield a mixture of inseparable methyl esters (1.53 g) which were dissolved in dry dichloromethane (20 cm$^3$). N-Methylmorpholine (1.56 cm$^3$, 14.2 mmol) and di-tert-butyldicarbonate (3.1 g, 14.2 mmol) were added and the reaction was heated at reflux under nitrogen for 48 h. After cooling to room temperature the reaction mixture was washed with water, 1 M aqueous hydrochloric acid (2×30 cm$^3$), brine and dried (MgSO$_4$). The aqueous layer was concentrated in vacuo to give methyl N-methyl-5-methylprolinate 47 (1.093 g, 42%, 4 steps) as its hydrochloride salt. This was neutralized with saturated sodium hydrogen carbonate and purified by chromatography (silica gel, 4:1, dichloromethane:ethyl acetate): 94 (200 MHz; CDCl$_3$; Me$_4$Si) 1.06 (3H, d, J 6.0, Proδ-CH$_3$), 1.35-1.55 (1H, m), 1.70-2.01 (3H, m), 2.17-2.27 (1H, m), 2.24 (3H, s, N—CH$_3$), 2.90 (1H, t, J 7.8, Proα-H) and 3.65 (3H, s, 2-CO$_2$CH$_3$); $\delta_C$ (75 MHz; CDCl$_3$) 18.2 (CH$_3$, Proδ-CH$_3$), 26.4 (CH$_2$), 31.3 (CH$_2$), 38.9 (CH$_3$, N—CH$_3$), 51.3 (CH$_3$, Proα-CO$_2$CH$_3$) 61.8 (CH, Proδ-C), 68.4 (CH, Proα-C) and 173.6 (quat., Proα-CO); m/z (CI+) 158.1176 (MH$^+$·C$_8$H$_{16}$NO$_2$ requires 158.1181); The organic layer was concentrated in vacuo and purified by chromatography (silica gel, dichloromethane then chloroform) to give methyl N-tert-butyloxycarbonyl-(D,L)-5,5-dimethylprolinate 43 (0.795 g, 22%, 4 steps) as a yellow oil. This compound existed as a mixture of epimers (55:45) almost exclusively as the cis conformer: $\delta_H$ (300 MHz; CDCl$_3$) 1.26-1.53 [15H, m, C(CH$_3$)$_2$, C(CH$_3$)$_3$], 1.60-1.90 (4H, m, Proβ-H$_2$ and Proγ-H$_2$), 3.66 (3H, CO$_2$CH$_3$), 4.24 (0.55H, dd J 8.9 and 3.5, Proα-H) and 4.35 (0.45H, dd J 8.5 and 2.6, Proα-H); $\delta_C$(75 MHz; CDCl$_3$) 25.7 (CH$_3$, Proδ-CH$_3$), 25.9 (CH$_2$, Proγ-C), 26.0 (CH$_3$, Proδ-CH$_3$), 26.5 (CH$_2$, Proγ-C), 26.6 (CH$_3$, Proδ-CH$_3$), 27.2 (CH$_3$, Proδ-CH$_3$), 28.2 [CH$_3$, C(CH$_3$)$_3$], 28.3 [CH$_3$, C(CH$_3$)$_3$], 39.8 (CH$_2$, Proβ-C), 40.7 (CH$_2$, Proβ-C), 51.6 (CH$_3$, Proδ-CO$_2$CH$_3$), 51.7 (CH$_3$, Proα-CO$_2$CH$_3$), 60.5 (quat., Proδ-C), 61.16 (CH, Proα-C), 61.2 (CH, Proα-C), 61.3 (quat., Proδ-C), 79.1 [quat., C(CH$_3$)$_3$], 79.6 [quat., C(CH$_3$)$_3$], 152.4 (quat., NCO$_2$), 154.0 (quat., NCO$_2$), 173.4 (quat., Proδ-CO) and 173.8 (quat., Proα-CO); m/z (EI+) 257.1624 (M$^+$.C$_{13}$H$_{23}$NO$_4$ requires 257.1627).

1.1.34. N-tert-Butyloxyglycyl-L-4-thiaproline 52 iso-Butyl chloroformate (0.154 g, 1.12 mmol) was added to a stirred solution of N-tert-butyloxycarbonylglycine 17 and triethylamine (0.215 g, 1.15 mmol) in tetrahydrofuran (6 cm$^3$) at 0° C. A white precipitate was observed, the cooling bath was removed and the mixture stirred at room temperature for 10 mins. A solution of 4-thiaproline hydrochloride 40 (Pellegrini, above) (0.150 g, 1.12 mmol) and triethylamine (0.215 g, 1.15 mmol) in water (2 cm$^3$) was added and the resultant solution was stirred for 1 h. The mixture was acidified with 2 M HCl and extracted with ethyl acetate. The combined organic extracts were dried (Na$_2$SO$_4$), filtered and concentrated in vacuo to yield an oil (0.39 g) that was purified by flash chromatography (hexane:ethyl acetate:acetic acid 2:1:0.3 then 1:1:0.2) gave dipeptide 52 (0.264g, 81%) as a hygroscopic white foam. 52 was shown to be a 62:38 trans:cis mixture of conformers by $^1$H NMR analysis (the ratio was estimated from the integration of the GlyN-H protons at δ 5.65 and 5.75 assigned to major and minor conformers respectively): [α]$_D$ −93.5 (c 0.25 in CH$_2$Cl$_2$); $\delta_H$ (400 MHz; CDCl$_3$) 1.43* [3.4H, s, C(CH$_3$)$_3$], 1.44 [5.6H, s, C(CH$_3$)$_3$], 3.31 (1.24H, d, J 5.1, 3-H$_A$H$_B$), 3.37* (0.38H, dd, J 11.8 and 5.2, 3-H$_A$H$_B$), 3.49* (0.38H, dd, J 11.7 and 1.4, 3-H$_A$H$_B$), 3.90-4.20 (2H, m, Glyα-H$_2$), 4.55-4.62 (1.62H, m 5-H$_2$, *5-H$_A$H$_B$), 4.79* (0.38H, d, J 9.7, 5-H$_A$H$_B$), 4.86* (0.388H, d, J 5.7, 2-H), 5.11 (0.62H, t, J 4.9, 2-H), 5.65 (0.62H, br s, GlyN-H) and 5.75* (0.38H, br s, GlyN-H); c (100 MHz; CDCl$_3$) 28.2 [CH$_3$, C(CH$_3$)$_3$], 32.3 (CH$_2$, 3-C), 34.4 (CH$_2$, 3-C), 43.1 (CH$_2$, Glyα-C), 43.4* (CH$_2$, Glyα-C), 47.6 (CH$_2$, 5-C), 48.9* (CH$_2$, 5-C), 60.7* (CH, 2-C), 61.6 (CH, 2-C), 80.3* [quat., C(CH$_3$)$_3$], 80.7 [quat., C(CH$_3$)$_3$], 156.1 (quat., NCO$_2$), 156.4* (quat., NCO$_2$), 167.8 (quat., Gly-CO), 168.0* (quat., Gly-CO), 171.6 (quat., 2-CO) and 172.0* (quat., 2-CO); m/z (EI+) 290.0938 (M$^+$.C$_{11}$H$_{18}$N$_2$O$_5$S requires 290.0936).

1.1.35. Di-tert-butyl N-tert-butyloxycarbonylglycyl-L-4-thiaprolyl-L-glutamate 56

Ethyl chloroformate (0.048 g, 0.445 mmol) was added dropwise to a solution of acid 52 (0.129 g, 0.445 mmol) and triethylamine (0.050 g, 0.49 mmol) in dichloromethane (3 cm$^3$) at 0° C. The solution was stirred for 35 mins at 0° C. then a solution of glutamic acid di-tert-butyl ester hydrochloride 29 (0.132 g, 0.445 mmol) and triethylamine (0.050 g, 0.49 mmol) in dichloromethane (3 cm$^3$) was added. The mixture was stirred overnight, washed successively with 2 M aqueous hydrochloric acid, saturated sodium hydrogen carbonate solution, dried (Na$_2$SO$_4$), filtered and the solvent removed. Purification by flash chromatography (dichloromethane: ethyl acetate, 3:1) afforded protected tripeptide 56 (0.128 g, 54%) as a colourless solid. 56 was shown to be a 66:34 trans:cis mixture of conformers by $^1$H NMR analysis (the ratio was estimated from the integration of the thiaProN-H protons at δ 7.20 and 7.43 assigned to major and minor conformers respectively): mp 99-100° C.; [α]$_D$ −70 (c 0.6 in CH$_2$Cl$_2$); $\delta_H$ (400 MHz; CDCl$_3$) 1.25-1.45 [27H, m, C(CH$_3$)$_3$], 1.80-1.95 (1H, m, Gluβ-H$_A$H$_B$), 1.97-2.14 (11H, m, Gluβ-H$_A$H$_B$), 2.18-2.35 (2H, m, Gluγ-H$_2$), 3.14 (0.66H, dd, J 11.2 and 7.0, 3-H$_A$H$_B$), 3.22-3.35* (0.34H, br m, 3-H$_A$H$_B$), 3.38 (1H, dd, J 12.3 and 3.6, 3-H$_A$H$_B$), 3.85-4.05 (2H, m, Glyα-H$_2$), 4.38 (1H, br t, J 4.8, Gluα-H), 4.49-4.57 (1.66H, 5-H$_A$H$_B$ and *5-H$_A$H$_B$), 4.69-4.77* (0.72H, *5-H$_A$H$_B$ and *2-H), 4.98

(0.66H, br s, 2-H), 5.51 (1H, br s, GlyN-H), 7.20 (0.66H, d, J 7.2, thiaProN-H), 7.20* (0.34H, br s, thiaProN-H); $\delta_C$ (100 MHz; CDCl$_3$) 26.4* (CH$_2$, Gluβ-C), 27.1 (CH$_2$, Gluβ-C), 27.8 [CH$_3$, C(CH$_3$)$_3$], 27.9 [CH$_3$, C(CH$_3$)$_3$], 28.2 [CH$_3$, C(CH$_3$)$_3$], 31.3 (CH$_2$, Gluγ-C), 32.2 (CH$_2$, 3-C), 35.4* (CH$_2$, 3-C), 43.2 (CH$_2$, Glyα-C), 43.5* (CH$_2$, Gluγ-C), 48.2 (CH$_2$, 5-C), 49.7* (CH$_2$, 5-C), 52.5 (CH, Gluα-C), 62.3* (CH, 2-C), 62.5 (CH, 2-C), 79.7 [quat., C(CH$_3$)$_3$], 80.6 [quat., C(CH$_3$)$_3$], 80.9* [quat., C(CH$_3$)$_3$], 82.1 [quat., C(CH$_3$)$_3$], 82.2* [quat., C(CH$_3$)$_3$], 155.7 (quat., NCO$_2$), 167.9 (quat., Gly-CO), 168.6* (quat., 2-CO), 168.9 (quat., 2-CO), 170.4 (quat., Gluα-CO) and 172.4 (quat., Gluγ-CO); m/z (FAB+) 532.2628 (MH$^+$.C$_{24}$H$_{42}$N$_3$O$_8$S requires 532.2693).

1.1.36. Glycyl-L-4-thiaprolyl-L-glutamic acid trifluoroacetate 48

Trifluoroacetic acid (1 cm$^3$) was added to a stirred solution of protected tripeptide 56 (0.128 g, 0.241) and triethylsilane (0.084 g, 0.723 mmol) in dichloromethane (3 cm$^3$). The resultant solution was stirred for 4 h at room temperature and the volatiles removed in vacuo. Purification of the residue by chromatography (reverse phase C$_{18}$, water, 10-20% acetonitrile:water) and lyophilisation gave 48 (0.066 g, 61%) as a hygroscopic off white solid. 48 was shown to be a 80:20 trans:cis mixture of conformers by $^1$H NMR analysis (the ratio was estimated from the integration of the Glyα protons at δ 3.80-3.92 and 3.58 assigned to major and minor conformers respectively): no mp due to hygroscopic sample; [α]$_D$ –88.6 (c 0.203 in H$_2$O); $\delta_H$ (400 MHz; D$_2$O) 1.73-1.82 (1H, m, Gluβ-H$_A$H$_B$), 1.96-2.06 (1H, m, Gluβ-H$_A$H$_B$), 2.28 (2H, t, J 6.9, Gluγ-H$_2$), 2.96 (0.8H, dd, J 12.4 and 3.7, 3-H$_A$H$_B$), 3.13* (0.2H, d, 12.2, 3-H$_A$H$_B$), 3.20 (0.8H, dd, J 12.4 and 7.3, 3-H$_A$H$_B$), 3.27* (0.2H, dd, J 12.4 and 6.9, 3-H$_A$H$_B$), 3.58 (0.2H, d, J 16.4, Glyα-H$_A$H$_B$), 3.80-3.92 (1.8H, m, Glyα-H$_2$ and *Glyα-H$_A$H$_B$), 4.25 (0.8H, dd, 9.4 and 4.8, Gluα-H), 4.30* (0.2H, dd, 10.0 and 4.8, Gluα-H), 4.35-4.49 (2H, m, 5-H$_2$) and 4.67 (1H, dd, J 6.9 and 3.8, 2-H); $\delta_C$ (100 MHz; CDCl$_3$) 24.8* (CH$_2$, Gluβ-C), 25.3 (CH$_2$, Gluβ-C), 29.5 (CH$_2$, Gluγ-C), 29.8* (CH$_2$, Gluγ-C), 32.8 (CH$_2$, 3-C), 34.9* (CH$_2$, 3-C), 40.3 (CH$_2$, Glyα-C), 40.5* (CH$_2$, Glyα-C), 48.4 (CH$_2$, 5-C), 49.6* (CH$_2$, 5-C), 51.7 (CH, Gluα-C), 51.9* (CH, Gluα-C), 61.6* (CH, 2-C), 62.6 (CH, 2-C), 115.7 (quat., q, J 290.7, CF$_3$CO$_2$H), 161.9 (quat., q, J 36.2, CF$_3$CO$_2$H), 165.0 (quat., Gly-CO), 165.6* (quat., Gly-CO), 171.0* (quat., 2-CO), 171.5 (quat., 2-CO), 174.0* (quat., Gluα-CO), 174.1* (quat., Gluα-CO) and 176.7 (quat., Gluγ-CO); m/z (FAB+) 320.0921 [M (free base) H$^+$. C$_{11}$R$_{18}$N$_3$O$_6$S requires 320.0916].

1.1.37. N-Benzyloxycarbonylglycyl-L-thia-5,5-dimethylproline 53

To a stirred solution of 5,5,-dimethyl-4-thiaproline hydrochloride 41 (Lewis et al. *J. Med. Chem.* 1978, 21, 1071; Kemp et al. *J. Org. Chem.* 1989, 54, 3640) (0.354 g, 1.79 mmol) under nitrogen in dry dimethylformamide (35 cm$^3$) was added diisopropylethylamine (0.594 cm$^3$, 1.9 mmol) and acid fluoride 51 (Bertho et al. *Tetrahedron Lett.* 1991, 32, 1303; Carpino et al. *J. Org. Chem.* 1991, 56, 2611) (0.341 g, 1.61 mmol). The solution was stirred for 18 h, the solvent was removed in vacuo and the residue was redissolved in ethyl acetate, washed with 10% citric acid solution, brine and dried (MgSO$_4$). The solvent was removed and the residue purified by flash chromatography (4:1:0.5, ethyl acetate:hexane:acetic acid, then 3:1.0.4) to give the desired compound contaminated with N-benzyloxycarbonylglycine 16 (14%, $^1$H NMR).

This mixture was dissolved in methanol, trimethylsilyl chloride (0.07 cm$^3$) added and the solution stirred overnight. Removal of the solvent in vacuo and subsequent flash chromatography (3:1, ethyl acetate:hexane [to remove N-benzyloxycarbonylglycine methyl ester] then 3:1.0.4 ethyl acetate: hexane:acetic acid) gave dipeptide 53 (0.320 g, 65%, based on amount of acid fluoride reacted) as a white solid. This compound existed purely as the cis conformer: mp 130-132° C.; [α]$_D$ –51.7 (c 0.116 in dichloromethane); $\delta_H$ (300 MHz; CDCl$_3$) 1.85 (3H, s, $^\Psi$Pδ-CH$_3$) 1.91 (3H, s, Pδ-CH$_3$), 3.30 (1H, dd, J 12.1 and 5.6, Pβ-H$_A$H$_B$), 3.40 (1H, d, J 12.1, Pβ-H$_A$H$_B$), 3.87 (1H, dd, J 16.6 and 3.7, Glyα-H$_A$H$_B$), 4.09 (1H, dd, J 16.6 and 3.7, Glyα-H$_A$H$_B$), 4.82 (1H, d, J 5.2, Pα-H), 5.13 (2H, s, OCH$_2$Ph), 6.10 (1H, br t, J 3.8, GlyN-H) and 7.29-7.39 (5H, m, Ph); $\delta_H$ (75 MHz; CDCl$_3$) 27.0 (CH$_3$, Pδ-CH$_3$) 29.4 (CH$_3$, Pδ-CH$_3$), 31.6 (CH$_2$, Pβ-C), 44.8 (CH$_2$, Glyα-C), 64.3 (CH, Pα-C), 67.3 (CH$_2$, OCH$_2$Ph), 74.2 (quat., Pδ-C), 127.9 (CH, Ph), 128.1 (CH, Ph), 128.4 (CH, Ph), 135.8 (quat., Ph), 156.8 (quat., NCO$_2$), 166.6 (quat., Gly-CO) and 172.0 (quat., Pα-CO); m/z (EI+) 352.1088 (M$^+$.C$_{16}$H$_{20}$N$_2$O$_5$S requires 352.1093).

$^\Psi$P refers to the proline analog portion in question.

1.1.38. Dibenzyl N-benzyloxycarbonyl-glycyl-L-thia-5,5-dimethylprolyl-L-glutamate 57

To a stirred solution of dipeptide 53 (0.398 g, 1.11 mol), L-glutamic acid dibenzyl ester p-toluenesulfonate 28 (0.670 g, 1.34 mol) and diisopropylethylamine (0.51 cm$^3$, 2.90 mmol) in dry dichloromethane (40 cm$^3$) was added bis(2-oxo-3-oxazolidinyl)phosphinic chloride (0.370 g, 1.45 mmol) in one portion. The solution was stirred for 7 h under nitrogen and the solvent removed. The residue was suspended in ethyl acetate, washed with 10% citric acid solution, saturated sodium hydrogen carbonate, brine and dried (MgSO$_4$). Removal of the solvent and subsequent chromatography (2:1, hexane:ethyl acetate, then 1:1) gave protected tripeptide 57 (0.5 g, 68%) as a colourless oil. Protected tripeptide 57 was shown to be a 90:10 cis:trans mixture of conformers by $^1$H NMR analysis (the ratio was estimated from the integration of the broad singlets at δ 5.69 and 5.80 and assigned to the GlyN-H protons of the major and minor conformers respectively): [α]$_D$ –35.6 (c 0.399 in dichloromethane); $\delta_H$ (300 MHz; CDCl$_3$) 1.85 (3H, Pδ-CH$_3$) 1.97 (3H, Pδ-CH$_3$), 2.08-2.15 (1H, m, Gluβ-H$_A$H$_B$), 2.29-2.38 (1H, m, Gluβ-H$_A$H$_B$), 2.47 (2H, t, J 5.4, Gluγ-H$_2$), 3.32 (2H, m, Pβ-H$_2$), 3.85 (1H, d, J 16.6, Glyα-H$_A$H$_B$), 3.91 (1H, dd, J 17.0 and 8.0, Glyα-H$_A$H$_B$), 4.72 (2H, br s, Pα-H, Gluα-H), 5.20-5.08 (6H, m, 3×OCH$_2$Ph), 5.69 (0.9H, br s, Gly-NH), 5.80* (0.1H, br s, Gly-NH) and 7.33-7.39 (15H, m, Ph); $\delta_H$ (75 MHz; CDCl$_3$) 26.3 (CH$_2$, Gluβ-C), 26.45* (CH$_2$, Gluβ-C), 27.21* (CH$_3$, Pδ-CH$_3$), 27.43 (CH$_3$, Pδ-CH$_3$), 28.4 (CH$_3$, Pδ-CH$_3$), 29.91 (CH$_2$, Gluγ-C), 30.09* (CH$_2$, Gluγ-C), 32.3 (CH$_2$, Pβ-C), 44.7 (CH$_2$, Glyα-C), 45.1* (CH$_2$, Glyα-C), 52.1 (CH, Gluα-C), 52.3* (CH, Gluα-C), 65.8 (CH, Pα-H), 66.4 (CH$_2$, OCH$_2$Ph), 66.8 (CH$_2$, OCH$_2$Ph), 67.4 (CH$_2$, OCH$_2$Ph), 74.5 (quat., Pδ-C), 127.8 (CH, Ph), 127.9 (CH, Ph), 128.1 (CH, Ph), 128.14 (CH, Ph), 128.2 (CH, Ph), 128.3 (CH, Ph), 128.5 (CH, Ph), 134.8 (quat., Ph), 135.5 (quat., Ph), 136.2 (quat., Ph), 156.4 (quat., NCO$_2$), 167.1 (quat., Gly-CO), 169.6

(quat., P-CON), 170.9 (quat., Gluα-CO) and 172.7 (quat., Gluγ-CO); m/z (FAB+) 662.2536 (MH$^+$.C$_{35}$H$_{40}$N$_3$O$_8$S requires 662.2536).

1.1.39. Glycyl-L-thia-5,5-dimethylprolyl-L-glutamic acid 49

Protected tripeptide 57 (0.44 g, 0.66 mmol) was dissolved in methanol:water (4:1, 50 cm$^3$), placed in a Parr bottle. The vessel was flushed with nitrogen, 10% palladium on activated carbon (70 mg, 0.066 mmol) was added and the mixture was pressurized to 40 p.s.i with hydrogen and shaken for 3 h. Further 10% palladium on activated carbon (70 mg) was added and the reaction continued for 21 h. The reaction mixture was filtered through Celite™ washed with methanol: water (4:1) and the solvent removed to yield an oil which by t.l.c and $^1$H NMR analysis contained the desired product and products containing varying amounts of debenzylation. The mixture was dissolved in water and passed through a C$_{18}$ column eluting with water, then 10% methanol:water. The relevant fractions were combined, the solvent removed and the residue was triturated with dry ether to yield tripeptide 49 (0.110g, 48%) as a white solid. Tripeptide 49 was shown to be a 85:15 cis:trans mixture of conformers by $^1$H NMR analysis (the ratio was estimated from the integration of the doublets at δ 4.95 and 5.02 and assigned to the Pα-H protons of the major and minor conformers respectively): mp 145-150° C.; [α]$_D$ −75 (c 0.064 in water); δ$_H$ (300 MHz; D$_2$O) 1.84 (2.55H, s, Pδ-CH$_3$). 1.90* (0.45H, s, Pδ-CH$_3$) 1.93 (3H, s, Pδ-CH$_3$), 1.96-2.05 (1H, m, Gluβ-H$_A$H$_B$), 2.18-2.27 (1H, m, Gluβ-H$_A$H$_B$), 2.42 (2H, t, J 7.5, Gluγ-H$_2$), 3.36 (1H, d, J 12.7, PP-H$_A$H$_B$) 3.59 (1H, dd, J 12.8 and 6.4, P-H$_A$H$_B$), 3.70 (1H, d, J 16.2, Glyα-H$_A$H$_B$), 4.01 (1H, d, J 16.3, Glyα-CH$_A$H$_B$), 4.23* (0.15H, dd, J 9.1 and 4.9, Gluα-H), 4.32 (0.85H, dd, J 9.1 and 4.9, Gluα-H), 4.95 (0.85H, d, J 6.2, Pα-H) and 5.02* (0.15H, d, J 6.0, Pα-H); δ$_C$ (75 MHz; D$_2$O) 26.1* (CH$_3$, Pδ-CH$_3$), 26.3 (CH$_3$, Pδ-CH$_3$), 26.56 (CH$_2$, Gluβ-C), 27.6 (CH$_3$, Pδ-CH$_3$), 27.9* (CH$_3$, Pδ-CH$_3$), 31.1 (CH$_2$, Gluγ-C), 30.3* (CH$_2$, Gluγ-C), 32.1 (CH$_2$, Pβ-C), 32.3* (CH$_2$, Pβ-C), 41.1* (CH$_2$, Glyα-C), 41.6 (CH$_2$, Glyα-C), 54.4 (CH, Gluα-C), 55.0* (CH, Gluα-C), 65.3* (CH, Pα-H), 65.5 (CH, Pα-H), 74.3* (quat., Pδ-C), 74.6 (quat., Pδ-C), 164.4* (quat., Gly-CO), 164.6 (quat., Gly-CO), 170.5 (quat., P-CON), 170.8* (quat., P-CON), 176.9 (quat., Gluα-CO) and 178.3 (quat., Gluγ-CO); m/z (FAB+) 348.1249 (MH$^+$.C$_{12}$H$_{22}$N$_3$O$_6$S requires 348.1229).

1.1.40. Methyl N-tert-Buyltoxycarbonylglycyl-(D,L)-5,5-dimethylprolinate 54

Trifluoroacetic acid (1 cm$^3$) was added to a stirred solution of carbamate 43 (0.584 g, 2.27 mmol) in dichloromethane (6 cm$^3$). The solution was stirred for 2 h after which time the volatiles were removed in vacuo and traces of trifluoroacetic acid were removed by placing the sample on an oil pump for 2 h. The salt was then dissolved in dichloromethane (20 cm$^3$) and diisopropylethylamine (1.3 cm$^3$, 7.49 mmol) was added (white fumes) followed by N-tert-butyloxycarbonylglycine 17 (0.477 g, 2.73 mmol) and bis(2-oxo-3-oxazolidinyl)phosphinic chloride (0.691 g, 2.28 mmol). Additional dichloromethane (5 cm$^3$) was added and the solution was stirred overnight under nitrogen. The solvent was then removed in vacuo, the residue was dissolved in ethyl acetate and washed sequentially with 2 M aqouves hydrochloric acid, saturated sodium hydrogen carbonate and dried (MgSO$_4$). Removal of the solvent gave an oil (0.440g) that was purified by chromatography (silica gel, hexane:ethyl acetate, 2:1, then 1:1) to give dipeptide 54 (0.368 g, 52%) as a colourless oil. Dipeptide 54 was shown to be 80:20 cis:trans mixture of conformers by $^1$H NMR analysis (the ratio was estimated from the integration of the chemical shifts at 6 4.28 and 4.46 assigned to the Proα-H protons of the major and minor conformers respectively): δ$_H$ (300 MHz; CDCl$_3$) 1.26 (2.4H, s, Proδ-CH$_3$), 1.28 [9H, s, C(CH$_3$)$_3$], 1.31* (0.6H, s, Proδ-CH$_3$), 1.44* (0.6H, s, Proδ-CH$_3$), 1.46 (2.4H, s, Proδ-CH$_3$), 1.59-2.15 (4H, m, Proβ-H$_2$, Proγ-H$_2$), 3.37 (0.8H, dd, J 16.7 and 3.3, Glyα-H$_A$H$_B$), 3.57* (0.6H, s, Proα-CO$_2$CH$_3$), 3.61 (2.4H, s, Proδ-CO$_2$CH$_3$), 3.74 (0.8H, dd, J 16.7 and 3.3, Glyα-H$_A$H$_B$), 3.84* (0.2H, dd, J 16.9 and 3.9, Glyα-H$_A$H$_B$), 3.39-4.01* (0.2H, m, Glyα-H$_A$H$_B$), 4.28 (0.8H, d, J 8.3, Proα-H), 4.46* (0.2H, dd, J 8.0 and 2.2, Proα-H) and 5.40 (1H, br s, 1H, Gly-NH); δ$_H$ (75 MHz; CDCl$_3$) 24.5 (CH$_3$, Proδ-CH$_3$), 25.0* (CH$_2$, Proβ-C), 26.1 (CH$_3$, Proδ-CH$_3$), 26.9* (CH$_3$, Proδ-CH$_3$), 27.2* (CH$_3$, Proδ-CH$_3$), 27.4 (CH$_2$, Proβ-C), 27.9 [CH$_3$, C(CH$_3$)$_3$], 38.9 (CH$_2$, Proγ-C), 41.7* (CH$_2$, Proγ-C), 42.8* (CH$_2$, Glyα-C), 43.1 (CH$_2$, Glyα-C), 51.7* (CH$_3$, Proα-CO$_2$CH$_3$), 52.3 (CH$_3$, Proα-CO$_2$CH$_3$), 60.1 (CH, Proα-C), 60.9* (quat., Proδ-C), 61.7* (CH, Proα-C), 63.8 (CH, Proα-C), 78.0 [quat., C(CH$_3$)$_3$], 155.3 (quat., NCO$_2$), 155.4* (quat., NCO$_2$), 166.5 (quat., Gly-CO), 167.7* (quat., Gly-CO), 171.9 (quat., Proα-CO) and 172.4* (quat., Proα-CO); m/z (CI+) 315.1927 (MH$^+$.C$_{15}$H$_{27}$N$_2$O$_5$ requires 315.1920).

1.1.41. N-tert-Butoxycarbonylglycyl-(D,L)-5,5-dimethylproline 55

To a solution of dipeptide 54 (0.362 g, 1.16 mmol) in dioxane (12 cm$^3$) was added 1 M aqueous sodium hydroxide (5.91 cm$^3$, 5.91 mmol) and the mixture stirred for 21 h. The reaction was acidified with solid citric acid and the product was extracted with ethyl acetate. The combined organic extracts were washed with brine, dried (MgSO$_4$) and the solvent removed in vacuo to yield an oil which was purified by chromatography (silica gel, hexane:ethyl acetate, 2:1, 1:1, 4:6), to give acid 55 (0.324 g, 94%) as a white foam which liquified rapidly. Acid 55 was shown to be an 80:20 cis:trans mixture of conformers by $^1$H NMR analysis (the ratio was estimated from the integration of the broad singlets at δ 5.81 and 5.66 assigned to the GlyN-H protons of the major and minor conformers respectively): δ$_H$ (300 MHz; CDCl$_3$) 1.40 (2.4H, s, Proδ-CH$_3$), 1.43 [7.2H, s, C(CH$_3$)$_3$], 1.44* [1.8H, s, C(CH$_3$)$_3$], 1.47* (0.6H, s, Proδ-CH$_3$), 1.58 (0.6H, s, Proδ-CH$_3$), 1.61 (2.4H, s, Proδ-CH$_3$), 1.74-2.33 (4H, m, Proβ-H$_2$, Proγ-H$_2$), 3.37 (0.8H, dd, J 16.7 and 3.3, Glyα-H$_A$H$_B$), 3.65 (0.8H, dd, J 16.8 and 3.6, Glyα-H$_A$H$_B$), 3.96 (1H, dd, J 16.9 and 3.9, Glyα-H$_A$H$_B$, Glyα-H$_A$H$_B$* partially obscured), 4.21* (0.2H, dd, J 17.0 and 5.9, Glyα-H$_A$H$_B$), 4.42 (0.8H, d, J 7.2, Proα-H), 4.67* (0.2H, d, J 7.9 Proα-H), 5.66* (0.2H, br s, Gly-NH), 5.81 (0.8H, br s, Gly-NH) and 6.2 (1H, br s, OH); H (75 MHz; CDCl$_3$) 24.8 (CH$_3$, Proδ-CH$_3$), 25.1* (CH$_2$, Proβ-C), 26.3 (CH$_3$, Proδ-CH$_3$), 27.1* (CH$_3$, Proδ-CH$_3$), 27.6* (CH$_3$, Proδ-CH$_3$), 28.0 (CH$_2$, Proβ-C), 28.2 [CH$_3$, C(CH$_3$)$_3$], 39.2 (CH$_2$, Proγ-C), 42.0* (CH$_2$, Proγ-C), 43.0* (CH$_2$, Glyα-C), 43.5 (CH$_2$, Glyα-C), 60.5 (CH, Proα-C), 61.8* (quat., Proδ-C), 62.2* (CH, Proα-C), 64.3 (CH, Proα-C), 79.7* [quat., C(CH$_3$)$_3$], 80.2 [quat., C(CH$_3$)$_3$], 156.0* (quat., NCO$_2$), 156.4 (quat., NCO$_2$), 166.8 (quat., Gly-CO), 169.5* (quat., Gly-CO), 173.9 (quat., Proα-CO) and 174.5* (quat., Proα-CO); m/z (CI+) 315.1927 (MH$^+$.C$_{15}$H$_{27}$N$_2$O$_5$ requires 315.1920).

1.1.42. Dibenzyl N-tert-butoxycarbonylglycyl-(D,L)-5,5-dimethylprolyl-L-glutamate 58

To a stirred solution of acid 55 (0.298 g, 1 mmol) in dry dichloromethane (40 cm$^3$) was added successively diisopropylethylamine (0.453 cm$^3$, 2.6 mmol), L-glutamic acid dibenzyl ester p-toluenesulphonate 28 (0.648 g, 1.3 mmol) and bis(2-oxo-3-oxazolidinyl)phosphinic chloride (0.330 g, 1.3 mmol). The resultant solution was stirred at room temperature under nitrogen overnight and the solvent removed. The residue was dissolved in ethyl acetate, washed with 10% aqueous citric acid solution, saturated sodium hydrogen carbonate, brine and dried (MgSO$_4$). The solvent was evaporated and the product purified by chromatography (silica gel, hexane:ethyl acetate, 1:1) to give protected tripeptide 58 (0.408 g, 67%) as a yellow oil (1:1 mixture of Proα-C epimers). Tripeptide 58 was shown to be 85:15 cis:trans mixture of conformers by $^1$H NMR analysis (the ratio was estimated from the integration of the chemical shifts at δ 5.31-5.38 and 5.48 assigned to the Gly-NH protons of the major and minor conformers respectively): δ (300 MHz; CDCl$_3$) 1.41 [9H, s, C(CH$_3$)$_3$], 1.44 (2.55H, s, Proδ-CH$_3$), 1.52* (0.45H, s, Proδ-CH$_3$), 1.54* (0.45H, s, Proδ-CH$_3$), 1.64 (2.55H, s, Proδ-CH$_3$), 1.67 (2.55H, s, Proδ-CH$_3$), 1.70-2.24 (6H, m, Proβ-H$_2$, Proγ-H$_2$, Gluβ-H$_2$), 2.35-2.45 (2H, m, Gluγ-H$_2$), 3.58-3.69 (0.85H, m, Glyα-H$_A$H$_B$), 3.85 (0.85H, m, Glyα-H$_A$H$_B$), 3.88-3.98* (0.15H, m, Glyα-H$_A$H$_B$), 4.12-4.17* (0.15H, m, Glyα-H$_A$H$_B$), 4.20-4.31 (1H, m, Proα-H), 4.59-4.71 (1H, m, Gluα-H), 5.10-5.22 (m, 4H, 2×OCH$_2$Ph), 5.31-5.38 (0.85H, m, Gly-NH) and 5.48* (0.15H, m, Gly-NH); δ$_C$ (75 MHz; CDCl$_3$) 24.38 (CH$_3$, Proδ-CH$_3$), 24.46 (CH$_3$, Proδ-CH$_3$), 25.1* (CH$_2$, Proβ-C), 25.2* (CH$_2$, Proβ-C), 26.2 (CH$_2$, Gluβ-C), 26.3 (CH$_2$, Gluβ-C), 26.6 (CH$_3$, Proδ-CH$_3$), 26.8* (CH$_2$, Proβ-C), 27.0* (CH$_3$, Proδ-CH$_3$), 27.1* (CH$_3$, Proδ-CH$_3$), 27.9* (CH$_3$, Proδ-CH$_3$), 28.2 [CH$_3$, C(CH$_3$)$_3$], 28.5 (CH$_2$, Proβ-C), 28.8 (CH$_2$, Proβ-C), 30.05* (CH$_2$, Gluγ-C), 30.1* (CH$_2$, Gluγ-C), 30.2 (CH$_2$, Gluγ-C), 30.25 (CH$_2$, Gluγ-C), 38.9 (CH$_2$, Proγ-C), 39.1 (CH$_2$, Proγ-C), 42.4** (CH$_2$, Proγ-C), 43.1* (CH$_2$, Glyα-C), 43.3* (CH$_2$, Glyα-C), 43.5 (CH$_2$, Glyα-C), 43.6 (CH$_2$, Glyα-C), 51.7* (CH, Gluα-C), 52.0 (CH, Gluα-C), 52.1 (CH, Gluα-C), 61.5* (quat., Proδ-C), 61.6* (quat., Proδ-C), 61.9 (CH, Proα-C), 62.0 (CH, Proα-C), 63.0* (CH, Proα-C), 63.05* (CH, Proα-C), 64.3 (quat., Proδ-C), 64.3 (quat., Proδ-C), 66.3* (CH$_2$, OCH$_2$Ph), 66.4* (CH$_2$, OCH$_2$Ph), 66.41 (CH$_2$, OCH$_2$Ph), 66.5 (CH$_2$, OCH$_2$Ph), 67.0* (CH$_2$, OCH$_2$Ph), 67.1* (CH$_2$, OCH$_2$Ph), 67.21 (CH$_2$, OCH$_2$Ph), 67.24 (CH$_2$, OCH$_2$Ph), 79.3 [quat., C(CH$_3$)$_3$], 128.1 (CH, Ph), 128.2 (CH, Ph), 128.3 (CH, Ph), 128.4* (CH, Ph), 128.43 (CH, Ph), 128.5 (CH, Ph), 135.03 (quat., Ph), 135.07, (quat., Ph), 153.13* (quat., Ph), 135.18* (quat., Ph), 135.6 (quat., Ph), 135.7* (quat., Ph), 155.8* (quat., NCO$_2$), 155.9 (quat., NCO$_2$), 156.0 (quat., NCO$_2$), 167.6 (quat., Gly-CO), 167.7 (quat., Gly-CO), 168.8* (quat., Gly-CO), 169.3* (quat., Gly-CO), 171.1 (quat., Pro-CON), 171.3* (quat., Pro-CON), 171.4* (quat., Pro-CON), 171.6 (quat., Gluα-CO), 171.8 (quat., Gluα-CO), 172.4 (quat., Gluγ-CO), 172.5* (quat., Gluγ-CO) and 172.6 (quat., Gluγ-CO); m/z (EI+) 609.3035 (M$^+$.C$_{33}$H$_{43}$N$_3$O$_8$ requires 609.3050).

1.1.43. Glycyl-(D,L)-5,5-dimethylprolyl-L-glutamic acid 50

To a stirred solution of protected tripeptide 58 (0.276 g, 0.454 mmol) in dichloromethane (10 cm$^3$) was added trifluoroacetic acid (1 cm$^3$) and the mixture stirred for 75 min. The solvent was removed in vacuo, the residue was dissolved in saturated sodium hydrogen carbonate and the product extracted with ethyl acetate. The combined organic layers were washed with brine, dried (MgSO$_4$) and the solvent removed to yield an oil (0.244g) which was dissolved in methanol:water (4:1, 50 cm$^3$). The flask was flushed with nitrogen, 10% palladium on activated carbon (0.048 mg, 0.454 mmol) was added and the mixture was then stirred overnight under 1 atmosphere of hydrogen. Filtration through Celite™ followed by removal of the solvent yielded an oil that was triturated with dry diethyl ether to yield tripeptide 50 (0.139 g, 93%) as an off white solid. Tripeptide 50 was shown to be a 72:28 cis:trans mixture of conformers by $^1$H NMR analysis (the ratio was estimated from the integration of the chemical shifts at δ 3.57 and 4.15-4.16 assigned to the Glyα-H protons of the major and minor conformers respectively). Approximately 10% of the final product was tentatively assigned as the hydrochloride salt**: mp 145-150° C.; δ$_H$ (400 MHz; D$_2$O) 1.43 (2.16H, s, Proδ-CH$_3$), 1.49* (0.84H, s, Proδ-CH$_3$), 1.57* (0.84H, s, Proδ-CH$_3$), 1.58* (0.84H, s, Proδ-CH$_3$), 1.60 (2.16H, s, Proδ-CH$_3$), 1.61 (2.16H, s, Proδ-CH$_3$), 1.90-2.48 (8H, m, Proβ-H$_2$, Proγ-H$_2$, Gluβ-H$_2$, Gluγ-H$_2$), 3.57 (0.72H, dd, J 16.1 and 2.8, Glyα-H$_A$H$_B$), 3.75-3.82 (0.2H, m, Glyα-H$_A$H$_B$, Gluα-H), 3.94 (0.72H, dd, J 16.1 and 6.5, Glyα-H$_A$H$_B$), 4.11 (0.1H, d, J 2.5, Glyα-H$_A$H$_B$), 4.15-4.16* (0.56H, m, Glyα-H$_2$), 4.24-4.30 (1H, m, Gluα-H), 4.46-4.51** (0.1H, m, Proα-H), 4.60 (0.72H, t, J 10.1, Proα-H) and 4.68* (0.28H, dd, J 13.5 and 4.3, Proα-H); δ$_C$(400 MHz; D$_2$O) 23.56 (CH$_3$, Proδ-CH$_3$), 23.76 (CH$_3$, Proδ-CH$_3$), 24.1 (CH$_3$, Proδ-CH$_3$), 25.0 (CH$_2$, Gluβ-C), 25.2 (CH$_3$, Proδ-CH$_3$), 25.6 (CH$_2$, Gluβ-C), 25.7 (CH$_3$, Proδ-CH$_3$), 26.0 (CH$_2$, Gluβ-C), 26.1* (CH$_3$, Proδ-CH$_3$), 26.2* (CH$_3$, Proδ-CH$_3$), 26.4 (CH$_2$, Gluβ-C), 26.8* (CH$_2$, Gluβ-C), 28.4, (CH$_2$, Proβ-C), 28.7, (CH$_2$, Proβ-C), 30.8* (CH$_2$, Gluγ-C), 31.0* (CH$_2$, Gluγ-C), 31.2 (CH$_2$, Gluγ-C), 38.7 (CH$_2$, Proγ-C), 38.8 (CH$_2$, Proγ-C), 40.6* (CH$_2$, Glyα-C), 40.7 (CH$_2$, Glyα-C), 40.8 (CH$_2$, Glyα-C), 41.1* (CH$_2$, Proγ-C), 41.2* (CH$_2$, Proγ-C), 46.1** (CH$_2$, Glyα-C), 54.1 (CH, Gluα-C), 54.5 (CH, Gluα-C), 59.7* (CH, Proα-C), 61.7 (CH, Proα-C), 61.8 (CH, Proα-C), 62.6** (quat., Proδ-C), 62.7* (quat., Proδ-C), 63.4* (CH, Proα-C), 63.9** (quat., Proδ-C), 65.0 (quat., Proδ-C), 65.1 (quat., Proδ-C), 164.8 (quat., Gly-CO), 164.9 (quat., Gly-CO), 165.6* (quat., Gly-CO), 165.8* (quat., Gly-CO), 166.0 (quat., Gly-CO), 172.3 (quat., Pro-CON), 172.8 (quat., Pro-CON), 173.1 (quat., Pro-CON), 173.3* (quat., Pro-CON), 173.6* (quat., Pro-CON), 176.9 (quat., Gluα-CO), 177.3 (quat., Gluα-CO) and 178.1 (quat., Gluγ-CO); m/z (FAB+) 330.1666 (MH$^+$.C$_{14}$H$_{24}$N$_3$O$_6$ requires 330.1666).

In summary we synthesised new analogues of GPE. In five of these analogs the trans conformation about the Gly-Pro* bond was stabilized by either the presence of a hydrophobic alkyl group at C-2 on the proline (compounds 1-5) or by a spirolactam bridge between the 2-position of the proline and the nitrogen of the glutamate (compounds 35 and 36). In contrast, dimethylation at C-5 on the proline destabilises the trans conformation resulting in an increased population of the cis conformer (compounds 49 and 50). These GP*E mimetics are valuable tools to provide information about the influence of the proline residue on the bioactivity of the parent peptide GPE.

Example 2

Synthesis of analog 60 (Glycyl-trans-4-hydroxy-L-prolyl-L-glutamic Acid (GhypE))

Scheme 1 Reagents, conditions and yields:

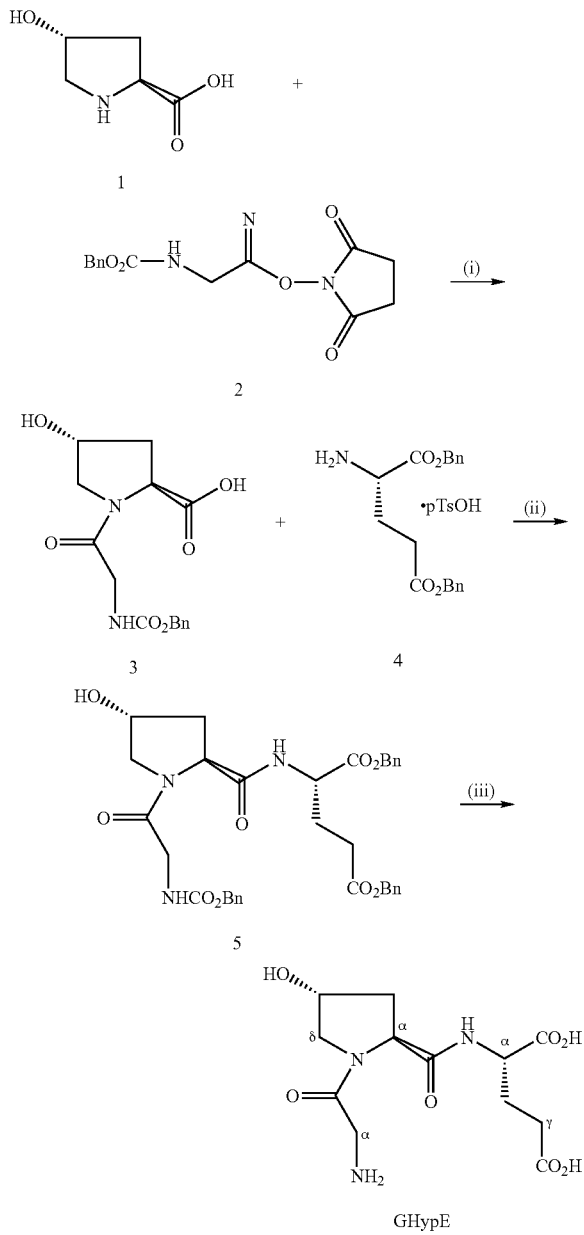

(i) NaHCO$_3$, H$_2$O, DME, RT, 20 h (70%); (ii) EDCl•HCl, HOBt, Et$_3$N, CH$_2$Cl$_2$, 0° C. to RT, 20h (71%); (iv) H$_2$, 10% Pd/C, 20% H$_2$O/MeOH, RT, 20h (80%).

Experimental

Flash chromatography was performed using Scharlau 60 (40-60 pm mesh) silica gel. Analytical thin layer chromatography was carried out on 0.20 mm pre-coated silica gel plates (ALUGRAM® SL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$g$^{-1}$. Samples were prepared in the solvent indicated at the concentration specified (measured in g/100 cm$^3$).

NMR spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($\delta_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($\delta_C$), degree of hybridization as determined by DEPT experiments, and assignment. $^1$H NMR spectra were referenced internally using SiMe$_4$ ($\delta$ 0.00) or CDCl$_3$ ($\delta$ 7.26). $^{13}$C NMR spectra were referenced internally using CDCl$_3$ ($\delta$ 77.0) or externally on DSS (3-(trimethylsilyl)-1-propanesulfonic acid, sodium salt). When two sets of peaks arise in the NMR spectra due to different conformations around the glycine-proline amide bond, the chemical shift for the minor cis conformer is asterisked (*).

Accurate mass measurements were recorded on a VG-70SE mass spectrometer. Hexane and dichloromethane were distilled prior to use. Methanol was dried using magnesium turnings and iodine, and distilled under nitrogen. Triethylamine was dried over calcium hydride and distilled under nitrogen. L-Glutamic acid dibenzyl ester p-toluenesulphonate 4 was purchased from Bachem. Bis(2-oxo-3-oxazolidinyl)phosphinic chloride (BoPCl) (97%) was purchased from Fluka. Trans-4-Hydroxy-L-proline 1 and 10% palladium on activated carbon were purchased from Aldrich Chemical Company.

2.1 N-Benzyloxycarbonylglycyl-trans-4-hydroxy-L-proline 3 trans-4-Hydroxy-L-proline 1 (0.28 g, 2.13 mmol) and sodium hydrogen carbonate (0.18 g, 2.13 mmol) were dissolved in water (3 cm$^3$) at room temperature. N-benzyloxycarbonyl-glycyl-N-hydroxysuccinimide 2 (0.44 g, 1.44 mmol) in dimethoxyethane (3 cm$^3$) was added dropwise over a period of 5 min. The solution was stirred for 2.5 then acidified with conc. hydrochloric acid (38%) to pH 1. The solution was placed in a refrigerator overnight. Ethyl acetate (2×20 cmr$^3$) was added and the resulting organic layers dried (MgSO$_4$), filtered and evaporated under reduced pressure to yield a light pinky foam, which was purified by flash column chromatography (10% methanol/methylene chloride) to produce acid 3 (0.32 g, 70%) as a clear foam. Acid 3 was shown to be an 77:23 trans:cis mixture of conformers by $^1$H NMR analysis (the ratio was estimated from the integration of the signals at ($\delta$ 4.33-4.38 and 4.52-4.54, assigned to the Proα-H of the major and minor conformers respectively): [α]$_D$ −75.5 (c 0.08 in MeOH); OH (300 MHz; CD$_3$OD) 1.89-1.94 (0.77H, m, Proβ-H$_A$H$_B$), 2.08-2.14 (1H, m, Proβ-H$_A$H$_B$), 2.14-2.16* (0.23H, m, Proβ-H$_A$H$_B$), 3.17-3.20 (1H, m, Proδ-H$_A$H$_B$), 3.53-3.57 (1H, m, Proδ-H$_A$H$_B$), 3.73-3.78 (1H, d, J 17.1, Glyα-H$_A$H$_B$), 3.87-3.93 (1H, d, J 17.1, Glyα-H$_A$H$_B$), 4.20-4.30* (0.23H, m, Proγ-H), 4.33-4.38 (1.54H, m, Proγ-H and Proα-H), 4.52-4.54* (0.23H, t, J 7.0, Proα-H) 4.94 (2H, s, OCH$_2$Ph) and 7.11-7.23 (5H, m, Ph); δ$_C$ (75 MHz, CD$_3$OD) 39.0 (CH$_2$, Proβ-C), 41.3* (CH$_2$, Pro-C), 44.2* (CH$_2$, Proδ-C), 44.8 (CH$_2$, Proδ-C), 55.9 (CH$_2$, Glyα-C), 56.2* (CH$_2$, Glyα-C), 59.5* (CH, Proα-C), 60.1 (CH, Proα-C), 68.5 (CH$_2$, OCH$_2$Ph), 68.7* (CH$_2$, OCH$_2$Ph), 69.7* (CH, Proγ-C), 71.7 (CH, Proγ-C), 129.6 (CH, Ph), 129.7 (CH, Ph), 130.2 (CH, Ph), 138.9 (quat., Ph), 159.6 (quat., NCO$_2$), 170.1 (quat., Gly-CO), 171.6* (quat., Gly-CO), 175.9* (quat., CO$_2$H) and 176.3 (quat., CO$_2$H),; m/z (FAB+) 323.1240 (M$^+$.C$_{16}$H$_{20}$N$_2$O$_5$ requires 320.1243).

2.2 Dibenzyl-N-benzyloxycarbonylglycyl-trans-4-hydroxy-L-prolyl-L-glutamate 5

Acid 3 (0.70 g, 2.18 mmol), L-glutamic acid dibenzyl ester p-toluenesulphonate 4 (1.19 g, 2.40 mmol), 1-hydroxybenzotriazole hydrate (0.37 g, 2.40 mmol) and 1-ethyl-3-(3-dimethylaminopropyl)carbodiimide hydrochloride (0.46 g, 2.40 mmol) were dissolved in dichloromethane (60 cm$^3$) under nitrogen and cooled to 0° C. Triethylamine (0.60 cm$^3$, 4.30 mmol) was added dropwise over a period of 5 min. The solution was stirred for 1.5 h, then allowed to warm to room temperature and stirred overnight. Dichloromethane (40 cm$^3$) was added and the organic layer washed successively with saturated sodium hydrogen carbonate solution (25 cm$^3$) and aqueous 2M citric acid (25 cm$^3$), then dried (MgSO$_4$), filtered and evaporated under reduced pressure to form a white gummy solid, which was purified by flash column chromatography (10% methanol/ethyl acetate) to produce fully protected tripeptide 5 (0.97 g, 71%) as a white solid. Tripeptide 5 was shown to be an 91:9 trans:cis mixture of conformers by $^1$H NMR analysis (the ratio was estimated from the integration of the broad signals at δ 5.89 and 6.51, assigned to the Gly-NH of the major and minor conformers respectively): m.p. 124-126° C.; [α]$_D$ −57.7 (c 0.07 in MeOH); δ$_H$ (300 MHz; CDCl$_3$; Me$_4$Si) 2.08-2.18 (4H, m, Gluβ-H$_2$ and Proβ-H$_2$), 2.44-2.46 (2H, m, Gluγ-H$_2$), 3.43-3.62 (2H, m, Proδ-H$_2$), 3.75-4.03 (2H, m, Glyα-H$_2$), 4.40-4.50 (1H, m, Gluα-H), 4.53-4.56 (2H, m, Proα-H and Proγ-H), 5.04 (2H, s, OCH$_2$Ph), 5.05 (2H, s, OCH$_2$Ph), 5.10 (2H, s, OCH$_2$Ph), 5.89 (0.91H, br s, Gly-NH), 6.51* (0.09H, br s, Gly-NH), 7.30-7.40 (15H, m, 3×Ph), 7.51 (0.91H, d, J 7.4, Glu-NH) and 7.64* (0.09H, br s, Glu-NH); δ$_C$ (75 MHz, CDCl$_3$) 27.3 (CH$_2$, Gluβ-C), 30.4 (CH$_2$, Proβ-C), 30.7* (CH$_2$, Proβ-C), 37.5 (CH$_2$, Gluγ-C), 43.7 (CH$_2$, Glyα-C), 52.2 (CH, Gluα-C), 54.8 (CH$_2$, Proδ-C), 55.8* (CH$_2$, Proδ-C), 59.0* (CH, Proα-C), 59.3 (CH, Proα-C), 66.8 (CH$_2$, OCH$_2$Ph), 67.3 (CH$_2$, OCH$_2$Ph), 67.7 (CH$_2$, OCH$_2$Ph), 68.7* (CH, Proγ-C), 70.5 (CH, Proγ-C), 128.3 (CH, Ph), 128.5 (CH, Ph), 128.6 (CH, Ph), 128.8 (CH, Ph), 128.9 (CH, Ph), 135.6 (quat., Ph), 135.9 (quat., Ph), 136.1 (quat., Ph), 157.0 (quat., NCO$_2$), 168.7 (quat., Gly-CO), 169.6* (quat., Gly-CO), 171.8 (quat., Pro-CON) and 173.2 (quat., Gluγ-CO and Gluα-CO); m/z (FAB+) 632.2613 (M$^+$.C$_{34}$H$_{38}$N$_3$O$_9$ requires 632.2608).

2.3 Glycyl-trans-4-hydroxy-L-prolyl-L-glutamic acid (GHypE) 60

A mixture of protected tripeptide 5 (0.50 g, 0.79 mmol) and 10% palladium on activated carbon (0.08 g, 0.08 mmol) in 20% water/methanol (100 cm$^3$) was stirred under an atmosphere of hydrogen at room temperature for 20 h. The solution was filtered through a Celite™ pad, washed with methanol (60 cm$^3$) and the filtrate evaporated to dryness to form a clear gum. This gum was dissolved in methanol (30 cm$^3$) and refiltered through a Celite™ pad. The solution was evaporated to dryness to form a clear gum. The gum was placed on a vacuum line for 15 min and then triturated with anhydrous diethyl ether to form GHypE (0.20 g, 80%) as a white solid. GHypE was shown to be an 80:20 trans:cis mixture of conformers by $^{13}$C NMR analysis (the ratio was estimated from the integration of the signals at δ 70.2 and 68.5, assigned to the Proγ-C of the major and minor conformers respectively): mp 158-160° C.; [α]$_D$ −58.1 (c 0.1 in MeOH); δ$_H$ (300 MHz; D$_2$O) 1.96-2.23 (4H, m, Gluβ-H$_2$ and Proβ-H$_2$), 2.48-2.56 (2H, m, Gluγ-H$_2$), 3.62 (2H, d, J 10.0, Glyα-H$_2$), 3.80 (1H, dd, J 8.8 and 4.9, Gluα-H), 4.08 (1H, dd, J 10.4 and 2.6, Proα-H), 4.30-4.35 (2H, m, Proδ-H$_2$) and 4.63-4.69 (1H, m, Proγ-H); δ$_C$ (75 MHz, D$_2$O) 29.2 (CH$_2$, Gluβ-C), 31.7 (CH$_2$, Proβ-C), 32.3* (CH$_2$, Proβ-C), 37.6 (CH$_2$, Gluγ-C), 40.0* (CH$_2$, Glyα-C), 41.0 (CH$_2$, Glyα-C), 54.8 (CH$_2$, Proδ-C), 55.3 (CH, Gluα-C), 59.1* (CH, Proα-C), 59.7 (CH, Proα-C), 68.5* (CH, Proγ-C), 70.2 (CH, Proγ-C), 166.4 (quat., Gly-CO), 167.1* (quat., Gly-CO), 173.0* (quat., Pro-CON), 173.4 (quat., Pro-CON), 177.9 (quat., Gluα-CO) and 179.2 (quat., Gluγ-CO); m/z (FAB+) 318.1329 (MH$^+$.C$_{17}$H$_{20}$NO$_5$ requires 318.1342).

Example 3

Synthesis of analog 61 (Glycyl-L-2-Pyroglutamyl-L-Glutamic Acid Hydrochloride (GPyroE.HCl))

General experimental description as in Example 2 above. L-Pyroglutamic acid was purchased from Acros Organics. L-Glutamic acid dibenzyl ester p-toluenesulphonate was purchased from Bachem. Tert-Butyl acetate was purchased from Lancaster Chemical Co. Bis(2-oxo-3-oxazolidinyl)phosphinic chloride (97%) was purchased from Fluka. 10% Palladium on activated carbon was purchased from Aldrich Chemical Company.

Scheme 1 Reagents, conditions and yields:

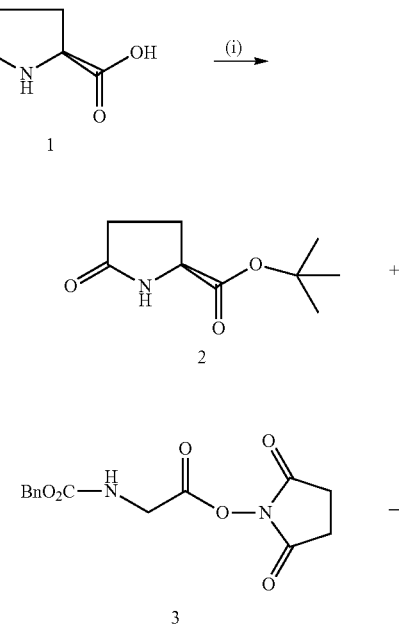

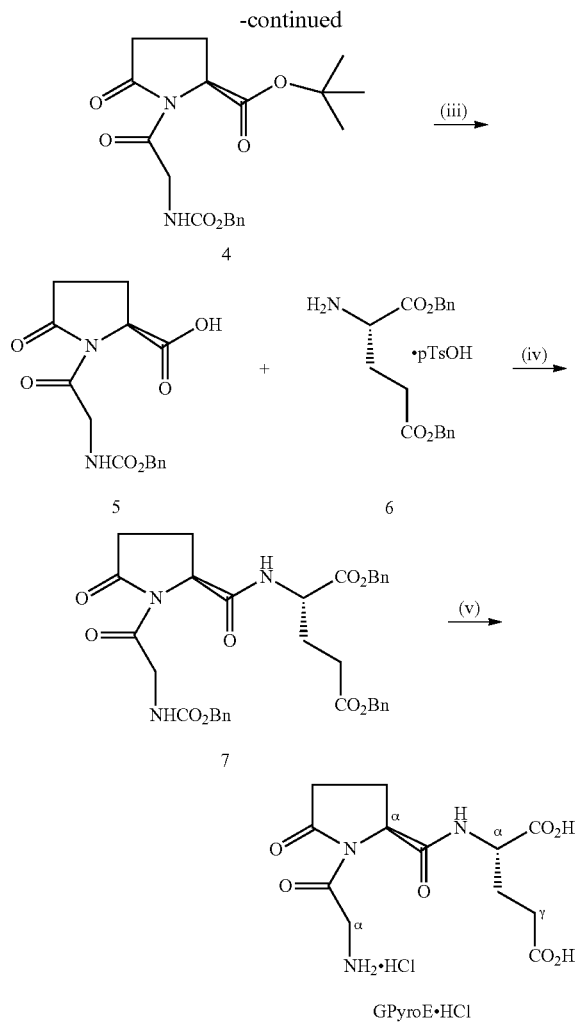

(i) 70% HClO₄, tert-butyl acetate, RT, 20h, (55%); (ii) LiHMDS, THF, -78° C., 1h, (83%); (iii) TFA, CH₂Cl₂, RT 1.5h; (iv) BOPCl, ET₃N, CH₂Cl₂, 0° C. to RT, 20h, (78%); (v) H₂, 10% Pd/C, c•HCl, 20% H₂O/THF, RT, 4h, (74%).

3.1 tert-Butyl-L-pyroglutamate 2

70% Perchloric acid (0.85 cm³, 9.90 mmol) was added dropwise to a solution of L-pyroglutamic acid 1 (1.70 g, 13.20 mmol) in tert-butyl acetate (17.0 cm³, 126.20 mmol) at room temperature over a period of 5 min. The solution was stirred for 20 h and then solid sodium carbonate was slowly added portionwise until pH 7 was reached. The aqueous layer was extracted with diethyl ether (40 cm³) and ethyl acetate (40 cm³). The combined extracts were dried (MgSO₄), filtered and evaporated under reduced pressure to yield a clear oil, which was purified by flash column chromatography (ethyl acetate) to produce ester 2 (1.33 g, 55%) as a white solid.: mp 101-103° C., lit.[1] mp 102° C.; $[\alpha]_D$ +9.7 (c 0.14 in MeOH), lit.[1] +11 (c 3 in MeOH); $\delta_H$ (200 MHz; CD₃OD) 1.44 [9H, C(CH₃)₃], 2.30-2.39 (4H, m, Pyroβ-H₂ and Pyroγ-H₂), 4.10-4.13 (1H, m, Pyroα-H) and 6.71 (1H, br s, NH); $\delta_C$ (80 MHz; CD₃OD) 24.8 (CH₂, Pyroβ-C), 27.9 [CH₃, C(CH₃)₃], 29.4 (CH₂, Pyroγ-C), 56.1 (CH, Pyroα-C), 82.2 [quat., C(CH₃)₃], 171.2 (quat. Pyro-CO) and 178.3 (quat., Pyro-CONH).

3.2 tert-Butyl-N-benzyloxycarbonylglycyl-L-pyroglutamate 4

Ester 2 (0.61 g, 3.30 mmol) was dissolved in tetrahydrofuran (20 cm³) under nitrogen and cooled to −78° C. Lithium hexamethyldisilazide (1.06 M, 3.30 cm³, 3.50 mmol) was added dropwise over a period of 5 min. The solution was stirred for 15 min, then N-benzyloxycarbonyl-glycyl-N-hydroxysuccinimide[4] 3 (DC89.52)(1.23 g, 4.01 mmol) in tetrahydrofuran (30 cm³) was added and the solution stirred for 45 min. Water (30 cm³) was added and the reaction allowed to warm to room temperature. The resulting aqueous solution was extracted with ethyl acetate (2×50 cm³), dried (MgSO₄), filtered and evaporated under reduced pressure to form a white gummy solid, which was purified by flash column chromatography (ethyl acetate) to produce carbamate 4 (1.04 g, 83%) as a white solid: mp 132-135° C., lit.[2] 134-135° C.; $[\alpha]_D$ −45.5 (c 0.1 in EtOH), lit.[2] −61.7 (c 1.01 in EtOH),; $\delta_H$ (300 MHz; CDCl₃; Me₄Si) 1.47 [9 H, s, C(CH₃)₃], 2.08-2.13 (1H, m, Pyroγ-H$_A$H$_B$), 2.31-2.39 (1H, m, Pyro-H$_A$H$_B$), 2.56 (1H, ddd, J 3.1, 9.2 and 12.3, Pyroγ-H$_A$H$_B$), 2.64-2.73 (1H, m, Pyroγ-H$_A$H$_B$), 4.48 (1H, dd, J 4.8 and 19.6, Glyα-H$_A$H$_B$), 4.61-4.71 (2H, m, Glyα-H$_A$H$_B$ and Pyroα-H), 5.08 (2H, s, OCH₂Ph), 5.47 (1H, s br, Gly-NH) and 7.33 (5H, s, Ph); $\delta_C$ (75 MHz, CDCl₃) 22.3 (CH₂, Pyroγ-C), 28.2 [CH₃, C(CH₃)₃], 31.8 (CH₂, Pyroγ-C), 46.7 (CH₂, Glyα-C), 58.7 (CH, Pyroα-C), 67.3 (CH₂, OCH₂Ph), 83.1 [quat., C(CH₃)₃], 128.4 (CH, Ph), 128.6 (CH, Ph), 129.0 (CH, Ph), 136.8 (quat., Ph), 156.6 (quat., NCO₂), 170.1 (quat., Gly-CON), 170.5 (quat., Pyro-CONH) and 175.1 (quat., Pyro-CO); m/z (FAB+) 377.1698 (MH⁺.C₁₉H₂₅N₂O₆ requires 377.1713).

3.3 tert-Butyl-N-benzyloxycarbonylglycyl-L-pyroglutamic acid 5

Carbamate 4 (0.74 g, 1.97 mmol) was dissolved in dichloromethane (12 cm³) under nitrogen and cooled to 0° C. Trifluoroacetic acid (6 cm³) was added dropwise over a period of 5 min and the solution stirred for 1.5 h. The solution was evaporated under reduced pressure to give an orange gum, that was dissolved in toluene and evaporated under reduced pressure (2×10 cm³) to give crude acid 5 as an orange gum. The material was used without further purification.

3.4 Dibenzyl-N-benzyloxycarbonylglycyl-L-pyroglutamyl-L-glutamate 7

Crude acid 5 (0.63 g, 1.97 mmol), L-glutamic acid dibenzyl ester p-toluenesulphonate 6 (1.18 g, 2.36 mmol) and bis(2-oxo-3-oxazolidinyl)phosphinic chloride (0.60 g, 2.36 mmol) were dissolved in dichloromethane (20 cm³) under nitrogen and cooled to 0° C. Triethylamine (0.64 cm³, 4.60 mmol) was added dropwise over a period of 5 min. The solution was stirred for 1.5 h, then allowed to warm to room temperature and stirred overnight. Dichloromethane (40 cm³) was added and the organic layer washed successively with saturated sodium hydrogen carbonate solution (30 cm³) and aqueous 2M citric acid (30 cm³), then dried (MgSO₄), filtered and evaporated under reduced pressure to form a white gummy solid. Purification by flash column chromatography (ethyl acetate) afforded a white solid. This white solid was washed with diethyl ether (2×15 cm³), filtered to produce fully protected tripeptide 7 (0.98 g, 78%) as a white solid.: m.p. 109-111° C.; $[\alpha]_D$ −55.5 (c 0.25 in MeOH); $\delta_H$ (300 MHz; CDCl₃; Me₄Si) 1.80-2.24 (7H, m, Gluβ-H₂, Gluγ-H₂, Pyroβ-H₂ and Pyroγ-H$_A$H$_B$), 2.74-2.80 (1H, m, Pyroγ-H$_A$H$_B$), 4.38 (1H, dd, J 4.2 and 19.5, Glyα-H$_A$H$_B$), 4.58-4.68

(3H, m, Glyα-H$_A$H$_B$, Proα-H and Gluα-H), 5.08-5.19 (6H, m, 3×OCH$_2$Ph), 5.38 (1H, s br, Gly-NH), 6.84 (1H, d, J 7.7, Glu-NH) and 7.30 (15H, s, 3×Ph); δ$_C$ (75 MHz, CDCl$_3$) 22.2 (CH$_2$, Pyroβ-C), 26.6 (CH$_2$, Gluβ-C), 30.0 (CH$_2$, Gluγ-C), 33.9 (CH$_2$, Pyroγ-C), 46.2 (CH$_2$, Glyα-C), 52.0 (CH, Gluα-C), 58.6 (CH, Pyroα-C), 66.7 (CH$_2$, OCH$_2$Ph), 66.9 (CH$_2$, OCH$_2$Ph), 67.4 (CH$_2$, OCH$_2$Ph), 128.0 (CH, Ph), 128.1 (CH, Ph), 128.2 (CH, Ph), 128.4 (CH, Ph), 128.5 (CH, Ph), 128.6 (CH, Ph), 135.0 (quat., Ph), 135.3 (quat., Ph), 135.6 (quat., Ph), 156.3 (quat., NCO$_2$), 170.2 (quat., Gly-CO), 170.6 (quat., Pyro-CO), 171.2 (quat., Pyro-CO), 172.9 (quat., Glu-CO) and 175.2 (quat., Glu-CO); m/z (FAB+) 630.2460 (MR$^+$.C$_{34}$H$_{36}$N$_3$O$_9$ requires 630.2452).

3.5 Glycyl-L-pyroglutamyl-L-glutamic acid hydrochloride (GPyroE.HCl) 61

A mixture of protected tripeptide 7 (0.45 g, 0.80 mmol), conc. hydrochloric acid (38%, 0.13 cm$^3$) and 10% palladium on activated carbon (0.08 g, 0.08 mmol) in 20% water/tetrahydrofuran (60 cm$^3$) was stirred under an atmosphere of hydrogen at room temperature for 4 h. The solution was filtered through a Celite™ pad, washed with 20% water/tetrahydrofuran (2×30 cm$^3$) and the filtrate evaporated to dryness to form GPyroE.HCl (0.19 g, 74%) as solid. GPyroE.HCl was shown to be exclusively the trans conformer by 1H and $^{13}$C NMR analysis[5]: mp 42-44° C.; [α]$_D$ –57.3 (c 0.09 in MeOH); OH (400 MHz; D$_2$O) 2.07-2.14 (1H, m, Gluβ-H$_A$H$_B$), 2.20-2.25 (1H, m, Gluβ-H$_A$H$_B$), 2.30-2.34 (1H, m, Pyroβ-H$_A$H$_B$), 2.60-2.65 (3H, m, Pyro-H$_A$H$_B$ and Gluγ-H$_2$), 2.74-2.89 (2H, m, Pyroγ-H$_2$), 4.48-4.59 (3H, Glyα-H$_2$ and Gluα-H) and 4.93-4.95 (1H, m, Pyroα-H); δ$_C$ (75 MHz, D$_2$O) 22.5 (CH$_2$, Pyroβ-C), 26.4 (CH$_2$, Gluβ-C), 30.5 (CH$_2$, Gluγ-C), 31.8 (CH$_2$, Pyroγ-C), 44.3 (CH$_2$, Glyα-C), 52.7 (CH, Gluα-C), 59.3 (CH, Pyroα-C), 168.5 (quat., Gly-CO), 173.6 (quat., Pyro-CO), 175.2 (quat., Pyro-CO), 177.6 (quat., Glu-CO) and 178.9 (quat., Glu-CO); m/z (FAB+) 316.1138 (MH$^+$.C$_{12}$H$_{18}$N$_3$O$_7$ requires 316.1145).

References: 1. Besson et al. *Chem. Eur. J.* 2000, 6, 949. 2. Johnson et al. *J. Med. Chem.* 1985, 28, 1596. 3. Li et al. Synth. Comm. 1995, 25, 4045. 4. Succinimide 3 was prepared according to experimental procedure given in the synthesis of analog 66 (G(D,L)PipE). 5. Galardy et al. *Int. J. Pept. Protein Res* 1982, 19, 123.

Example 4

Synthesis of analog 62
(Glycyl-L-Homoprolyl-L-Glutamic Acid (GHomoPE))

General experimental details were as described in Example 2 above. N-benzyloxycarbonyl-glycine, 10% Palladium on activated carbon and bis(2-oxo-3-oxazolidinyl)phosphinic chloride (BoPCl, 97%) were purchased from Aldrich Chem. Co. L-Glutamic acid dibenzyl ester p-toluenesulphonate was purchased from Bachem.

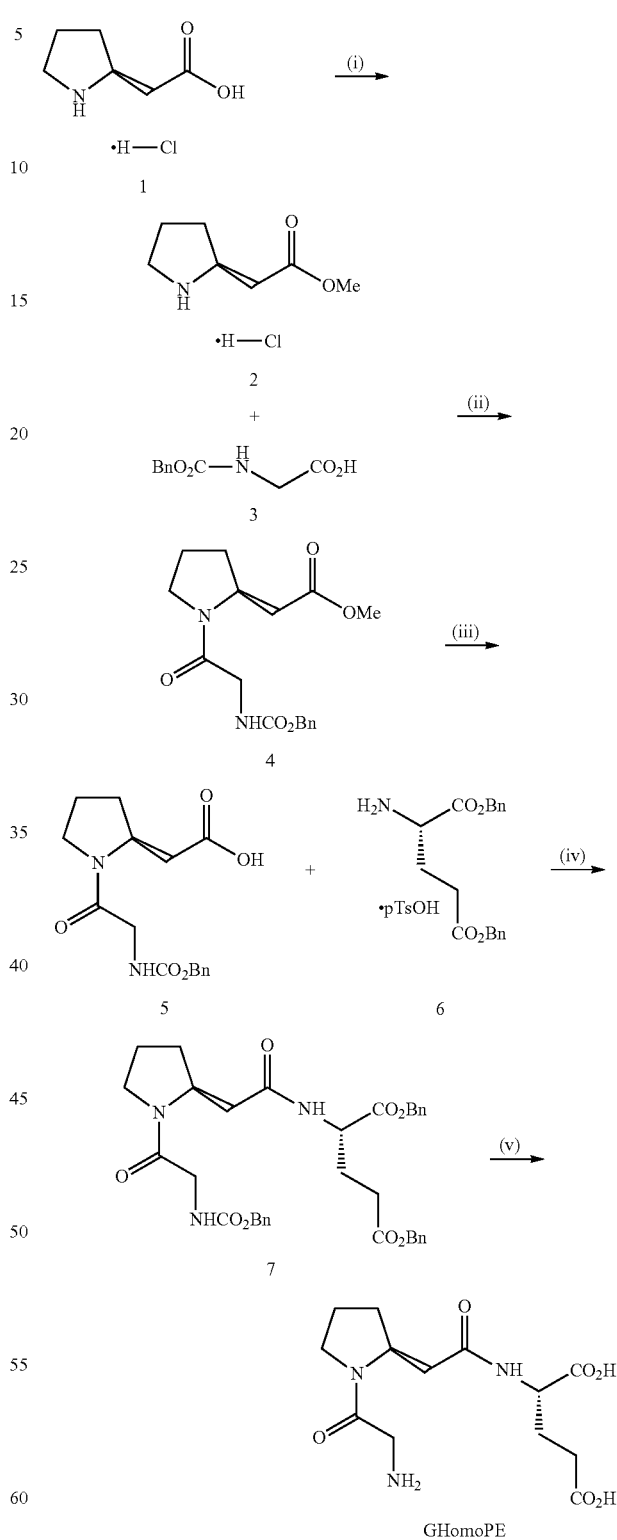

Scheme 1:

Reagents, conditions and yields: (i) thionyl chloride, CH$_3$OH, RT, N$_2$, 24h (97%); (ii) Et$_3$N, BoPCl, CH$_2$Cl$_2$, RT, N$_2$, 19.5h (78%); (iii) Dioxane, 1 M NaOH (aq), RT, 16h (93%); (iv) Et$_3$N, BoPCl, CH$_2$Cl$_2$, RT, N$_2$, 17.5h (74%); (v) H$_2$, 10% Pd/C, 10% H$_2$O/MeOH, RT, 20h (93%).

4.1 Methyl L-pyrrolidin-2-yl acetate hydrochloride 2

An iced cooled solution of hydrochlorid iced cooled solution of hydrochloride 1 (0.25 g, 1.50 mmol) in dry methanol (3 cm$^3$) under an atmosphere of nitrogen was treated dropwise with a solution of thionyl chloride (0.13 cm$^3$, 1.78 mmol). The solution was stirred overnight and the solvent removed under reduced pressure. The resultant light green gum was purified by flash column chromatography (10% methanol/dichloromethane) to afford hydrochloride 2 (0.26 g, 97%) as a light yellow oil, which solidified to a white semi solid on standing: $[\alpha]_D$ +44.3 (c 0.05 in MeOH): $\delta_H$ (300 MHz; CDCl$_3$) 1.73-1.79 (1H, m, Proγ-H$_A$H$_B$), 2.00-2.11 (2H, m, Proγ-H$_A$H$_B$ and Proβ-H$_A$H$_B$), 2.26-2.31 (1H, m, Proβ-H$_A$H$_B$), 2.86 (1 H, dd, J 6.9, 17.2, CH$_A$H$_B$CO$_2$), 3.22 (1 H, dd, J 6.9, 17.2, CH$_A$H$_B$CO$_2$), 3.29 (2 H, t, J 6.8, Proδ-H$_2$), 3.44 (3 H, s, OCH$_3$), 3.92 (1 H, m, Proα-H) and 8.15 (2 H, br s, NCH); 6c (75 MHz; CDCl$_3$) 23.8 (CH$_2$, Proγ-C), 30.8 (CH$_2$, Proβ-C), 36.4 (CH$_2$, CH$_2$CO$_2$), 45.3 (CH$_2$, Proδ-C), 52.6 (CH$_3$, CH$_3$O), 56.3 (CH, Proα-C) and 171.0 (quat., CO); m/z (FAB+) 323.1737 [M$_2$.H$^{35}$Cl.H$^+$](C$_7$H$_{13}$$^{35}$ClNO$_2$)$_2$ H$^{35}$Cl.H requires 323.1738].

4.2 Methyl-N-benzyloxycarbonyl-glycyl-L-pyrrolidin-2-yl acetate 4

Dry triethylamine (0.70 cm$^3$, 5.00 mmol) was added dropwise to a solution of hydrochloride 2 (0.26 g, 1.45 mmol) and N-benzyloxycarbonyl-glycine 3 (0.32 g, 1.53 mmol) in dry dichloromethane (8 cm$^3$) under an atmosphere of nitrogen at 0° C., and the reaction mixture stirred for 10 min. Bis(2-oxo-3-oxazolidinyl)phosphinic chloride (0.39 g, 1.53 mmol) was added and the solution was stirred for 2 h, warmed to room temperature and further stirred for 20 h. Dichloromethane (40 cm$^3$) was added and the solution washed successively with 0.5 M aqueous hydrochloric acid (2×10 cm$^3$) and saturated aqueous sodium hydrogen carbonate (2×10 cm$^3$), dried (MgSO$_4$), filtered and evaporated in vacuo to give a light orange gum. Purification of the resultant residue by flash column chromatography (ethyl acetate) yielded ester 4 (0.38 g, 78%) as a colourless oil. Ester 4 was shown to be an 85:15 trans:cis mixture of conformers by $^1$H NMR analysis (the ratio was estimated from the integration of the signals at δ 4.21-4.30 and 4.37-4.47, assigned to the Proα-H of the minor and major conformers respectively: $[\alpha]_D$ −36.0 (c 0.13 in MeOH); $\delta_H$ (300 MHz; CDCl$_3$) 1.81-2.07 (4 H, m, Proγ-H$_2$ and Proβ-H$_2$), 2.36 (0.85 H, dd, J 9.2 and 15.5, CH$_A$H$_B$CO$_2$), 2.47* (0.15 H, d, J 10.1, CH$_A$H$_B$CO$_2$), 2.60* (0.15 H, d, J 10.1, CH$_A$H$_B$CO$_2$), 2.92 (0.85 H, dd, J 9.2 and 15.5, CH$_A$H$_B$CO$_2$), 3.43-3.44 (2 H, m, Proδ-H$_2$), 3.66 (2.55 H, s, OCH$_3$), 3.70* (0.45 H, s, OCH$_3$), 3.92 (1.7 H, d, J 4.1, Glyα-H$_2$), 3.95* (0.3 H, m, Glyα-H$_2$), 4.21-4.30* (0.15 H, m, Proα-H), 4.37-4.47 (0.85 H, m, Proα-H), 5.11 (2 H, s, OCH$_2$Ph), 5.76 (1H, br s, Gly-NH) and 7.27-7.36 (5 H, m, Ph); $\delta_C$ (75 MHz; CDCl$_3$) 21.4* (CH$_2$, Proγ-C), 23.9 (CH$_2$, Proγ-C), 30.0 (CH$_2$, Proβ-C), 31.5* (CH$_2$, Proβ-C), 37.5 (CH$_2$, CH$_2$CO$_2$), 43.4* (CH$_2$, Proδ-C), 43.8 (CH$_2$, Proδ-C), 46.0 (CH$_2$, Glyα-C), 51.9 (CH$_3$, OCH$_3$), 52.2* (CH$_3$, OCH$_3$), 53.9* (CH, Proα-C), 54.7 (CH, Proα-C) 67.1 (CH$_2$, OCH$_2$Ph), 128.2 (CH, Ph), 128.3 (CH, Ph), 128.7 (CH, Ph), 136.4 (quat., Ph), 156.2 (quat., NCO), 166.6 (quat., Gly-CON) and 171.6 (quat., CO$_2$CH$_3$); m/z (EI+) 334.1532 (M$^+$.C$_{17}$H$_{22}$N$_2$O$_5$ requires 334.1529).

4.3 N-Benzyloxycarbonyl-glycyl-L-pyrrolidin-2-yl acetic acid 5

To a solution of methyl ester 4 (0.36 g, 1.08 mmol) in dioxane (10 cm$^3$) was added dropwise 1 M aqueous NaOH (5 cm$^3$, 5.00 mmol) and the mixture was stirred for 20 h at room temperature. The solution was acidified with 1 M HCl and evaporated in vacuo. The resulting aqueous layer was extracted with dichloromethane (2×25 cm$^3$), dried (Na$_2$SO$_4$), filtered and evaporated in vacuo to form a clear gum, which solidified on standing to acid 5 (0.32 g, 93%) as a clear gum, which was used without further purification. Acid 5 was shown to be an 76:24 trans:cis mixture of conformers by $^1$H NMR analysis (the ratio was estimated from the integration of the broad signals at 6 5.97 and 6.10, assigned to the Gly-NH of the major and minor conformers respectively): $[\alpha]_D$ −33.3 (c 0.03 in MeOH); $\delta_H$ (300 MHz; CDCl$_3$) 1.81-2.04 (4 H, m, Proγ-H$_2$ and Proβ-H$_2$), 2.38 (0.76 H, dd, J 8.9, 15.7, CH$_A$H$_B$CO$_2$), 2.45* (0.24 H, d, J 10.6, CH$_A$H$_B$CO$_2$), 2.58* (0.24 H, d, J 10.6, CH$_A$H$_B$CO$_2$), 2.92 (0.76H, dd, J 3.8 and 15.7, CH$_A$H$_B$CO$_2$), 3.36-3.47 (2 H, m, Proδ-H$_2$), 3.92 (1.52 H, m, Glyα-H$_2$), 3.95* (0.48 H, m, Glyα-H$_2$), 4.21-4.30* (0.76 H, m, Proα-H), 4.37-4.69 (0.24 H, m, Proα-H), 5.11 (2 H, s, OCH$_2$Ph), 5.97 (0.76 H, br s, Gly-NH), 6.10* (0.24 H, br s, Gly-NH), 7.27-7.35 (5 H, m, Ph) and 7.72 (1 H, br s, CO$_2$H); 6c(75 MHz; CDCl$_3$) 21.4* (CH$_2$, Proγ-C), 24.0 (CH$_2$, Proγ-C), 30.4 (CH$_2$, Proβ-C), 31.7* (CH$_2$, Proβ-C), 37.9 (CH$_2$, CH$_2$CO$_2$), 39.1* (CH$_2$, CH$_2$CO$_2$), 43.5* (CH$_2$, Proδ-C), 43.9 (CH$_2$, Proδ-C), 46.4 (CH$_2$, Glyα-C), 53.8* (CH, Proα-C), 54.1 (CH, Proα-C) 67.3 (CH$_2$, OCH$_2$Ph), 128.3 (CH, Ph), 128.4 (CH, Ph), 128.8 (CH, Ph), 136.6 (quat., Ph), 156.8 (quat., NCO), 167.8 (quat., Gly-CON), 175.0* (quat., CO$_2$H) and 175.3 (quat., CO$_2$H); m/z (EI+) 320.1369 (M$^+$.C$_{16}$H$_{20}$N$_2$O$_5$ requires 320.1372).

4.4 Dibenzyl N-benzyloxycarbonyl-glycyl-L-pyrrolidin-2-yl-acetyl-L-glutamate 7

Dry triethylamine (0.38 cm$^3$, 2.73 mmol) was added to a solution of acid 6 (0.29 g, 0.91 mmol) and L-glutamic acid dibenzyl ester p-toluene sulphonate 6 (0.50 g, 1.00 mmol) in dry dichloromethane (50 cm$^3$) under an atmosphere of nitrogen at 0° C., and the reaction mixture stirred for 10 min. Bis(2-oxo-3-oxazolidinyl) phosphinic chloride (BoPCl, 97%) (0.25 g, 1.00 mmol) was added and the solution stirred for 2 h, warmed to room temperature and further stirred for 20 h. The solution was washed successively with 0.5 M aqueous hydrochloric acid (10 cm$^3$) and saturated aqueous sodium hydrogen carbonate (10 cm$^3$), dried (Na$_2$SO$_4$), filtered and evaporated in vacuo to form a light orange gum. Purification of the resultant residue by flash column chromatography (ethyl acetate) yielded fully protected tripeptide 7 (0.42 g, 74%) as a clear oil: $[\alpha]_D$ −26.6 (c 0.13 in MeOH); $\delta_H$ (300 MHz; CDCl$_3$) 1.95-2.47 (9 H, m, Proγ-H$_2$, Proβ-H$_2$, Gluβ-H$_2$, Gluγ-H$_2$ and CH$_A$H$_B$CO$_2$), 2.75 (1 H, dd, J 3.5 and 13.9, CH$_A$H$_B$CO$_2$), 3.35-3.42 (2 H, m, Proδ-H$_2$), 3.94 (2 H, d, J 4.1, Glyα-H$_2$), 4.33-4.34 (1 H, m, Gluα-H), 4.63-4.67 (1 H, m, Proα-H), 5.11-5.26 (6 H, s, 3×OCH$_2$Ph), 5.80 (1 H, br s, Gly-NH), 7.00 (1 H, d, J 7.8, Glu-NH) and 7.31-7.35 (15 H, m, 3×Ph); 6c(75 MHz; CDCl$_3$) 23.8 (CH$_2$, Proγ-C), 27.1 (CH$_2$, Gluβ-C), 30.0 (CH$_2$, Gluγ-C), 30.3 (CH$_2$, Proβ-C), 40.2 (CH$_2$, CH$_2$CO$_2$), 43.5 (CH$_2$, Proδ-C), 45.9 (CH$_2$, Glyα-C), 51.6 (CH, Gluα-C), 55.5 (CH, Proα-C), 66.4 (CH$_2$, OCH$_2$Ph), 66.8 (CH$_2$, OCH$_2$Ph), 67.2 (CH$_2$, OCH$_2$Ph), 127.9 (CH, Ph), 128.0 (CH, Ph), 128.2 (CH, Ph), 128.3 (CH, Ph), 128.4 (CH, Ph), 128.5 (CH, Ph), 135.2 (quat., Ph), 135.7 (quat., Ph), 136.4 (quat., Ph), 156.2 (quat., NCO$_2$), 166.9 (quat., Gly-CON), 170.7 (quat., Pro-CON), 171.5 (quat., Gluα-CO) and 172.4 (quat., Gluγ-CO); m/z (FAB+) 630.2809 (MH$^+$.C$_{35}$H$_{40}$N$_3$O$_8$ requires 630.2815).

4.5 Glycyl-L-Homoproyl-L-glutamic Acid (GHomoPE) 62

A mixture of protected tripeptide 7 (0.39 g, 0.61 mmol) and 10 wt. % palladium on activated carbon (0.007 g, 0.07 mmol) in 10% water/methanol (40 cm$^3$) was stirred under an atmosphere of hydrogen at room temperature for 20 h. The solution was filtered through a Celite™ pad, washed with methanol (2×30 cm$^3$) and the filtrate evaporated to dryness to give a clear gum. The gum was placed under vacuum for 30 min and then triturated with anhydrous diethyl ether to form GHomoPE (0.19 g, 93%) as a white solid. GHomoPE was shown to be an 80:20 trans:cis mixture of conformers by $^1$H NMR analysis (the ratio was estimated from the integration of the signals at, 4.08 and 4.11, assigned to the Gluα-H of the major and minor conformers respectively: mp 48-50° C.; [α]$_D$ –36.6 (c 0.06 in H$_2$O); δ$_H$ (400 MHz; D$_2$O) 1.84-2.22 (6 H, m, Gluβ-H$_2$, Proβ-H$_2$ and Pro-γH$_2$), 2.41-2.62 (3.2 H, m, Gluγ-H$_2$, CH$_A$H$_B$CO$_2$ and 2×*CH$_2$CO$_2$), 2.77 (0.8 H, dd, J 5.4 and 13.9, CH$_A$H$_B$CO$_2$), 3.45-3.55 (1 H, m, Proδ-H$_A$H$_B$), 3.51-3.60 (1 H, m, Proδ-H$_A$H$_B$), 4.08 (1.6 H, q, J 16.9, Glyα-H$_2$), 4.11* (0.4 H, q, J 16.9, Glyα-H$_2$), 4.34 (1 H, dd, J 8.4 and 13.7, Gluα-H) and 4.45-4.47 (1 H, m, Proα-H); δ$_C$ (100 MHz; CDCl$_3$) 21.1* (CH$_2$, Proγ-C), 23.4 (CH$_2$, Proγ-C), 26.0* (CH$_2$, Gluβ-C), 26.7 (CH$_2$, Gluβ-C), 29.5 (CH$_2$, Gluγ-C), 31.0 (CH$_2$, Proβ-C), 31.1* (CH$_2$, Pro-C), 39.1 (CH$_2$, Glyα-C), 39.9* (CH$_2$, Glyα-C), 40.6* (CH$_2$, CH$_2$CO$_2$), 40.9 (CH$_2$, CH$_2$CO$_2$), 46.2* (CH$_2$, Proδ-C), 46.4 (CH$_2$, Proδ-C), 53.8 (CH, Gluα-C), 54.2* (CH, Gluα-C), 55.4* (CH, Proα-C), 55.9 (CH, Proα-C), 165.4 (quat., Gly-CON), 165.5* (quat., Gly-CON), 173.0* (quat., Pro-CON), 173.6 (quat., Pro-CON), 177.2 (quat., Gluα-CO) and 178.1 (quat., Gluγ-CO); m/z (FAB+) 316.1503 (MH$^+$.C$_{13}$H$_{22}$N$_3$O$_6$ requires 316.1509).

Reference: 1. Wanner et al. *Ger. Offen.*, 2000, 36 pp, DE 98-19840611 19980905 (*Chem. Abstr.*, 132:194656 AN 2000:157915).

Example 5

Synthesis of analog 63 (Glycyl-L-3,4-dehydroprolyl-L-glutamic acid trifluoroacetate (G-3,4-dehydro-PE.TFA))

General experimental details were as described in Example 2 above. L-3,4-Dehydroproline 1 was purchased from Fluka. L-Glutamic acid di-tert-butyl ester hydrochloride 4 was purchased from Bachem.

Scheme 1 Reagents, conditions and yields:

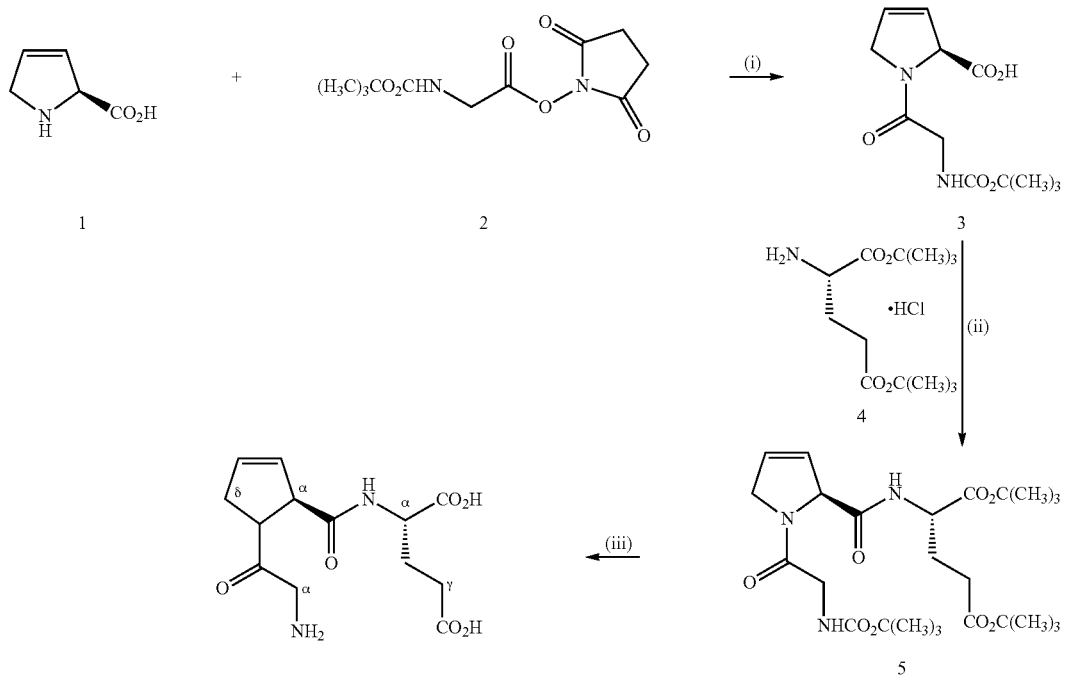

G-3,4-dehydroPE•TFA (i) NaHCO$_3$, dioxane, H$_2$O, RT, overnight (ca. 100%); (ii) BoP, Et$_3$N, CH$_2$Cl$_2$, 0° C. to RT, overnight (59%, over 2 steps); (iii) CF$_3$CO$_2$H, CH$_2$Cl$_2$, RT, 3h (94%).

5.1 Tert-Butyloxycarbonylglycyl-L-3,4-dehydroproline 2

3,4-Dehydroproline 1 (0.011 g, 0.097 mmol) and sodium hydrogen carbonate (0.0082 g, 0.097 mmol) were dissolved in water (1 cm$^3$). A solution of N-tert-butyloxycarbonylglycine N-hydroxysuccinimide 2 (0.024 g, 0.088 mmol) in dioxane (1 cm³) was added dropwise and stirred overnight. The reaction mixture was diluted with water, acidified with solid citric acid and extracted with dichloromethane (3×). The combined organic layers were dried (MgSO₄), filtered and the solvent removed to afford crude acid 3 (0.0242 g, ca. 100%) that was used without further purification. Acid 3 was shown to be a 75:25 trans:cis mixture of conformers by ¹H NMR analysis (the ratio was estimated from the integration of the Proα protons at δ 5.21 and 5.13 of the major and minor conformers respectively): $\delta_H$ (300 MHz; CDCl₃; Me₄Si) 1.411 [2.25H, s, C(CH₃)₃], 1.42 [6.75H, s, C(CH₃)₃], 3.83-4.08 (2H, m, Glyα-H₂), 4.25-4.45 (2H, m, Proδ-H₂), 5.13* (0.25H, br d, J 2.8, Proα-H), 5.21 (0.75H, br d, J 3.1, Proα-H), 5.55-5.80 (2H, br m, O—H and N—H) and 5.86-6.02 (2H, m, Proβ-H and Proγ-H).

5.2 Di-tert-butyl N-tert-butyloxycarbonylglycyl-L-3,4-dehydroprolyl-L-glutamate 5

Triethylamine (0.041 cm³, 0.291 mmol) was added to a solution of acid 3 (0.0242 g, ca. 0.097 mmol), L-glutamic acid di-tert-butyl ester hydrochloride 4 (0.029 g, 0.097 mmol) and benzotriazol-1-yloxytris(dimethylamino)phosphonium hexafluorophosphate (BoP) (0.043 g, 0.097 mmol) in dichloromethane (3 cm³). The solution was stirred overnight washed with 2M aqueous hydrochloric acid, saturated sodium hydrogen carbonate solution, dried (MgSO₄), filtered and the solvent removed to afford an oil (0.0622 g) that was purified by chromatography (SiO₂, hexanes:ethyl acetate, 1:1 then 1:2) to give protected tripeptide 5 (0.0310 g, 59%) as a colourless oil. 5 was shown to be a 79:21 trans:cis mixture of conformers by ¹H NMR analysis (the ratio was estimated from the integration of the Proα protons at δ 5.07 and 5.17-5.18 of the major and minor conformers respectively): $\delta_H$ (300 MHz; CDCl₃; Me₄Si) 1.45-1.48 [27H, m, 3×C(CH₃)₃], 1.90-1.98 (1H, m, Gluβ-$H_AH_B$), 2.06-2.14 (1H, m, Gluβ-$H_AH_B$), 2.24-2.35 (2H, m, Gluγ-H₂), 3.82* (0.21H, br d, J 17.2, Glyα-$H_AH_B$), 3.95 (1H, dd, J 17.1 and 2.0, Glyα-H and *Glyα-$H_AH_B$), 4.04 (0.79H, dd, J 17.2 and 4.4, Glyα-H), 4.30 (0.79H, dd, J 14.0 and 2.0, Proδ-$H_AH_B$), 4.38-4.43 (2H, m, Proδ-H and Gluα-H), 4.54* (0.21H, br d, J 15.2, Proδ-$H_AH_B$), 5.07* (0.21H, br s, Proα-H), 5.17-5.18 (0.79H, m, Proα-H), 5.14* (0.21H, br s, N—H), 5.52 (0.79H, br s, N—H), 5.88-6.03 (2H, m, Proβ-H and Proγ-H) and 7.11 (1H, d, J 7.6, N—H).

5.3 Glycyl-L-3,4-dehydroprolyl-L-glutamic acid trifluoro acetate (G-3,4-dehydroPE) 63

To a solution of protected tripeptide 5 (0.0301 g, 0.0575 mmol) in dichloromethane (3 cm³) was added trifluoroacetic acid (1.5 cm³) and the solution stirred for 3 h at room temperature. The volatiles were removed in vacuo and the residue purified by chromatography (C₁₈, water) and lyophilised to give G-3,4-dehydroPE (0.0224 g, 94%) as a hygroscopic pale yellow solid. G-dehydroPE was shown to be a 84:16 trans:cis mixture of conformers by ¹H NMR analysis (the ratio was estimated from the integration of the Glyα protons at δ 4.07 and 3.78 of the major and minor conformers respectively): no mp due to hygroscopic sample; $[\alpha]_D$ –139.5 (c 0.2 in MeOH); $\delta_H$ (300 MHz; D₂O) 2.02-2.14 (1H, m, Gluβ-$H_AH_B$), 2.25-2.61 (1H, m, Gluβ-$H_AH_B$), 2.53-2.61 (2H, m, Gluγ-H₂), 3.78* (0.16H, d, J 16.2 Glyα-H), 4.03* (0.16H, d, J 16.5 Glyα-H), 4.07 (1.68H, s, Glyα-H₂), 4.38-4.45 (1H, m, Gluα-H), 4.53 (1H, dd, J 9.3 and 5.1, Proδ-H₂), 5.28-5.32 (1H, m, Proα-H), 5.95 (1H, dd, J 6.2 and 2.2, Proβ-H or Proγ-H) and 6.16-6.19 (1H, m, Proβ-H or Proγ-H); $\delta_C$ (75 MHz; D₂O) 25.2* (CH₂, Gluβ-C), 25.7 (CH₂, Gluβ-C), 29.8 (CH₂, Gluγ-C), 30.2* (CH₂, Gluγ-C), 40.0* (CH₂, Glyα-C), 40.2* (CH₂, Glyα-C), 52.1* (CH, Gluα-C), 52.3 (CH, Gluα-C), 53.3 (CH₂, Proδ-C), 54.5* (CH₂, Proδ-C), 67.0* (CH, Proα-C), 67.7 (CH, Proα-C), 124.3 (CH), 128.4* (CH), 128.5 (CH), 165.4 (quat., Gly-CO), 171.7 (quat., Pro-CO), 174.6 (quat., Proα-CO) and 177.0 (quat., Proγ-CO) (CF₃CO₂H not detected); m/z (FAB+) 300.1196 [MH(free base)⁺.C₁₂H₁₈N₃O₆ requires 300.1196].

Example 6

Synthesis of analog 64 (Aminoisobutryl-L-prolyl-L-glutamic acid (AibPE))

General experimental details were as described in Example 2 above.

Scheme 1 Reagents, conditions and yields:

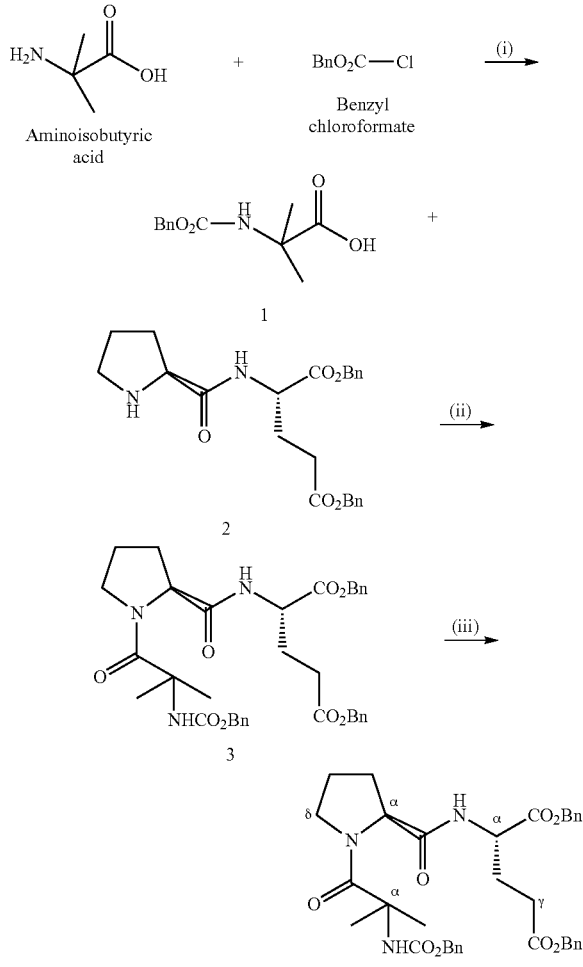

AibPE
(65:35 trans:cis)

(i) Na₂CO₃, dioxane, RT, 20h, (ca. 100%) (ii) HOBt, EDCl, HCl, THF, RT, 20h (26%); (iii) H₂, 10% Pd/C, MeOH, 20h (63%).

6.1 N-Benzyloxycarbonyl aminoisobutyric Acid[1,2] 1

Aminoisobutyric acid (2.00 g, 19.40 mmol) and sodium carbonate (6.16 g, 58.12 mmol) were dissolved in water (70 cm³) and the solution cooled to 0° C. Benzylchloroformate (3.05 cm$^3$, 21.4 mmol) in dioxane (20 cm$^3$) was added dropwise over a period of 15 min. The solution was stirred at 0° C. for 1.5 h and warmed to room temperature. Stirring continued for 20 h and the aqueous layer was extracted with diethylether (100 cm$^3$), acidified with hydrochloric acid (32%) to pH 1 and extracted with ethyl acetate (2×75 cm$^3$). The organic layers were combined, dried (MgSO$_4$), filtered and evaporated under reduced pressure to give a clear oil, which solidified on standing to crude carbamate 1 (4.59 g, 100%) as a gummy solid, which was used without further purification: $\delta_H$ (200 MHz; CDCl$_3$; Me$_4$Si) 1.57 (6H, s, 2×CH$_3$), 5.10 (2H, s, OCH$_2$Ph), 5.55 (1H, br s, NH), 7.26-7.33 (5H, m, Ph) and 10.53 (1H, br s, CO$_2$H); ($\delta_C$ (50 MHz; CDCl$_3$) 25.0 (CH$_3$, 2×CH$_3$), 56.3 [quat., C(CH$_3$)$_2$], 66.9 (CH$_2$, OCH$_2$Ph), 128.0 (CH, Ph), 128.4 (CH, Ph), 136.1 (quat., Ph), 155.2 (quat., NCO$_2$) and 179.6 (quat., CO$_2$H); m/z (EI+) 237 (M$^+$.12%).

6.2 Dibenzyl-N-benzyloxycarbonyl aminoisobutyryl-L-prolyl-L-glutamate 3

Amine$^3$ 2 (DC64.10) (1.00 g, 2.36 mmol), acid 1 (0.56 g, 2.36 mmol) and 1-hydroxybenzotriazole hydrate (0.36 g, 2.26 mmol) were dissolved in tetrahydrofuran (10 cm$^3$) at room temperature. 1-Ethyl-3-(3-dimethylaminopropyl)carbodiimide hydrochloride (0.45 g, 2.36 mmol) was added and the solution stirred for 3 days. The solvent was removed under reduced pressure to dryness and the residue was dissolved in ethyl acetate (100 cm$^3$), washed successively with saturated sodium hydrogen carbonate solution (25 cm$^3$), brine (25 cm$^3$), water (25 cm$^3$) and then dried (MgSO$_4$).The solvent was removed under reduced pressure to give an orange gum. Purification of the gum by flash column chromatography (20% hexane/ethyl acetate) produced fully protected tripeptide 3 (0.40 g, 26%) as a clear gum: $[\alpha]_D$ −36.5 (c 0.05 in MeOH): $\delta_H$ (200 MHz; CDCl$_3$; Me$_4$Si) 1.41 (3H, s, CH$_3$), 1.51 (3H, s, CH$_3$), 1.68-2.29 (6H, m, Proβ-H$_2$, Proγ-H$_2$ and Gluβ-H$_2$), 2.44 (2H, t, J 7.5, Gluβ-H$_2$), 3.20-3.25 (1H, m, Proδ-H), 3.55-3.60 (1H, m, Proδ-H), 4.44-4.51 (1H, m, Gluα-H) 4.54-4.61 (1H, m, Proα-H), 4.97 (2H, s, OCH$_2$Ph), 5.06 (2H, s, OCH$_2$Ph), 5.15 (2H, s, OCH$_2$Ph) 5.48 (1H, br s, NHCO$_2$), 7.28-7.33 (15H, m, Ph) and 7.58-7.62 (1H, m, NHCO); $\delta_C$ (50 MHz; CDCl$_3$) 24.8 [CH$_3$, (CH$_3$)$_2$C], 25.6 (CH$_2$, Proγ-C), 26.1 [CH$_3$, C(CH$_3$)$_2$], 28.0 (CH$_2$, Gluβ-C and Proβ-C), 30.1 (CH$_2$, Gluγ-C), 48.0 (CH$_2$, Proδ-C), 51.8 (CH, Gluα-C), 57.0 (quat, C(CH$_3$)$_2$), 62.2 (CH, Proα-C), 66.1 (CH$_2$, OCH$_2$Ph), 66.9 (CH$_2$, OCH$_2$Ph), 128.0 (CH, Ph), 128.4 (CH, Ph), 128.5 (CH, Ph), 136.0 (quat., Ph), 155.1 (quat., NCO$_2$), 171.0 (quat., Glu-CO), 172.0 (quat., Glu-CO) and 172.7 (quat., Pro-CON); m/z (EI$^+$) 644.2969 (M$^+$.C$_{36}$H$_{42}$N$_3$O$_8$ requires 644.2972).

6.3 Aminoisobutyryl-L-prolyl-L-glutamic acid (AibPE) 64

A mixture of protected tripeptide 3 (0.44 g, 0.68 mmol) and 10 wt % palladium on activated carbon (0.07 g, 0.07 mmol) in methanol (40 cm$^3$) was stirred under an atmosphere of nitrogen and then hydrogen at room temperature for 20 h. The solution was filtered through Celite™ pad and washed with methanol (2×20 cm$^3$). The filtrate was evaporated under reduced pressure to form a clear gum. The gum was dissolved in methanol (20 cm$^3$) and refiltered through Celite™ pad. The solution was evaporated to dryness under reduced pressure to form a light orange gum. The gum was placed on a vacuum line for 15 min and then triturated with anhydrous diethyl ether to form AibPE (0.14 g, 63%) as a light yellow solid. AibPE was shown to be an 65:35 trans:cis mixture of conformers by $^1$H NMR analysis: mp 190-192° C.: $[\alpha]_D$ −35.5 (c 0.06 in MeOH): $\delta_H$ (200 MHz; D$_2$O) 1.47* (1.05H, s, CH$_3$), 1.49* (1.05H, s, CH$_3$), 1.73 (1.95H, s, CH$_3$), 1.76 (1.95H, s, CH$_3$), 1.96-2.34 (6H, m, Proβ-H$_2$, Proγ-H$_2$ and Gluβ-H$_2$), 2.54-2.60 (1.3H, m, Gluβ-H$_2$) 2.60-2.64* (0.7H, m, Gluβ-H$_2$), 3.55-3.59 (1H, m, Proδ-H), 3.70-3.80 (1H, m, Proδ-H), 4.46-4.58 (1H, m, Gluα-H), 4.55-4.57 (1H, m, Proα-H); $\delta_C$ (50 MHz; D$_2$O) 21.3* [CH$_3$, (CH$_3$)C], 21.5 [CH$_3$, (CH$_3$)C], 22.5* (CH$_3$, (CH$_3$)C), 23.8 (CH$_3$, (CH$_3$)C), 24.8 (CH$_2$, Proγ-C), 25.0 (CH$_2$, Gluβ-C), 25.5* (CH$_2$, Proγ-C), 27.9 (CH$_2$, Proβ-C), 29.3* (CH$_2$, Proβ-C), 29.6 (CH$_2$, Gluγ-C), 45.5* (CH$_2$, Proδ-C), 48.5 (CH$_2$, Proδ-C), 51.9 (CH, Gluα-C), 52.7* (CH, Gluα-C), 57.0* [quat., C(CH$_3$)$_2$], 57.9 [quat., C(CH$_3$)$_2$], 58.5* (CH, Proα-C), 62.1 (CH, Proα-C), 171.0 (quat., Aib-CO), 174.0 (quat., Pro-CON), 174.8 (quat., Gluα-CO$_2$) and 176.8 (quat, Gluγ-CO$_2$); m/z (FAB+) 330.1664 (MH$^+$.C$_{14}$H$_{24}$N$_3$O$_6$ requires 330.1665)

References: 1. Wipf et al. Helv. Chim. Acta, 1988, 71, 140; 2. Kent et al. J Sol. Chem., 1985, 14, 101; 3. Gillesse et al. Helv. Chim. Acta, 1970, 53, 63.

Example 7

Synthesis of Analog 65
(Glycyl-L-Prolyl-L-Norvaline (GP Norvaline))

General experimental details were as described in Example 2 above. L-Norvaline 1 was purchased from Sigma.

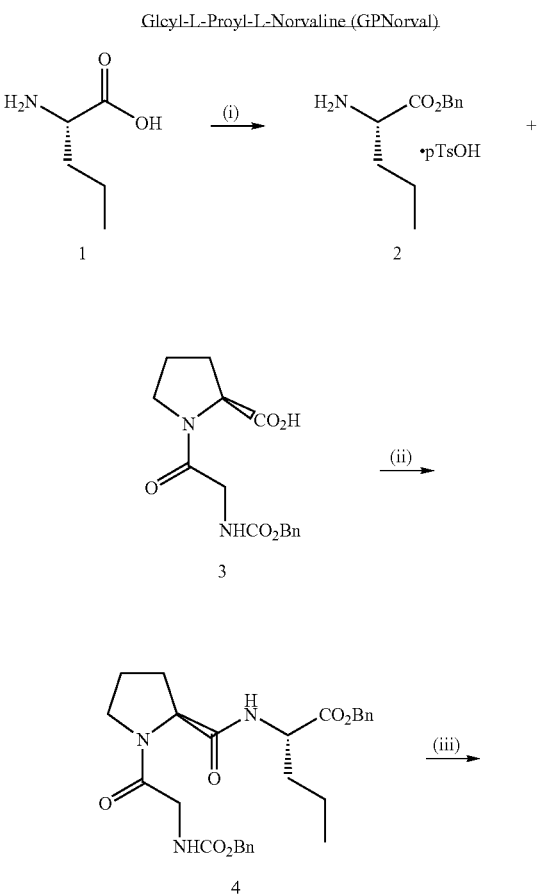

Glcyl-L-Proyl-L-Norvaline (GPNorval)

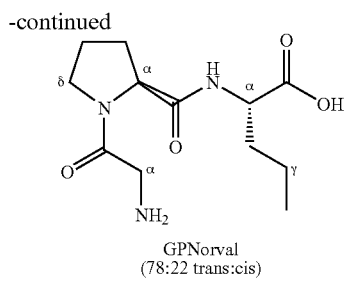

GPNorval
(78:22 trans:cis)

Scheme 1 reagents, conditions and yields: (i) BnOH, pTsOH·H₂O, benzene, reflux, 17h (95%) (ii) ethyl chloroformate, Et₃N, CH₂Cl₂, 0° C. to RT, overnight (78%); (iii) H₂, 10% Pd/C, MeOH:H₂O (2:1), 18h (84%).

7.1 L-Norvaline benzyl ester p-toluenesulphonate 2

A suspension of L-norvaline 1 (1.0 g, 8.53 mmol) benzyl alcohol (5 cm³) and p-toluenesulphonic acid (1.70 g, 8.96 mmol) was heated under reflux in benzene (25 cm³) with the removal of water (Dean-Stark trap) for 17 h (a solution resulted after 5 min). The solution was then cooled to room temperature and dry ether was added. Upon cooling to 0° C. a white solid precipitated and was collected by filtration, washed with dry ether and dried to give p-toluenesulphonate 2 (3.07 g, 95%) as a white solid: mp 142-144° C.; $[\alpha]_D$ −1.45 (c 1 in dichloromethane); $\delta_H$ (200 MHz; CDCl₃; Me₄Si) 0.7 (3H, t, J 7.1, 5-H₃), 1.09-1.37, (2H, m, 4-H₂), 1.74, (2H, app. quartet, J 7.9, 3-H₂), 2.30 (3H, s, Ar—CH₃), 3.99 (1H, t, J 6.2, 2-H₂), 4.98 (1H, d, J 12.3, OCH$_A$H$_B$Ph), 5.11 (1H, d, J 12.3, OCH$_A$H$_B$Ph), 7.07 (2H, d, J 8.0, 3'-H); 7.22-7.30 (5H, m, Ph-H) and 7.74 (2H, d, J 8.0, 2'-H); $\delta_C$ (50 MHz; CDCl₃) 13.4 (CH₃, 5-C), 17.9 (CH₂, 4-C), 21.2 (CH₃, Ar—CH₃) 32.3 (CH₂, 3-C), 53.1 (CH, 2-C), 67.6 (CH₂, OCH₂Ph), 126.0 (CH, Ph), 128.2 (CH, Ph), 128.3 (CH, Ph), 128.4 (CH, Ph), 128.7 (CH, Ph), 134.8 (quat., Ph), 140.2 (quat., Ph), 141.4 (quat., Ph) and 169.4, (quat., 1-C); m/z (FAB) 587.2777 [M₂.pTsOH.H⁺: (C₁₂H₁₇NO₂)₂.C₇H₈O₃S.H requires 587.2791].

7.2 N-Benzyloxycarbonyl-glycyl-L-prolyl-L-norvaline benzyl ester 4

To a stirred solution of benzyl N-benzyloxycarbonyl-glycyl-L-proline 3 (0.4 g, 1.3 mmol) under nitrogen in dry dichloromethane (20 cm³) was added diisopropylethylamine (0.31 cm³, 1.76 mmol). The suspension was stirred for 5 min (a solution was obtained), cooled to 0° C. and ethyl chloroformate (0.166 cm³, 1.73 mol) was added. After 45 min a solution of diisopropylethylamine (0.31 cm³, 1.76 mmol) and p-toluenesulphonate 2 (0.644 g, 1.70 mmol) in dry dichloromethane (20 cm³) was added dropwise over 5 min. The cooling bath was removed and the resultant solution was stirred overnight. The solvent was removed in vacuo and the residue was chromatographed (silica gel, 50-100% ethyl acetate-hexane) to give fully protected tripeptide 4 (0.502 g, 78%) as a colourless oil. Tripeptide 4 was shown to be a 84:16 trans.-cis mixture of conformers by ¹³C NMR analysis (the ratio was estimated from the integration of the ᵗEβ-C carbons at δ 34.0 and 33.6 and the Eγ-C carbons at δ 18.5 and 18.8 of the major and minor conformers respectively): $[\alpha]_D$ −70.3 (c 0.8 in dichloromethane); $\delta_H$ (300 MHz; CDCl₃; Me₄Si) 0.87 (3H, d, J 6.0, Eγ-CH₃), 1.26-1.33 (2H, m, Eγ-H₂), 1.58-1.68 (1H, m, Eβ-H$_A$H$_B$), 1.70-2.26 (5H, m, Eβ-H$_A$H$_B$, Proβ-H₂, and Proγ-H₂), 3.38 (0.84H, d, J 7.6, Proδ-H$_A$H$_B$), 3.51-3.56 (0.84H, m, Proδ-H$_A$H$_B$), 3.60-3.65* (0.32H, m, Proδ-H₂), 3.76* (0.16H, d, J 16.5, Glyα-H$_A$H$_B$), 3.91 (1.84H, m, Glyα-H₂), 4.37* (0.16H, br s, Proα-H), 4.49-4.62 (2H, m, Proα-H, Eα-H), 5.09-5.21 (4H, m, 2×OCH₂Ph), 5.85 (1H, br s, Gly-NH), 7.2 (1H, d, J 5.5, Eα-NH) and 7.34 (10H, s, 2×Ph); $\delta_C$ (75 MHz; CDCl₃) 13.4 (CH₃, Eγ-CH₃), 13.5* (CH₃, Eγ-CH₃), 18.5 (CH₂, Eγ-C), 18.8* (CH₂, Eγ-C), 22.2* (CH₂, Proγ-C), 24.7 (CH₂, Proγ-C), 27.7, (CH₂, Proβ-C) 31.9* (CH₂, Proβ-C) 33.6* (CH₂, Eβ-C), 34.0 (CH₂, Eβ-C), 43.3 (CH₂, Glyα-C), 46.2 (CH, Proδ-C), 47.0* (CH, Proδ-C), 52.1* (CH, Eα-C), 52.3 (CH, Eα-C), 59.9 (CH, Proα-C), 66.8 (CH₂, OCH₂Ph), 67.1* (CH₂, OCH₂Ph), 127.9 (CH, Ph), 127.99 (CH, Ph), 128.0 (CH, Ph), 128.1* (CH, Ph), 128.2 (CH, Ph), 128.4 (CH, Ph), 128.5 (CH, Ph), 135.4 (quat., Ph), 136.3 (quat., Ph), 156.2 (quat., NCO₂), 156.4* (quat., NCO₂), 167.9 (quat., Gly-CO), 168.2* (quat., Gly-CO), 170.7 (quat., Pro-CON), 171.1* (quat., Pro-CON) and 172.1 (quat., Eα-CO); m/z (FAB+) 495.2381 (MH⁺.C₂₇H₃₃N₃O₆ requires 495.2370).

ᵗE refers to the proline analog portion in question
* Denotes resonances assigned to minor conformer.

7.3 Glycyl-L-prolyl-L-norvaline (GPNorval) 65

Tripeptide 4 (0.308 g, 0.62 mmol) was dissolved in methanol (30 cm³). The reaction flask was flushed with nitrogen and 10 wt. % palladium on activated carbon (66 mg, 0.062 mmol) was added and the mixture was hydrogenated at 1 atmosphere of hydrogen. After 30 min a white solid precipitated. Water (15 cm³) was added to dissolve the solid and the reaction was stirred for 18 h. The reaction was filtered through Celite™ washed with methanol/water and the solvent removed to yield an oil which was contaminated with palladium. The filtration was repeated again and the solvent removed to yield a white sold which was suspended in methanol and placed in a freezer overnight. The solid was filtered, washed with ice-cold methanol and dried to yield GPNorval (0.142 g, 84%) as white flakes. GPNorval was shown to be a 78:22 trans:cis mixture of conformers by ¹³C NMR analysis (the ratio was estimated from the integration of the Proβ-C carbons at δ 29.4 and 31.6 and the Proγ-C carbons at δ 24.1 and 21.9 of the major and minor conformers respectively): $[\alpha]_D$ −79 (c 0.1 in water); $\delta_H$ (300 MHz; D₂O) 0.85 (3H, d, J 7.4, Eγ-CH₃), 1.29 (2H, sextet, J 7.0, Eγ-H₂), 1.53-1.75 (2H, m, Eβ-H₂) 1.88-2.05 (3H, m, Proβ-H$_A$H$_B$, Proγ-H₂) 2.09-2.27 (1H, m, Proβ-H$_A$H$_B$), 3.51-3.82 (4H, m, Proδ-H₂, Glyα-H₂), 4.09 (0.78H, dd, J 7.8 5.0, Eα-H), 4.14* (0.22H, dd, J 9 5.0, Eα-H) and 4.41 (1H, m, Proα-H); $\delta_C$ (75 MHz; D₂O) 12.8* (CH₃, Eγ-CH₃), 12.9 (CH₃, Eγ-CH₃), 18.5 (CH₂, Eγ-C), 18.7* (CH₂, Eγ-C), 21.9* (CH₂, Proγ-C), 24.1 (CH₂, Proγ-C), 29.4, (CH₂, Proβ-C), 31.6* (CH₂, Proβ-C), 33.3* (CH₂, Eβ-C), 33.8 (CH₂, Eβ-C), 40.6 (CH₂, Glyα-C), 46.8 (CH, Proδ-C), 47.5* (CH, Proδ-C), 55.1 (CH, Eα-C), 60.0* (CH, Proα-C), 60.4 (CH, Proα-C), 166.6 (quat., Gly-CO), 173.1 (quat., Pro-CON), 178.9* (quat., Eα-CO) and 179.0 (quat., Eα-CO); m/z (FAB+) 272.1641 (MH⁺.C₁₂H₂₂N₃O₄ requires 272.1610).

Example 8

Synthesis of analog 66
(Glycyl-D,L-pipecolinyl-L-glutamic Acid (G(D,L)PipE))

General experimental details were as described in Example 1 above. N-Benzyloxycarbonyl-glycine 1, N-hydroxysuccinimide 2 (97%) (NHS), D,L-pipecolinic acid 4 (98%) and 10% palladium on activated carbon were purchased from Aldrich Chemical Company. N,N'-Dicyclohexylcarbodiimide (DCC) was purchased from Riedel-de-Haen. L-glutamic acid dibenzyl ester p-toluenesulphonate 6 was purchased from Bachem. Bis(2-oxo-3-oxazolidinyl)phosphinic chloride (97%) (BoPCl) was purchased from Fluka.

Scheme 1 Reagents, conditions and yields:

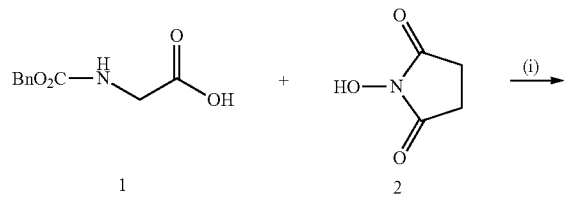

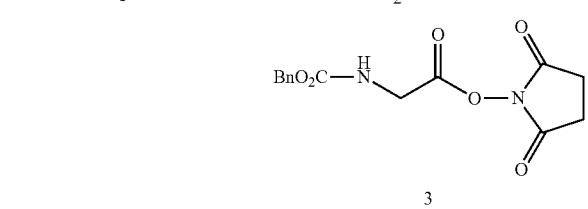

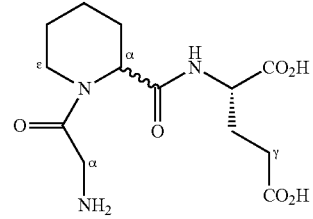

G(D,L)PipE (i) DCC, DME, 0° C. to -5° C., 20h (95%); (ii) Et₃N, DMF, 80° C., 4h to RT, 2d (67%); (iii) BOPCl, Et₃N, CH₂Cl₂, 0° C. to RT, 20h (74%); (iv) H₂, 10% Pd/C, MeOH, RT, 20h (95%).

8.1 N-Benzyloxycarbonyl-glycyl succinimide 1,2 3

N-Benzyloxycarbonyl-glycine 1 (7.50 g, 35.9 mmol) and N-hydroxysuccinimide 2 (4.13 g, 35.9 mmol) were dissolved in 1,2-dimethoxyethane (60 cm$^3$) and cooled to 0° C. (ice/water) under nitrogen. N,N'-Dicyclohexylcarbodiimide (8.14 g, 39.5 mmol) was added and the solution stirred for 1.5 h and then placed in a refrigerator at −5° C. for 20 h. The solution was filtered and evaporated under reduced pressure to form a yellow oil. The oil was triturated with diethyl ether (30 cm$^3$) to form succinimde 3 as a white solid. This solid was used subsequently without further purification.

8.2 N-Benzyloxycarbonyl-glycyl-D,L-pipecolinic acid [3] 5

D,L-Pipecolinic acid 4 (0.20 g, 1.55 mmol) and N-benzyloxycarbonyl-glycyl N-hydroxysuccinimide 3 (0.47 g, 1.5 mmol) were added to dimethylformamide (2 cm$^3$) at room temperature under nitrogen. Triethylamine (0.22 cm$^3$, 1.58 mmol) was then added dropwise over a period of 5 min. The solution was heated at 80° C. for 4 h and then cooled to room temperature and stirred for 2 days. Ethyl acetate (40 cm$^3$) was added and the resulting solution washed with 1M hydrochloric acid (2×5 cm$^3$), dried (MgSO₄), filtered and evaporated under reduced pressure to yield a clear gum, which was triturated with diethyl ether (5 cm$^3$) to produce acid 5 (0.33 g, 67%) as a white solid. Acid 5 was shown to be an 75:25 trans:cis mixture of conformers by $^1$H NMR analysis (the ratio was estimated from the integration of the doublets at 6 3.76 and 3.81, assigned to the Glyα-H$_A$H$_B$ of the minor and major conformers respectively): $\delta_H$ (300 MHz; CD₃OD) 1.05-1.76 (5H, m, pipβ-H, pipγ-H₂ and pipδ-H₂), 2.19 (0.75H, t, J 12.6, pipβ-H), 2.62* (0.25H, t, J 15.4, pipβ-H), 3.14-3.25 (1H, m, pipε-H$_A$H$_B$), 3.65-3.70 (1H, pipε-H$_A$H$_B$), 3.76* (0.25H, d, J 16.7, Glyα-H$_A$H$_B$), 3.81 (0.75H, d, J 16.9, Glyα-H$_A$H$_{B'}$,), 4.06* (0.25H, d, J 16.6, Glyα-H$_A$H$_{B'}$,), 4.08 (0.75H, d, J 17.0, Glyα-H$_A$H$_{B'}$,), 4.22* (0.25H, d, J 13.6, pipε-H), 4.60* (0.25H, br s, pipα-H), 4.83 (2H, s, OCH₂Ph), 5.14 (0.75H, br s, pipα-H) and 7.20-7.31 (5H, m, Ph); $\delta_C$ (75 MHz, CD₃OD) 22.5 (CH₂, pipγ-C), 26.2* (CH₂, pipγ-C), 26.6 (CH₂, pipβ-C), 27.3* (CH₂, pipβ-C), 28.2 (CH₂, pipδ-C), 28.5 (CH₂, pipδ-C), 35.3 (CH₂, pipε-C), 41.8* (CH₂, Glyα-C), 44.2 (CH₂, Glyα-C), 54.3 (CH, pipα-C), 57.1* (CH, pipα-C), 68.3 (CH₂, OCH₂Ph), 129.5 (CH, Ph), 129.6 (CH, Ph), 130.1 (CH, Ph), 138.8 (quat., Ph), 159.5 (quat., NCO₂), 171.5 (quat., Gly-CO), 174.1* (quat., CO₂H) and 174.7 (quat., CO₂H); m/z (EI+) 320.1369 (M⁺.C₁₆H₂₀N₂O₅ requires 320.1372).

8.3 Benzyl-N-benzyloxycarbonylglycyl-D,L-pipecolinyl-L-glutamate 7

Acid 5 (0.25 g, 0.78 mmol), L-glutamic acid dibenzyl ester p-toluenesulphonate 6 (0.47 g, 0.94 mmol) and bis(2-oxo-3-oxazolidinyl)phosphinic chloride (97%) (0.24 g, 0.94 mmol) were dissolved in dichloromethane (10 cm$^3$) under nitrogen and cooled to 0° C. Triethylamine (0.25 cm$^3$, 1.80 mmol) was added dropwise over a period of 5 min. The solution was stirred for 1.5 h then allowed to warm to room temperature and stirred overnight. Dichloromethane (30 cm$^3$) was added and the organic layer washed successively with saturated sodium hydrogen carbonate solution (10 cm$^3$) and aqueous 2M citric acid (10 cm$^3$), then dried (MgSO$_4$), filtered and evaporated under reduced pressure to form a white gummy solid, which was purified by flash column chromatography (ethyl acetate) to produce fully protected tripeptide 7 (0.37 g, 74%) as a clear gum. Tripeptide 7 was shown to be an 87:13 trans:cis mixture of conformers of the two equimolar diasteoisomers by $^1$H NMR analysis (the ratio was estimated from the integration of the signals at δ 4.05-4.11 and 4.20-4.30, assigned to the Glyα-H$_2$ protons of the major and minor conformers respectively): $[α]_D$ −9.2 (c 0.07 in MeOH); $δ_H$ (300 MHz; CDCl$_3$; Me$_4$Si) 1.11-2.22 (8H, m, pipβ-H$_2$, pipγ-H$_2$ pipδ-H$_2$ and Gluβ-H$_2$), 2.30-2.41 (2H, m, Gluγ-H$_2$), 3.00-3.20 (1 H, m, pipε-H), 3.48 (1 H, t, J 10.6, pipε-H), 4.05-4.11 (1.74 H, m, Glyα-H$_2$), 4.20-4.30* (0.26 H, m, Glyα-H$_2$), 4.55-4.59 (1 H, m, Gluα-H), 5.07-5.23 (7H, m, 3×OCH$_2$Ph and pipα-H), 5.84 (1 H, br s, Gly-NH), 6.97* (0.13 H, d, J 7.2, Glu-NH), 7.19 (0.87 H, d, J 7.2, Glu-NH) and 7.31-7.32 (15H, m, 3×Ph); $δ_C$ (75 MHz, CDCl$_3$) 20.1 (CH$_2$, pipγ-C), 20.4 (CH$_2$, pipγ-C), 25.3 (CH$_2$, Gluβ-C), 25.4 (CH$_2$, Gluβ-C), 25.7 (CH$_2$, pipβ-C), 25.9 (CH$_2$, pipβ-C), 26.1 (CH$_2$, pipδ-C), 26.7 (CH$_2$, pipδ-C), 30.8 (CH$_2$, Gluγ-C), 30.9 (CH$_2$, Gluγ-C), 34.2 (CH$_2$, pipε-C), 40.6* (CH$_2$, Glyα-C), 43.0 (CH$_2$, Glyα-C), 43.2 (CH$_2$, Glyα-C), 49.4* (CH, pipα-C), 52.5 (CH, pipα-C), 52.6 (CH, pipα-C), 52.7 (CH, Gluα-C), 53.0 (CH, Gluα-C), 67.0 (CH$_2$, OCH$_2$Ph), 67.1 (CH$_2$, OCH$_2$Ph), 67.2 (CH$_2$, OCH$_2$Ph), 67.6 (CH$_2$, OCH$_2$Ph), 67.7 (CH$_2$, OCH$_2$Ph), 69.4 (CH$_2$, OCH$_2$Ph), 127.9 (CH, Ph), 128.0 (CH, Ph), 128.2 (CH, Ph), 128.4 (CH, Ph), 128.5 (CH, Ph), 135.1 (quat., Ph), 135.5 (quat., Ph), 136.4 (quat., Ph), 156.2 (quat., NCO$_2$), 168.3 (quat., Gly-CO), 168.4 (quat., Gly-CO), 170.3 (quat., Glu-CO), 170.5 (quat., Glu-CO), 171.1 (quat., Glu-CO), 171.3 (quat., Glu-CO), 173.0 (quat., pip-CONH) and 173.4 (quat., pip-CONH); m/z (FAB+) 630.2821 (M$^+$.C$_{35}$R$_{40}$N$_3$O$_8$ requires 630.2815).

8.4 Glycyl-D,L-pipecolinyl-L-glutamic acid [G(D,L)PipE] 66

A mixture of protected tripeptide 7 (0.72 g, 1.14 mmol) and 10% palladium on activated carbon (0.12 g, 0.11 mmol) in methanol (70 cm$^3$) was stirred under an atmosphere of hydrogen at room temperature for 20 h. The solution was filtered through a Celite™ pad, washed with methanol (60 cm$^3$) and the filtrate evaporated to dryness to form a clear gum. This gum was dissolved in methanol (30 cm$^3$) and refiltered through a Celite™ pad. The solution was evaporated to dryness to form a clear gum. The gum was placed on a vacuum line for 15 min and then triturated with anhydrous diethyl ether to form G(D,L)PipE (0.34 g, 95%) as a white solid. G(D,L)PipE was shown to be an 80:20 trans:cis mixture of conformers of the two equimolar diastereomers by $^1$H NMR analysis (the ratio was estimated from the integration of the triplets at δ 2.91 and 3.34, assigned to the pipε-H$_A$H$_B$ of the minor and major conformers respectively): mp 67-69° C.; $[α]_D$ +7.9 (c 0.09 in MeOH); $δ_H$ (400 MHz; CD$_3$OD) 1.37-1.65 (4H, Gluβ-H$_2$ and pipγ-H$_2$), 1.89-2.52 (6H, pipδ-H$_2$, pipβ-H$_2$ and Gluγ-H$_2$), 2.78* (0.1H, t, J 10.5, pipε-H$_A$H$_B$), 2.91* (0.1H, t, J 10.5, pipε-H$_A$H$_B$), 3.18 (0.4H, t, J 10.5, pipε-H$_A$H$_B$), 3.34 (0.4H, t, J 10.5, pipε-H$_A$H$_B$), 3.52-3.58 (1H, m, pipε-H$_A$H$_B$), 3.81-3.88 (1.6H, m, Glyα-H$_2$), 4.00-4.10* (0.2H, m, Glyα-H$_2$), 4.16 (0.8H, t, J 6.4, Gluα-H), 4.40-4.50* (0.2H, m, Glyα-H$_2$), 4.46-4.50* (0.2H, m, pipα-H) and 5.05-5.09 (0.8H, m, pipα-H); $δ_C$ (75 MHz, CD$_3$OD) 21.8 (CH$_2$, pipγ-C), 25.7 (CH$_2$, Gluβ-C), 26.0* (CH$_2$, Gluβ-C), 26.5 (CH$_2$, Gluβ-C), 27.0 (CH$_2$, pipβ-C), 27.4* (CH$_2$, pipβ-C), 27.6 (CH$_2$, pipβ-C), 28.1 (CH$_2$, pipδ-C), 28.3* (CH$_2$, pipδ-C), 28.7 (CH$_2$, pipδ-C), 32.2 (CH$_2$, Gluγ-C), 33.1 (CH$_2$, Gluγ-C), 33.2* (CH$_2$, Gluγ-C), 33.5* (CH$_2$, Gluγ-C), 41.9 (CH$_2$, pipε-C), 44.1 (CH$_2$, Glyα-C), 44.6* (CH$_2$, Glyα-C), 44.8* (CH$_2$, Glyα-C), 45.6 (CH$_2$, Glyα-C), 55.0 (CH, pipα-C), 56.1 (CH, pipα-C), 56.2 (CH, Gluα-C), 57.7* (CH, Gluα-C), 57.9* (CH, Gluα-C), 60.5 (CH, Gluα-C), 168.3 (quat., Gly-CO), 169.8 (quat., Gly-CO), 172.5 (quat., pip-CON), 174.6 (quat., pip-CON), 177.2 (quat., Gluα-CO), 178.5 (quat., Gluα-CO), 179.3 (quat., Gluγ-CO) and 180.0 (quat., Gluγ-CO); m/z (FAB+) 316.1509 (MH$^+$.C$_{13}$H$_{22}$N$_3$O$_6$ requires 316.1509).

References: 1. Detsi et al. *J. Chem. Soc. Perkin Trans* 1, 1998, 15, 2443; 2. Scudder et al. *Tet. Lett.* 1995, 36, 2105; 3. Nishitani et al. *J. Org. Chem.*, 1982, 47, 1706.

Example 9

Synthesis of analog 67 (Pyrrolidinoglycyl-L-2-Methyl-proline-L-Glutamic Acid (PyrrolidinoG-2MePE))

General experimental details were as described in Example 2 above. Hydrochloride (1) and Pyrrolidinoacetic acid (2) synthesised as described in the synthesis of DC54 (Cyclic G-2EtP) and DC68 (Pyrrolidino GPE), respectively. Glutamic acid dibenzyl ester p-toluenesulphonate (5) and bis(2-oxo-3-oxazolidinyl)phosphinic chloride (BoPCl, 97%) were purchased from Bachem and Fluka respectively.

Scheme 1 Reagents, conditions and yields:

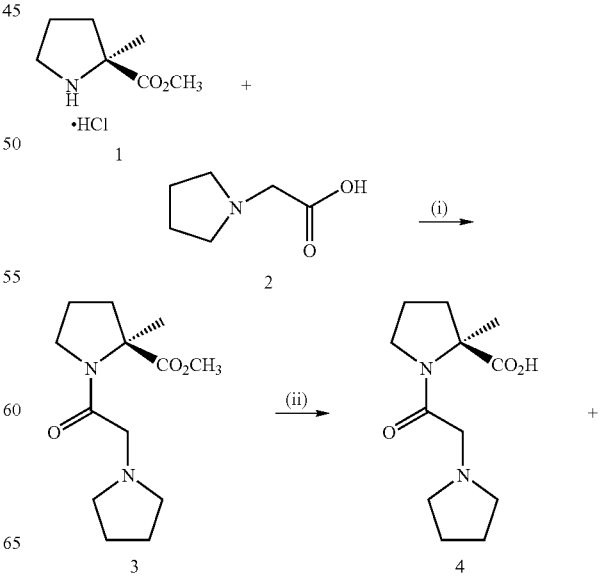

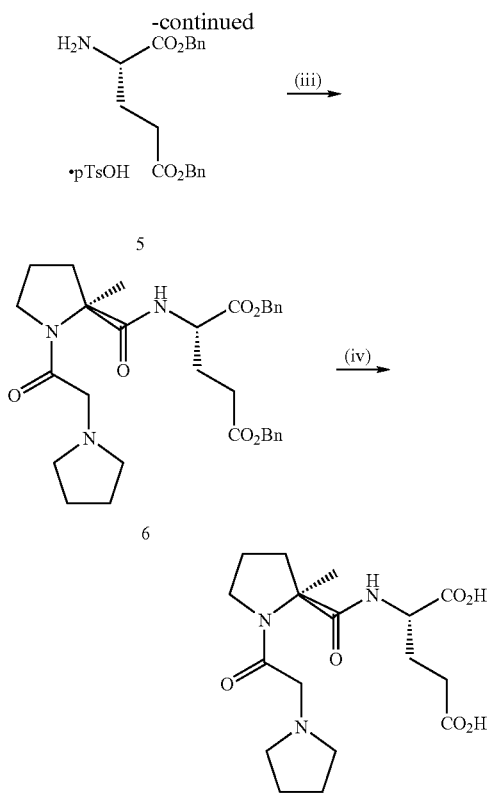

Pyrrolidino G-2MePE (i) Et₃N, BoPCl, DMF, N₂, 100° C. to RT, 3d (19%); (ii) Dioxane, 1M aq. NaOH, RT, 2d (66%); (iii) Et₃N, BoPCl, CH₂Cl₂, N₂, RT, 3d (40%); (iii) 10% Pd/C, H₂, 9:1 EtOH-H₂O, H₂, 20h (98%).

9.1 Methyl pyrrolidinoglycyl-L-2-methylprolinate (3)

Dry triethylamine (1.9 cm³, 13.7 mmol) was added dropwise to a solution of acid 2 (0.39 g, 3.32 mmol) and hydrochloride 1 (0.40 g, 2.21 mmol) in dry dimethylformamide (10 cm³) under an atmosphere of nitrogen at room temperature, and the reaction mixture stirred for 1 h. Bis(2-oxo-3-oxazolidinyl)phosphinic chloride (BOPCl, 97%) (0.70 g, 2.75 mmol) was added and the solution was stirred for 2 h at room temperature then heated to 100° C. for 3 h, cooled to room temperature and stirred for 3 days. The solution was evaporated to dryness in vacuo to form a dark brown solid which was redissolved in ethyl acetate (50 cm³) and then washed with sat. sodium hydrogen carbonate (20 cm³). The aqueous layer was reextracted with ethyl acetate (2×20 cm³). The combined organic layers was dried (Na₂SO₄) and evaporated under reduced pressure. Purification of the resultant residue by flash column chromatography (5% methanol-dichloromethane) amide 3 (0.11 g, 19%) as an orange oil: $\delta_H$ (400 MHz, CDCl₃) 1.56 (3H, s, Proα-CH₃), 1.77-1.80 (4H, m, 2×Pyrβ-H₂), 1.85-1.90 (1H, m, Proγ-$H_AH_B$), 2.00-2.04 (2H, m, Proβ-H₂), 2.10-2.13 (1H, m, Proγ-$H_AH_B$), 2.58-2.63 (4H, m, 2×Pyrα-H₂), 3.25 (2H, s, Glyα-H₂) and 3.66-3.73 (5H, m, Proδ-H₂ and OCH₃); $\delta_C$ (100 MHz, CDCl₃) 21.8 (CH₃, Proα-CH₃), 24.0 (CH₂, 2×Pyrβ-C), 24.5 (CH₂, Proγ-C), 38.6 (CH₂, Proβ-C), 47.9 (CH₂, Proδ-C), 52.6 (CH₃, OCH₃), 54.4 (CH₂, 2×Pyrα-C), 59.3 (CH₂, Glyα-C), 66.2 (quat., Proα-C), 168.6 (quat., Gly-CO) and 174.8 (quat., CO₂CH₃).

9.2 Pyrrolidinoglycyl-L-2-methylproline (4)

To a solution of amide 3 (0.08 g, 0.31 mmol) in dioxane (5 cm³) was added dropwise 1 M aqueous NaOH (2.5 cm³, 2.5 mmol) and the mixture stirred for 2 days at room temperature. The reaction mixture was acidified with 1 M hydrochloride acid and evaporated to dryness under reduced pressure. The resulting suspension was redissolved in ethanol, filtered and evaporated to dryness in vacuo to afford the acid 4 (0.05 g, 66%) as a dark brown gum: $\delta_H$ (400 MHz, CD₃OD) 1.56 (3H, s, Proα-CH₃), 1.94-2.22 (8H, m, Proβ-H₂, Proγ-H₂ and 2×Pyrβ-H₂), 3.10-3.13 (2H, m, Pyrα-H₂), 3.54-3.63 (2H, m, Proδ-H₂), 3.67-3.70 (2H, m, Pyrα-H₂), and 4.27 (2H, s, Glyα-H₂); $\delta_C$ (100 MHz, CD₃OD) 22.1 (CH₃, Proα-CH₃), 24.6 (CH₂, Pyrβ-C), 24.7 (CH₂, Pyrβ-C), 25.3 (CH₂, Proβ-C), 40.3 (CH₂, Proγ-C), 49.1 (CH₂, Proδ-C), 56.6 (CH₂, Pyrα-C), 56.8 (CH₂, Pyrα-C), 57.9 (CH₂, Glyα-C), 68.5 (quat., Proα-C), 164.7 (quat., Gly-CO) and 177.2 (quat., CO₂H).

9.3 Dibenzyl pyrrolidinoglycyl-L-2-methyl-prolyl-L-glutamate (6)

Dry triethylamine (0.09 cm³, 0.62 mmol) was added dropwise to a solution of acid 4 (0.05 g, 0.15 mmol) and L-glutamic acid dibenzyl ester p-toluenesulphonate 5 (0.11 g, 0.22 mmol) in dry dichloromethane (8 cm³) under an atmosphere of nitrogen at room temperature, and the reaction mixture stirred for 10 min. Bis(2-oxo-3-oxazolidinyl)phosphinic chloride (BoPCl, 97%) (0.06 g, 0.22 mmol) was added and the solution was stirred for 3 days. The solution was washed successively with 10% aqueous hydrochloric acid (7 cm³) and saturated aqueous sodium hydrogen carbonate (7 cm³), dried (MgSO₄), filtered and evaporated to dryness in vacuo. Purification of the resultant residue by flash column chromatography (10-20% methanol-dichloromethane; gradient elution) yielded fully protected tripeptide 4 (0.038 g, 40%) as a colourless oil:; $\delta_H$ (400 MHz, CDCl₃) 1.62 (3H, s, Proα-CH₃), 1.83-2.44 (12H, m, Proβ-H₂, Proγ-H₂, Gluβ-H₂, Gluγ-H₂ and 2×Pyrβ-H₂), 2.80-2.90 (4H, m, 2×Pyrα-H₂), 3.43-3.72 (4H, m, NCH₂CO and Proδ-H₂), 4.52-4.54 (1H, m, Gluα-H), 5.08 (2H, s, OCH₂Ph), 5.08-5.14 (2H, m, OCH₂Ph), 7.27-7.37 (10H, m, 2×Ph) and 7.77 (1H, d, J 7.3, Glu-NH). $\delta_C$ (100 MHz, CDCl₃) 21.4 (CH₃, Proα-C), 23.1 (CH₂, Pyrβ-C and Proγ-C), 26.3 (CH₂, Gluβ-C), 29.8 (CH₂, Gluγ-C), 38.1 Proγ-C), 47.8 (CH₂, Proδ-C), 51.7 (CH, Gluα-C), 53.9 (CH₂, Pyrα-C), 57.9 (CH₂, NCH₂CO), 65.9 (CH₂, OCH₂Ph), 66.6 (CH₂, OCH₂Ph), 67.7 (quat., Proα-C), 128.1 (CH, Ph), 128.3 (CH, Ph), 128.5 (CH, Ph), 134.9 (quat., Ph), 135.4 (quat., Ph), 167.5 (quat., Pyr-CONH), 171.3 (quat., Glu-CO), 172.3 (quat., Glu-CO) and 173.4 (quat., Pro-CON).

9.4 Pyrrolidinoglycyl-L-2-Methyl-Proline-L-Glutamic Acid (Pyrrolidino G-2-MePE) 67

A mixture of protected peptide 6 (0.038 g, 0.07 mmol) and 10 wt. % palladium on activated carbon (0.073 g, 0.07 mmol) in 10% water-ethanol (8 cm³) was stirred under an atmosphere of hydrogen at room temperature for 20 h. The solution was filtered through a Celite™ pad and the filtrate evaporated to dryness to form a clear gum. The gum was dissolved in 10% water-ethanol (10 cm³) and refiltered through a Celite™ pad. The filtrate was evaporated to dryness to give a clear gum, which was placed on a vacuum line for 15 min and then triturated with anhydrous diethyl ether to form Pyrrolidino G-2MePE (0.024 g, 98%) as a clear gum.; $\delta_H$ (300 MHz; CD$_3$OD) 1.57 (3H, s, Proα-CH$_3$), 1.87-2.20 (10H, m, Proβ-H$_2$, Proγ-H$_2$, Gluβ-H$_2$ and 2×Pyrβ-H$_2$), 2.30-2.33 (2H, m, Gluγ-H$_2$), 3.35-3.45 (4H, m, 2×Pyrα-H$_2$), 3.59-3.62 (4H, m, Proδ-H$_2$ and NCH$_2$CO) and 4.18-4.25 (1H, m, Gluα-H); $\delta_C$ (75 MHz; CD$_3$OD) 21.9 (CH$_3$, Proα-C), 24.8 (CH$_2$, Pyrβ-C), 25.8 (CH$_2$, Proγ-C), 29.3 (CH$_2$, Gluβ-C), 32.6 (CH$_2$, Gluγ-C), 40.9 (CH$_2$, Proβ-C), 49.3 (CH$_2$, Proδ-C), 56.0 (CH, Gluα-C), 56.5 (CH$_2$, Pyrα-C), 70.0 (quat., Proα-C), 165.3 (quat, Pyr-CONH), 175.9 (quat, Pro-CONH) and 179.0 (quat, Gluγ-CO$_2$H).

Example 10

In Vitro Activity Studies of GPE Analogs

The synthesized analogs of GPE were subjected to in vitro evaluation of their efficacy in prevention of neuronal cell death.

a) Striatal Cell Culture

Methods and Materials

Two pregnant Wistar rats (gestational day 18) underwent Caesarean section according to approved procedures from the Animal Ethics Committee of the University of Auckland. The Wistar dams were anaesthetised in a CO2-enriched atmosphere and sacrificed by subsequent spinal cord dislocation. The embryos were removed from their embryonic sacs and decapitated. After incisions into the skull with fine scissors, the embryonic brain was removed with a fine spatula. Striatal tissue was separated from neocortical tissue under the microscope and placed into serum-free DMEM/F-12 medium supplemented with penicillin/streptomycin (100 u/mL). Tissue underwent 15 trituration steps using a P1000 pipettor to obtain dissociated cells, which were centrifuged for 5 min at 250 G (4° C.) and the supernatant was discarded. Cells were re-suspended into 1 mL DMEM/F-12 medium and were kept on ice. Cell suspension (400,000 cells/cm2) was applied to 0.1 mg/mL poly-L-lysine pre-coated 96-well plates (3 h at 37° C.) and the volume was increased up to 100 µL with DMEM/F-12+5% FBS. Cells were cultivated at 37° C. in 100% humidity in a 5% CO2 atmosphere. After 24 h the medium was changed to serum-free Neurobasal/B27. Cell medium was changed every 3 days and maintained until 8 days in vitro (DWV).

Cellular Injury, Drug Administration and Cellular Survival Analysis

Striatal cells were injured after 2, 3, 7 or 8 days in vitro. The injury paradigm involved 30 nM okadaic acid treatment with simultaneous administration of a GPE analog of this invention for 24 h. 1 µL of 3 µM okadaic acid stock solution together with 1 µL of GPE analog dissolved in PBS (vehicle received 2 µL of PBS) were incubated for 24 h with the striatal cells. Subsequently, 20 µL MTT (5 mg/mL in PBS) was added for 4 h. The reaction was terminated by addition of 100 µL 4% sodium dodecyl sulfate (SDS) solution. After 16-24 h incubation time, photometric extinction values are read at 595 nm. The difference between the vehicle and the okadaic acid injury condition was calculated. This value was set as the theoretical 100% recovery value. Measured values for the tested compounds were expressed in percentage of the 100% value. The unpaired Student's t-test was used for statistical analysis.

b) Cerebellar Cell Culture

Methods and Materials

Postnatal day 3, 4 or 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 65% stock D (+)glucose/1 ml PBS) in a large Petri dish, chopped up into smaller sections and triturated with a 1 ml insulin syringe via a 23 gauge (0.4 mm) needle, and then squirted back into the glucose solution in the Petri dish. The tissue was sieved through (125 pm pore size) and centrifuged (2 minutes at 60×g) twice to exchange the medium into serum-free BSA-supplemented START V medium (Biochrom, Germany). The second centrifugation step was done with 1 ml of START V medium. The microexplants were reconstituted into 500 µl of START V medium and put on ice.

Preparation of Culture Cover Slips and Cultivation of Cerebellar Cells

Two hours after PDL-coating (100 pg/ml), the slides were washed with Millipore H$_2$O and air dried. Each slide was placed into a small Petri dish (diameter: 35 mm) and 40P1 of START V/cell suspension was added. The tissue was incubated for 2 hours at 34° C. (settlement period). START V-medium (1 ml) was added to the Petri dish and cultivated at 34° C. in the presence of 5% CO$_2$ in air at 100% humidity for 48 hours.

Cellular Injury, Drug Administration and Cellular Survival Analysis

10 µl of toxin 1 (L-glutamate-100 mM in Millipore water; final concentration: 0.5 mM) and 10 µl of toxin 2 (3-nitropropionic acid-50 mM-pH 7-in Millipore water, final concentration: 0.5 mM) was applied simultaneously with the compounds to be tested (10 mM stock solution prepared in PBS and diluted to final concentrations between 1-100 nM). In each case, the drugs were left in contact with the explants for the duration of the study.

After explants were exposed to a GPE analog of this invention for the study period, cells were then rinsed in PBS and then fixed in increasing concentrations of paraformaldehyde (500 µl of 0.4% PFA was applied; then 1.2% PFA; then 3% PFA and finally 4% PFA (each fixation step: 2-3 minutes). Finally, the microexplants were rinsed in PBS. Neurons in the explants were then evaluated for morphology (presence of neurites) and counted as live cells per microscopic field. Four fields displaying highest cell density were counted per cover slip and the data presented as mean ±standard error of the mean (SEM); n=4 each. Statistical significance was evaluated by using the non-paired Student's t-test.

c) Rat Cortical Dissociated Cell Culture

Materials

Embryonic E18/19 wistar rats were used for the generation of dissociated cortical cell cultures. The rear portion (occipital cortex-area 17/18 of the visual cortex) of the cortical plate is used for the generation of the cultures. Cells were grown for 3-10 DIV in one part of serum-free medium and one part of rat cortex-derived cultivated astrocytic-conditioned medium (ACM).

Methods 96-well tissue culture plates were coated with 0.2 mg/ml poly-L-lysine followed by 2 µg/ml laminin. Subsequently 60 µl of ACM were added per well and plate was stored at 37° C. until plating of cortical cells.

Production of Astrocytic-Conditioned Medium (ACM)

Whole cortices of P1/2 wistar pups were collected into separate tubes containing 4 ml DMEM-1 cortex per tube. The tissues were triturated a few times with a 5 ml sterile pipette to break up them up into smaller pieces. Each tube was poured separately into a reagent reservoir and triturated once with a 5 ml syringe and 18 gauge drawing needle. The mixture was then filtered through a 100 μm cell strainer into a 50 ml centrifuge tube. The strainer was washed with 5 ml DMEM. The cell solution was extended with DMEM to 50 ml of volume. The solution was then centrifuged for 5mins at 350g at RT. The cells were resuspended in 40 ml of DMEM+10% FBS. The cells were then reconstituted into a 75 $cm^2$ cell flask and incubated at 37° C./10% $CO_2$/100% humidity in the presence of 5 nM okadaic acid. This toxin killed neurons to enrich the astrocytic entity in the culture. The medium was replaced after 1 day with fresh DMEM+10% FBS. The cell growth was monitored and media+FBS replaced twice weekly until the cells were confluent (~10-14 days). Once the confluency reached, the cells were washed once with 20 ml sterile PBS. Cells were incubated for 3 days in 30 ml Neurobasal medium+B27 supplement to maintain cells under serum-free conditions. Cell supernatant was then filter through a 0.22 μm sterile filter and frozen in aliquots at −80° C.

Cortical Cell Dissection and Plating

Visual cortices from embryos were collected and dissected–all steps were done in PBS+0.65% glucose. The tissues were stored in PBS+glucose solution on ice until all dissection was completed. Tissue material was centrifuged at 350g for 5 mins at RT. The supernatant was removed and cell pellets were incubated in 5 ml trypsin/EDTA solution (Invitrogen) for 8 mins at 37° C. Proteolysis was stopped by addition of one part of DMEM+10% FBS. Subsequently, the tissued were centrifuged at 350g for 5 mins at RT. The pellet was collected, washed (centrifugation) twice in NB/B27 medium (Invitrogen) and resuspended in 1 ml NB/B27 medium. Tissue was transferred into a petri dish and triturated twice with a glass pasteur pipette attached to a pipette to break up large pieces of tissue. The tissue was then triturated twice using a 1 ml syringe and 22 gauge needle and passed through a 100 μm cell strainer to remove remaining large tissue pieces. The cells were washed with 1 ml NB/B27. The number of viable neurons was counted and the percentage of cell viability determined. We diluted the cell solution to the extent that the final cell count is 50,000 cells per 60 μl (833,333 cells/ml). The cortical cells were incubated at 37° C./10% $CO_2$/100% humidity.

Injury—Neuronal Rescue Agent and Neuroprotection Analysis

In order to induce neuronal injury the phosphatase 1/2A antagonist okadaic acid is added for 24 hrs. Simultaneously, an analog of GPE of this invention was administered. After 24 hrs metabolic activity was measured by addition of MTT for 2-4 hrs followed by addition of SDS-solution and photometric end point measurement at 595 nm.

Student's unpaired t-test is used for testing for statistical significance when comparing uninjured controls with the injured neuronal rescue agent containing conditions.

RESULTS

In the absence of any GPE analog, okadaic acid treatment resulted in an approximately 30% decrease in viable cells (FIG. 1; second column from the left) compared to untreated control cells (left column; open bar). In other studies presented herein, okadaic acid decreased the numbers of viable cells by about 10% to about 50% (FIGS. 2-6).

FIG. 1 also shows that GPE treatment (hatched bars) reversed the okadaic acid induced loss of cell viability. Similarly, analog 49 (Glycyl-L-thia-5,5-dimethylprolyl-L-glutamic acid) is neuroprotective. Analog 49 protected the cells from okadaic acid-induced loss of cell viability in a concentration-dependent fashion. In the concentration range from 10 nM to 10 μM, treatment with analog 49 produced 100% protection against loss of neural cell viability casued by okadaic acid.

Figure 2:
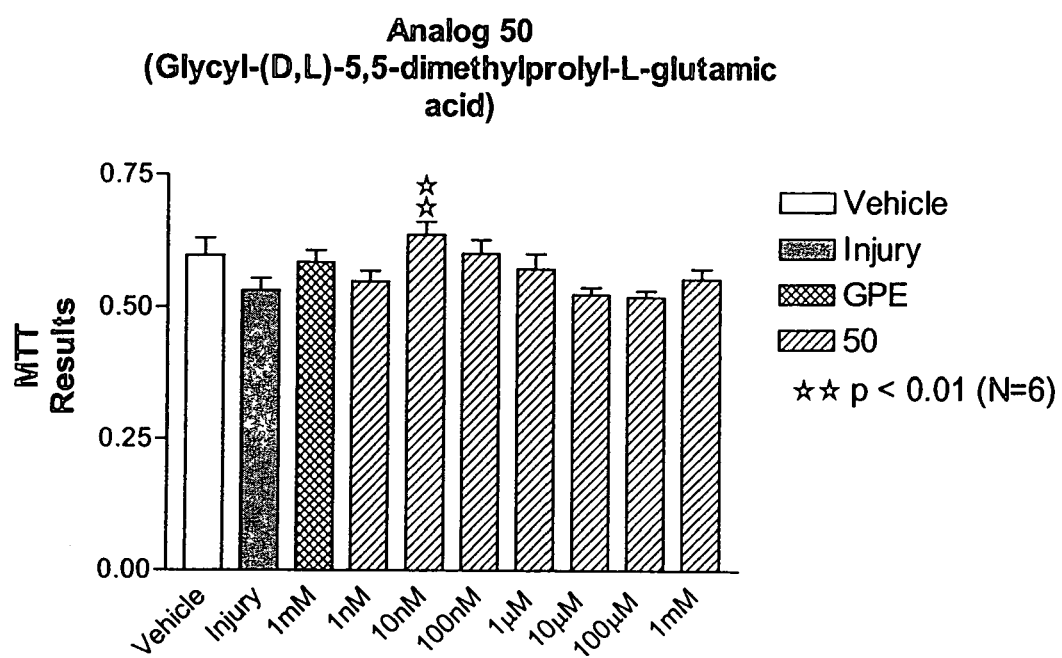
FIG. 2 is a graph showing effects of analog 50 (Glycyl-(D,L)-5,5-dimethylprolyl-L-glutamic acid) on neuronal survival following excitotoxic oxidative stress in cortical cell culture induced by 100 μM $H_2O_2$.

FIG. 2 shows that as with analog 49, analog 50 (Glycyl-(D,L)-5,5-dimethylprolyl-L-glutamic acid) is also neuroprotective (FIG. 2). In the concentration range from 10 nM to 100 nM, treatment with analog 50 produced 100% protection from loss of neural cell viability caused by okadaic acid.

Figure 3:
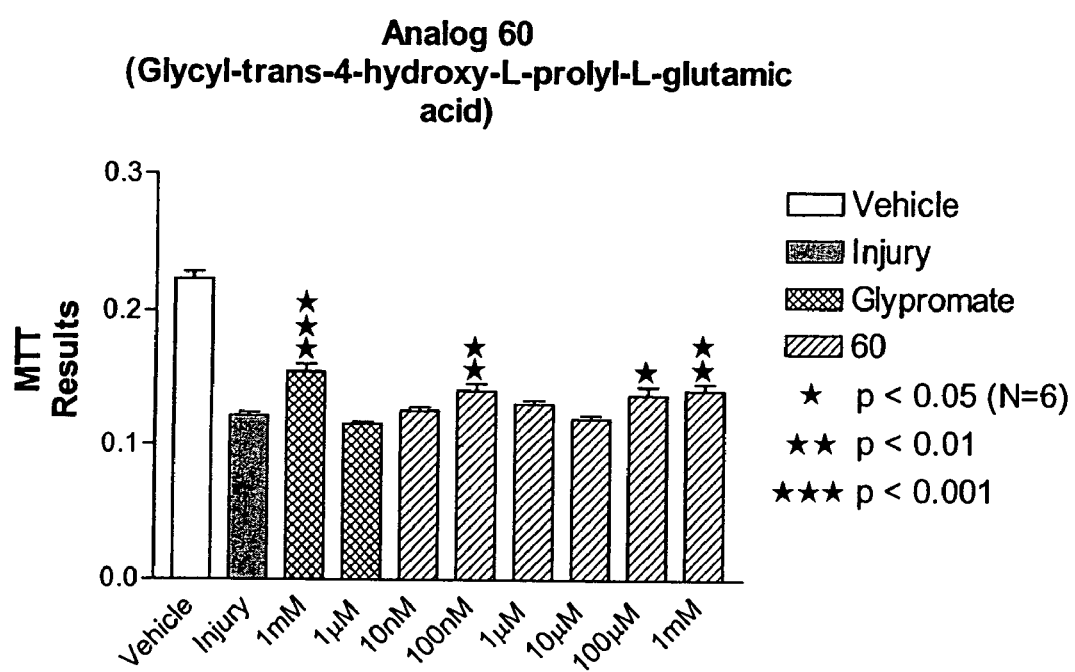
FIG. 3 is a graph showing effects of analog 60 (Glycyl-trans-4-hydroxy-L-prolyl-L-glutamic acid) on neuronal survival following administration of apoptosis-inducing toxin (30 nM okadaic acid) in striatal cell culture.

FIG. 3 shows that treatment with analog 60 (Glycyl-trans-4-hydroxy-L-prolyl-L-glutamic acid) is also neuroprorotective, with the statistically significant effects observed at concentrations of 100 nM and 100 μM and 1 mM.

Figure 4:
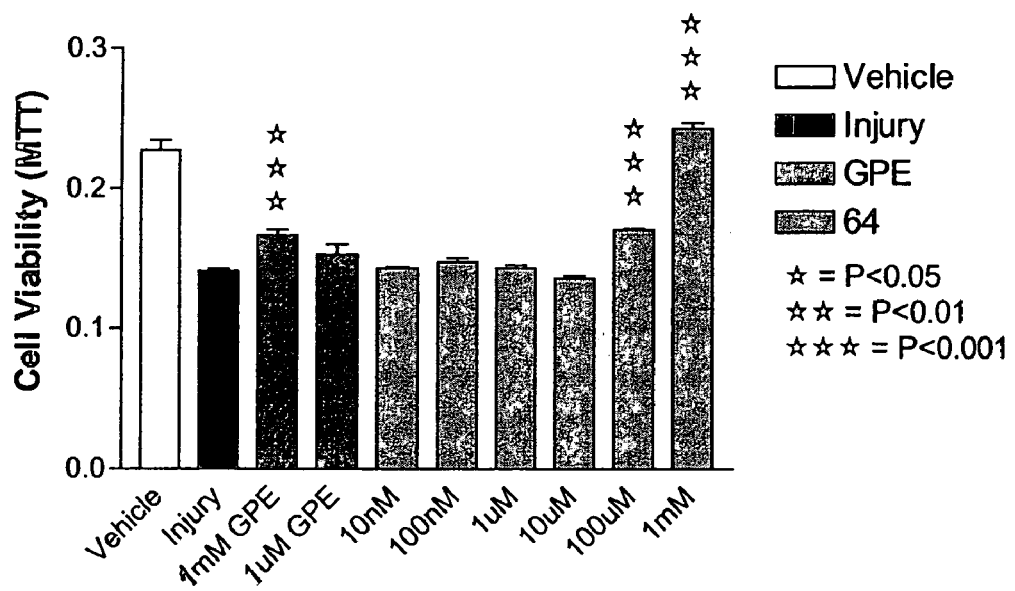
FIG. 4 is a graph showing effects of analog 64 (Aminoisobutryl-L-prolyl-L-glutamic acid) on neuronal survival following administration of apoptosis-inducing toxin (30 nM okadaic acid) in striatal cell culture.

FIG. 4 shows that analog 64 (Aminoisobutryl-L-prolyl-L-glutamic acid) AibPe is neuroprotective. In a concentration range from 100 μM to 1 mM, analog 64 was more effective than GPE. At a concentration of 1 mM, treatment with analog 64 produced complete protection from the loss of neural cell viability induced by okadaic acid.

Figure 5:
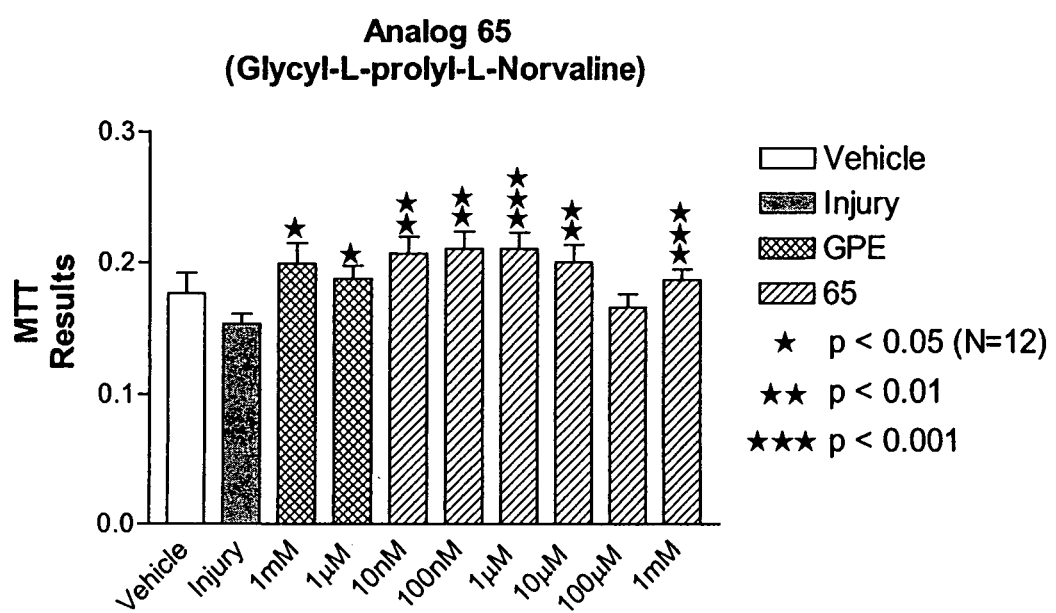
FIG. 5 is a graph showing effects of analog 65 (Glycyl-L-prolyl-L-Norvaline) on neuronal survival following administration of apoptosis-inducing toxin (100 nM okadaic acid) in cortical cell culture.

FIG. 5 shows that analog 65 (Glycyl-L-prolyl-L-Norvaline) is neuroprotective over a broad range of concentrations, from 10 nM to 1 mM. At nearly every concentration tested, the cells treated with analog 65 showed 100% protection against loss of cell viability induced by okadaic acid.

Figure 6:
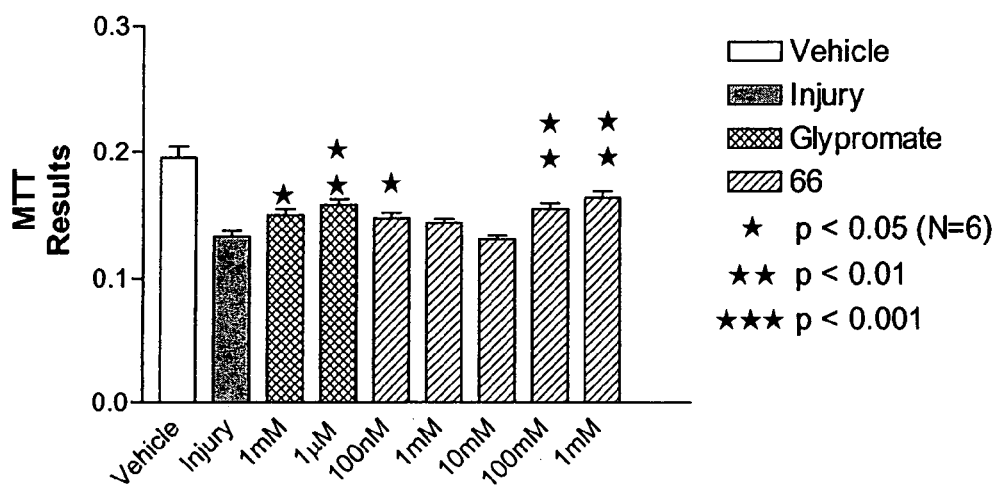
FIG. 6 is a graph showing effects of analog 66 (Glycyl-D,L-pipecolinyl-L-glutamic acid) on neuronal survival following administration of apoptosis-inducing toxin (okadaic acid) in striatal cell culture.

FIG. 6 shows that analog 66 (Glycyl-D,L-pipecolinyl-L-glutamic Acid) is neuroprotective, with statistically significant effects observed at concentrations of 100 nM, 100 mM and 1 mM.

Figure 7:
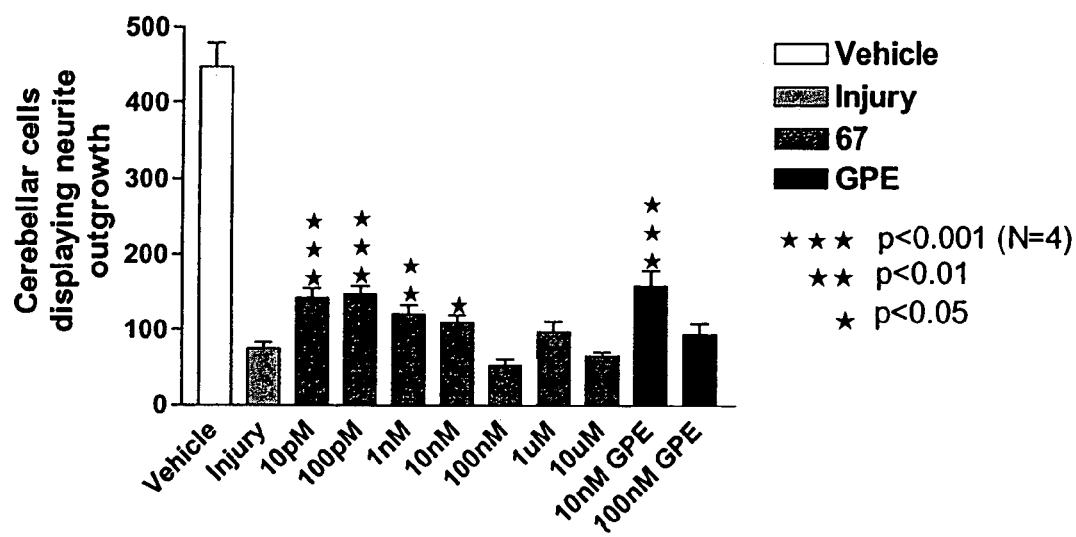
FIG. 7 is a graph showing effects of analog 67 (Pyrrolidinoglycyl-L-2-Methyl-proline-L-Glutamic Acid) on neuronal survival following excitotoxic/oxidative stress (induced by 0.5 mM 3-NP glutamate) in cerebellar cell culture.

FIG. 7 shows that analog 67 (Pyrrolidinoglycyl-L-2-Methyl-proline-L-Glutamic Acid) protected cerebellar cells from loss of neurites caused by okadaic acid. Statistically significant effects were observed at concentrations of 10 μM-10 nM.

One can appreciate from comparison of FIGS. 1-6 and FIG. 7, that injury induced by okadaic acid can be more sensitively detected by measuring neurite outgrowth than by cell viability. Okadaic acid decreased viability by from about 10% to about 50% (FIGS. 1-6). In contrast, okadaic acid decreased the number of cells having neurites by over 80%. Regardless of how injury was assessed, each of the GPE analogs tested had statistically significant neuroprotective effects.

We conclude from these studies that analogs of GPE of this invention can protect neural cells from loss of viability and/or loss of neurites in response to the well-known neurotoxin, okadiac acid. Because okadaic acid toxicity produces histological changes similar to those produced by other causes of neural injury, including hypoxia/ischemia, stroke, Parkinson's disease and the like, we conclude that this system for studying neural cell protection is predictive of effects that will be observed using other types of neurodegenerative stimuli. Moreover, the neuroprotective effects observed in these studies are therefore highly likely to correlate with other systems for studying neuroprotection, including in vivo studies in experimental animals such as rats. Further, because compounds related to GPE have been show to protect animals in vivo against loss of neurons and functional neurological deficits associated by a variety of different conditions, we conclude from these studies, that GPE analogs of this invention can be useful in treating a variety of conditions associated with neurological deficits and neurological diseases.

It can be appreciated that this invention is described with respect to specific embodiments thereof. Persons of ordinary skill will be able to produce variations and other embodiments based on the disclosures and teachings herein without undue experimentation and with a reasonable likelihood of success. All of these other embodiments are considered to be part of this invention.

We claim:

1. A compound having the formula:

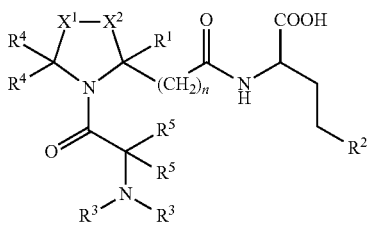

or a pharmaceutically acceptable salt thereof, wherein:
the bond between $X^1$ and $X^2$ is either saturated or unsaturated;
$X^1$ is S;
$X^2$ is selected from the group consisting of $CH_2$, $CH_2CH_2$ and in the case where the bond between $X^1$ and $X^2$ is unsaturated, CH;
$R^1$ is selected from the group consisting of H, alkyl, alkenyl, aryl, arylalkyl, substituted alkyl, substituted alkenyl, substituted aryl or substituted arylalkyl;
$R^2$ is $CH_3$ or COOH;
$R^3$ is selected from the group consisting of H, alkyl or $NR^3R^{3'}$ taken together is pyrrolidino or piperidino;
$R^4$ is selected from the group consisting of H, alkyl, alkenyl, aryl, arylalkyl, substituted alkyl, substituted alkenyl, substituted aryl or substituted arylalkyl;
$R^5$ is selected from the group consisting of H, alkyl, alkenyl, aryl, arylalkyl, substituted alkyl, substituted alkenyl, substituted aryl or substituted arylalkyl; and
n is an integer from 0 to 2.

2. The compound of claim 1 where $X^1$ is S; $X^2$ is $CH_2$; $R^1$ is H; $R^2$ is COOH; $R^3$ is H; $R^4$ is H; $R^5$ is H; and n is 0 (Glycyl-L-4-thiaprolyl-L-glutamic acid trifluoroacetate).

3. The compound of claim 1 where $X^1$ is S; $X^2$ is $CH_2$; $R^1$ is H; $R^2$ is COOH; $R^3$ is H; $R^4$ is $CH_3$; $R^5$ is H; and n is 0 (Glycyl-L-thia-5,5-dimethylprolyl-L-glutamic acid ("G-thiadiMePE")).

4. A pharmaceutical composition comprising a compound of claim 1 and a pharmaceutically acceptable excipient.

5. The pharmaceutical composition of claim 4, further comprising a binder.

6. The pharmaceutical composition of claim 4, further comprising a capsule.

7. A method of treating an animal to protect neural cells from death or degeneration as a result of an injury or disease wherein the injury or disease is a result of one or more conditions selected from the group consisting of chronic or acute encephalomyelitis, encephalitis, optic neuritis, transverse myelitis, meningitis, panencephalitis, Devic's disease, progressive multifocal leukoencephalopathy, central pontine myelinolysis, neuromyelitis optica, neuroblastoma, head injury, traumatic brain injury, stroke, ischemic injury, hypoxic injury, reperfusion injury, epilepsy, cardiac artery bypass graft surgery, toxin damage, radiation damage and asphyxia comprising administering to said animal an effective amount of one or more compounds of claim 1.

8. The method of claim 7 wherein the animal is human.

9. The method of claim 7 wherein the injury or disease is characterised by apoptotic neuronal death.

10. The method of claim 7 wherein the injury or disease is characterised by necrotic neuronal death.

11. The method of claim 7, wherein the injury or disease is characterized by neuronal cell degeneration.

12. A pharmaceutical composition comprising a compound of claim 3 and a pharmaceutically acceptable excipient.

13. The pharmaceutical composition of claim 12, further comprising a binder.

14. The pharmaceutical composition of claim 12, further comprising a capsule.

* * * * *